US008216837B2

(12) United States Patent
Muraki et al.

(10) Patent No.: US 8,216,837 B2
(45) Date of Patent: Jul. 10, 2012

(54) METHOD OF PRODUCING LYMPHOCYTES

(75) Inventors: Nobuko Muraki, Otsu (JP); Mitsuko Ideno, Otsu (JP); Kinuko Nagamine, Otsu (JP); Fuyuko Takashima, Otsu (JP); Eiji Kobayashi, Otsu (JP); Akiko Kato, Otsu (JP); Takahiro Marui, Otsu (JP); Hiroaki Sagawa, Otsu (JP); Tatsuji Enoki, Otsu (JP); Ikunoshin Kato, Otsu (JP)

(73) Assignee: Takara Bio Inc., Otsu-shi (JP)

( * ) Notice: Subject to any disclaimer, the term of this patent is extended or adjusted under 35 U.S.C. 154(b) by 585 days.

(21) Appl. No.: 12/303,911

(22) PCT Filed: Jun. 7, 2007

(86) PCT No.: PCT/JP2007/061555
§ 371 (c)(1),
(2), (4) Date: Dec. 8, 2008

(87) PCT Pub. No.: WO2007/142300
PCT Pub. Date: Dec. 13, 2007

(65) Prior Publication Data
US 2010/0255578 A1    Oct. 7, 2010

(30) Foreign Application Priority Data

Jun. 9, 2006  (JP) .................................. 2006-161386
Feb. 16, 2007  (JP) .................................. 2007-036963

(51) Int. Cl.
*C12N 5/071* (2010.01)
(52) U.S. Cl. ...................................... 435/372; 435/372.3
(58) Field of Classification Search .......................... None
See application file for complete search history.

(56) References Cited

U.S. PATENT DOCUMENTS

| | | | | |
|---|---|---|---|---|
| 5,136,023 A | * | 8/1992 | Hashino et al. | ............... 530/350 |
| 5,198,423 A | | 3/1993 | Taguchi et al. | |
| 6,033,907 A | * | 3/2000 | Williams | ...................... 435/325 |
| 6,060,317 A | * | 5/2000 | Malech | .......................... 435/456 |
| 6,426,042 B1 | | 7/2002 | Asada et al. | |
| 2004/0115809 A1 | | 6/2004 | Sagawa et al. | |
| 2005/0042208 A1 | | 2/2005 | Sagawa et al. | |
| 2005/0227354 A1 | | 10/2005 | Sagawa et al. | |

FOREIGN PATENT DOCUMENTS

| | | |
|---|---|---|
| EP | 1 666 589 A1 | 6/2006 |
| JP | 2-311498 A | 12/1990 |
| JP | 2007-61020 A | 3/2007 |
| WO | WO-96/06929 A2 | 3/1996 |
| WO | WO-97/18318 A1 | 5/1997 |
| WO | WO-97/32970 A1 | 9/1997 |
| WO | WO-02/14481 A1 | 8/2001 |
| WO | WO-03/016511 A1 | 2/2003 |
| WO | WO-03/080817 A1 | 10/2003 |
| WO | WO-2005/019450 A1 | 3/2005 |
| WO | WO-2007/040105 A1 | 4/2007 |

OTHER PUBLICATIONS

Yamada et al., 1991, J. Immunol. vol. 146: 53-56.*
Chen et al., 1994, J. Immunol. vol. 153: 3630-3638.*
English translation of JP 2007-061020, Mar. 2007, 1-26.*
Mitsuko Ideno et al.; "Novel expansion methods of CTL using recombinant fibronectin fragments" Proceedings of the Japanese Cancer Association, (2003), p. 175.
Hiroaki Sagawa et al.; "Improvement of LAK cells expansion method with combined use of RetroNectin (TM) and anti-CD3 antibody", Proceedings of the Japanese Cancer Association, (2003), p. 438.
Nobuko Muraki et al.; "T cell expansion using RetroNectin (I): Useful method to expand T cells, characterized by high portion of naive T-like cells", Proceedings of the Japanese Cancer Association, (Aug. 2006), p. 330.
Mitsuko Ideno et al.; "T cell expansion using RetroNectin (II): RN-T cells contain high portion of a naive T-like cells and show high ability of antigen recognition", Proceedings of the Japanese Cancer Association, (Aug. 2006), p. 330.
Cor HJ Lamers et al.; "Protocol for gene transduction and expansion of human T lymphocytes for clinical immunogene therapy of cancer", Cancer Gene Therapy, (2002), vol. 9, pp. 613-623.
Philip D. Greenberg; "Adoptive T Cell Therapy of Tumors: Mechanisms Operative in the Recognition and Elimination of Tumor Cells", Advances in Immunology, 1991, vol. 49, pp. 281-355.
Pierre Reusser et al.; "Cytotoxic T-Lymphocyte Response to Cytomegalovirus After Human Allogeneic Bone Marrow Transplantation: Pattern of Recovery and Correlation with Cytomegalovirus Infection and Disease", Blood, vol. 78, No. 5, Sep. 1, 1991, pp. 1373-1380.
Stanley R. Riddell et al.; "Class I MHC-Restricted Cytotoxic T Lymphocyte Recognition of Cells Infected . . . ", The Journal of Immunology, Vo. 146, No. 8, Apr. 15, 1991, pp. 2795-2804.
Stanley R. Riddell et al.; "The use of anti-CD3 and anti-CD28 monoclonal antibodies to clone and expand human antigen-specific T cells"; Journal of Immunological Methods, 128(2), pp. 189-201.
Monto Ho et al., "A Phase 1 Study of Adoptive Transfer of Autologous CD8+ T Lymphocytes . . . ", Blood, vol. 81, No. 8, Apr. 15, 1993, pp. 2093-2101.
Steven A. Rosenberg et al.; "A Progress Report on the Treatment of 157 Patients With Advanced Cancer Using Lymphokine-Activated . . . ". The New England Journal of Medicine, vol. 316, No. 15, Apr. 9, 1987, pp. 889-897.

(Continued)

*Primary Examiner* — Amy Juedes
(74) *Attorney, Agent, or Firm* — Birch, Stewart, Kolasch & Birch, LLP

(57) ABSTRACT

A method of producing lymphocytes characterized by comprising the step of culturing lymphocytes in the presence of a modified recombinant fibronectin fragment which has overlapping parts of the heparin-binding domain of fibronectin. This method makes it possible to achieve a high cell proliferation rate. The lymphocytes obtained thereby are appropriately usable in, for example, adoptive immunotherapy and, therefore, expected as highly useful in the clinical field. Moreover, a novel modified recombinant fibronectin fragment is provided.

5 Claims, 2 Drawing Sheets

OTHER PUBLICATIONS

Steven A. Rosenberg et al.; "Use of Tumor-Infiltrating Lymphocytes and Interleukin-2 in the Immunotherapy . . . ", The New England Journal of Medicine, Dec. 22, 1988, vol. 319, No. 25, pp. 1676-1680.
Deane F. Mosher; published in 1989, Fibronectin, Academic Press Inc., 1-24.
Fusao Kimizuka et al.; "Production and Characterization of Functional Domains of Human Fibronectin Expressed . . . "; J. Biochem., vol. 110, No. 2, 1991, 284-291.
Helumt Hanenberg et al.; "Optimization of Fibronectin-Assisted Retroviral Gene Transfer into . . . ", Human Gene Therapy, 8(18), Dec. 10, 1997); 2193-2206.
David A. Williams et al.; "Fibronectin and VLA-4 in haematopoietic stem cell-microenvironment interactions", Nature, vol. 352, pp. 438-441, Aug. 1, 1991.
Albert R. Kornblihtt et al.; "Primary structure of human fibronectin: differential splicing may generate at least 10 polypeptides from a single gene". The EMBO Journal, vol. 4, No. 7, pp. 1755-1759, 1985.
Kiyotoshi Sekiguchi et al.; "Human Liver Fibronectin Complementary DNAs: Identification of . . . ", Biochemistry, No. 25, pp. 4936-4941, 1986.
Maria A. Bednarek et al.; "The Minimum Peptide Epitope from the Influenza Virus Matrix Protein", The Journal of Immunology, vol. 147, No. 12, pp. 4047-4053, Dec. 15, 1991.
J. Carter et al.; "Development and maintenance of bovine cytotoxic lymphocytes with recombinant human interleukin-2"; Immunology; No. 57, pp. 123-129, 1986.
Tadatoshi Takayama et al.; "Adoptive immunotherapy to lower post-surgical recurrence rates of hepatocellular carcinoma: a randomised trial"; The Lancet, vol. 356, pp. 802-807, Sep. 2, 2000.
Rudolf Lichtenfels et al.; "Care-lass (calcein-release-assay), an improved fluoroscence-based . . . "; Journal of Immunological Methods, No. 172, pp. 227-239; 1994.
Paul Lehner et al.; "Human HLA-A0201 restricted Cytotoxic T Lymphocyte Recognition . . . ", J. Ex. Med.; vol. 181, pp. 79-91, Jan. 1, 1995.
"Isolation of Human NK Cells and Generation of LAK Activity", Current Protocols in Immunology, Supplement 17.
Saibo Kogaku; "Bulk Culture of Human Lymphocytes"; Cell Technology, No. 14(2), pp. 223-227, 1995.
Saibo Baiyo; "Bulk Culture Method for Human Lymphocytes for use in Adoptive Immunotherapy"; Cell Culture; No. 17(6), pp. 192-195, 1991.
Hanenberg et al., "Colocalization of retrovirus and target cells on specific fibronectin fragments increases genetic transduction of mammalian cells," Nature Medicine, vol. 2, No. 8, Aug. 1996, XP-000916458, pp. 876-882.
Supplementary European Search Report in EP 07744884.3 mailed Jul. 9, 2010.

* cited by examiner

[Figure 1]
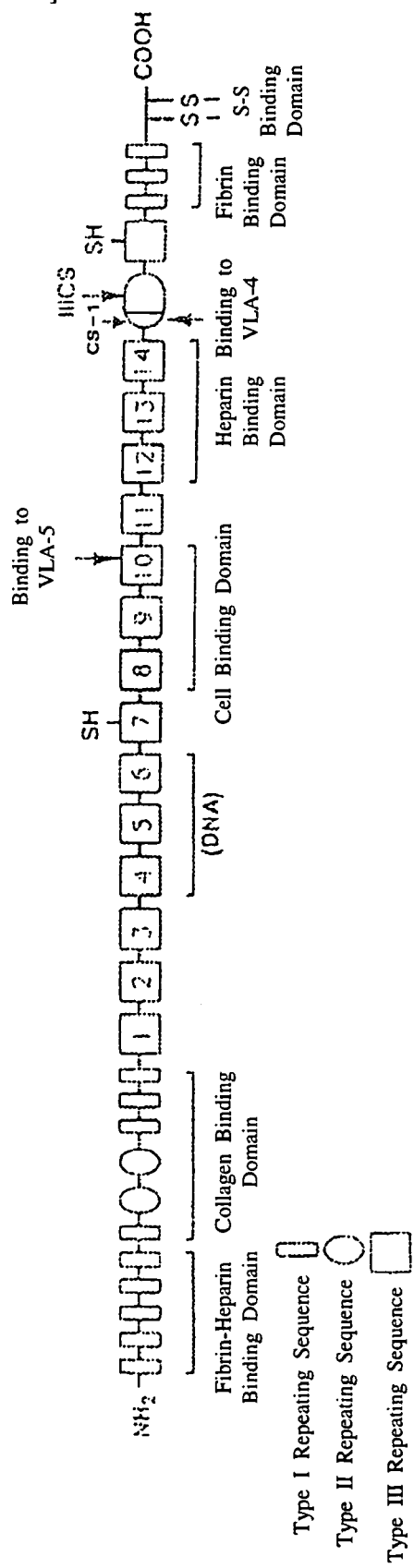

[Figure 2]
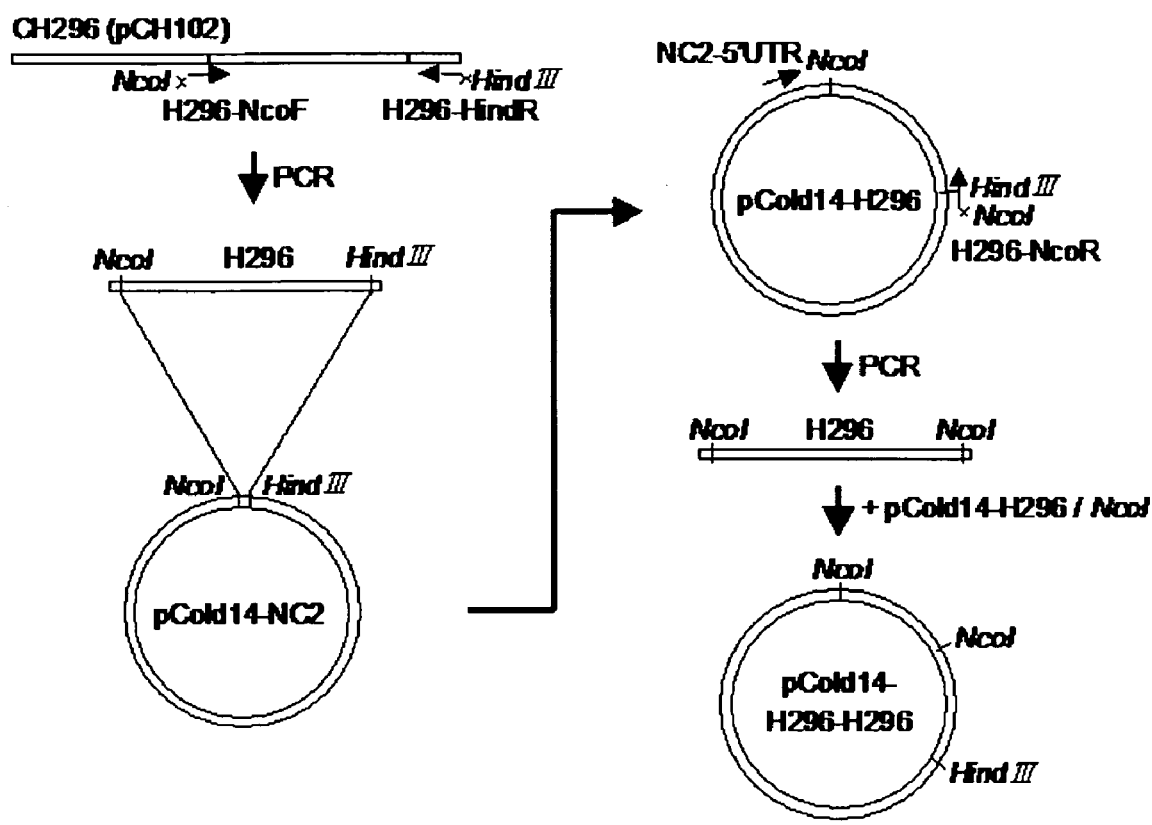

US 8,216,837 B2

METHOD OF PRODUCING LYMPHOCYTES

This application is a National Stage of PCT International Application No. PCT/JP2007/061555 filed on Jun. 7, 2007, which claims the benefit of priority of Japanese Patent Application Nos. 2006-161386, filed on Jun. 9, 2006, and 2007-036963, filed on Feb. 16, 2007.

TECHNICAL FIELD

The present invention relates to a method for preparing lymphocytes, which is useful in the field of medicine.

BACKGROUND ART

A living body is protected from foreign substances mainly by an immune response, and an immune system has been established by various cells and the soluble factors produced thereby. Among them, leukocytes, especially lymphocytes, play a key role. The lymphocytes are classified in two major types, B lymphocyte (which may be hereinafter referred to as B cell) and T lymphocyte (which may be hereinafter referred to as T cell), both of which specifically recognize an antigen and act on the antigen to protect the living body.

T cell is subclassified to helper T cell having CD (Cluster of Differentiation) 4 marker (which may be hereinafter referred to as $T_H$), mainly involved in assisting in antibody production and induction of various immune responses, and cytotoxic T cell having CD8 marker ($T_c$: cytotoxic T lymphocyte, also referred to as killer T cell, which may be hereinafter referred to as CTL), mainly exhibiting a cytotoxic activity. CTL, which plays the most important role in recognizing, destroying and eliminating tumor cell, virus-infected cell or the like, does not produce an antibody specifically reacting with an antigen like B cell, but directly recognizes and acts on antigens (antigenic peptide) from a target cell which is associated with major histocompatibility complex [MHC, which may be also referred to as human leukocyte antigen (HLA) in human] Class I molecules existing on the surface of the target cell membrane. At this time, T cell receptor (hereinafter referred to as TCR) existing on the surface of the CTL membrane specifically recognizes the above-mentioned antigenic peptides and MHC Class I molecules, and determines whether the antigenic peptide is autologous or nonautologous. Target cell which has been determined to be nonautologous is then specifically destroyed and eliminated by CTL.

Recent years, a therapy which would cause a heavy physical burden on a patient, such as pharmacotherapy and radiotherapy, has been reconsidered, and an interest has increased in an immunotherapy with a light physical burden on a patient. Especially, there has been remarked an effectiveness of adoptive immunotherapy in which a lymphocyte such as CTL that specifically reacts with an antigen of interest is induced ex vivo from a lymphocyte derived from a human, or the lymphocyte is expanded without induction, and then transferred to a patient. For example, it has been suggested in an animal model that adoptive immunotherapy is an effective therapy for virus infection and tumor (for example, Non-Patent Publications 1 and 2). In this therapy, it is important to maintain or increase the number of the CTLs in a state in which the antigen-specific cytotoxic activity of the cells is maintained or enhanced.

In the adoptive immunotherapy as described above, it is necessary to administer cytotoxic lymphocytes in the number of cells of a given amount or larger in order to obtain a therapeutic effect. In other words, it can be said that the biggest challenge is to obtain the above number of cells ex vivo in a short period of time.

In order to maintain and enhance an antigen-specific cytotoxic activity of CTL, there has been generally employed a method of repeating stimulation with an antigen of interest when a specific response to an antigen for CTL is induced. However, in this method, the number of CTL finally obtained is usually decreased, so that a sufficient number of cells cannot be obtained.

Next, regarding the preparation of the antigen-specific CTL, there has been each reported a method for isolating and expanding a CMV-specific CTL clone using autologous CMV infected fibroblast and IL-2 (for example, Non-Patent Publication 3) or using anti-CD3 monoclonal antibody (anti-CD3 mAb) and IL-2 (for example, Non-Patent Publication 4).

Furthermore, Patent Publication 1 discloses an REM method (rapid expansion method). This REM method is a method for expanding a primary T cell population containing antigen-specific CTLs and $T_H$ in a short period of time. In other words, this method is characterized in that a large amount of T cell can be provided by expanding individual T cell clones, and that the number of antigen-specific CTLs is increased using an anti-CD3 antibody, IL-2, and PBMCs (peripheral blood mononuclear cells) made deficient in an ability for expansion by irradiation, and Epstein-Barr virus (hereinafter abbreviated as EBV)-infected cells.

In addition, Patent Publication 2 discloses a modified REM method, wherein the method is a method using as feeder cells a nondividing mammal cell strain expressing a T-cell stimulating component which is distinguishable from PBMCs to reduce an amount of PBMCs used.

As lymphocytes which are effective for the treatment of a disease other than CTLs, there has been known, for example, lymphokine-activated cells (for example, Non-Patent Publications 5 and 6) and tumor-infiltrating lymphocytes (TILs) induced with interleukin-2 (IL-2) in a high concentration (for example, Non-Patent Publication 7).

The lymphokine-activated cells are a functional cell population having a cytotoxic activity, which are obtained by adding IL-2 to peripheral blood (peripheral blood leukocyte), umbilical cord blood, tissue fluid or the like containing lymphocytes, and culturing the cells in vitro for several days. In the step of culturing the lymphokine-activated cells, proliferation of the lymphokine-activated cells is further accelerated by adding an anti-CD3 antibody thereto. The lymphokine-activated cells thus obtained have a cytotoxic activity non-specifically to various cancer cells and other targets.

Fibronectin is a gigantic glycoprotein having a molecular weight of 250 thousands, which exists in an animal blood, on the surface of a cultured cell, or in an extracellular matrix of a tissue, and has been known to have various functions. A domain structure thereof is divided into seven portions (FIG. 1 et seq), wherein three kinds of similar sequences are contained in an amino acid sequence thereof, repetitions of each of these sequences constituting the entire sequence. Three kinds of the similar sequences are referred to as type I, type II and type III. Among them, the type III is constituted by 71 to 96 amino acid residues, wherein an identity of these amino acid residues is 17 to 40%. In fibronectin, there are fourteen type III sequences, among which the 8th, 9th and 10th sequences (each being hereinafter referred to as III-8, III-9 and III-10) are contained in a cell binding domain, and the 12th, 13th and 14th sequences (each being hereinafter referred to as III-12, III-13 and III-14) are contained in a heparin binding domain In addition, a VLA (very late activation antigen)-5 binding region is contained in III-10, and its core sequence is RGDS. In addition, a region referred to as IIICS exists at a C-terminal side of the heparin binding domain. A region referred to as CS-1 consisting of 25 amino acids and having a binding activity to VLA-4 exists in IIICS (for example, Non-Patent Publications 8 to 10).

In the preparation of the lymphokine-activated cells and the cytotoxic lymphocytes, an action of improving a cell proliferation rate and an action of maintaining a cytotoxic activity by using fibronectin and a fragment thereof have been already studied by the present inventors (for example, Patent Publications 3, 4 and 5). However, considering the application for adoptive immunotherapy, the methods of the above-mentioned publications are not satisfactory at all, and a method for expanding lymphocytes with a further higher cell proliferation rate without using feeder cells from the viewpoint of safety has been desired.

Non-Patent Publication 1: authored by Greenberg, P. D., *Advances in Immunology*, 1991, 49, 281-355.
Non-Patent Publication 2: Reusser P. and three others, *Blood*, 1991, 78(5), 1373-1380
Non-Patent Publication 3: Riddell S. R. and four others, *J. Immunol.*, 1991, 146(8), 2795-2804
Non-Patent Publication 4: Riddell S. R. and one other, *J. Immunol. Methods*, 1990, 128(2), 189-201
Non-Patent Publication 5: Ho M. and nine others, *Blood*, 1993, 81(8), 2093-2101
Non-Patent Publication 6: Rosenberg S. A. et al., *N. Engl. J. Med.* 1987, 316(15), 889-897
Non-Patent Publication 7: Rosenberg S. A. et al., *N. Engl. J. Med.*, 1988, 319(25), 1676-1680
Non-Patent Publication 8: authored by Deane F. Mosher, published in 1989, *FIBRONECTIN*, ACADEMIC PRESS INC., 1-24.
Non-Patent Publication 9: Kimizuka F. and eight others, *J. Biochem.*, 1991, 110(2), 284-291
Non-Patent Publication 10: Hanenberg H. and five others, *Human Gene Therapy*, 1997, 8(18), 2193-2206
Patent Publication 1: WO 96/06929
Patent Publication 2: WO 97/32970
Patent Publication 3: WO 03/016511
Patent Publication 4: WO 03/080817
Patent Publication 5: WO 2005/019450

SUMMARY OF THE INVENTION

A first invention of the present invention relates to a method for preparing lymphocytes, characterized in that the method includes the step of culturing in the presence of polypeptide (X) and/or polypeptide (Y) described below. The above polypeptide (X) contains in the sequence two or more amino acid sequences (m) and one or more amino acid sequences (n), wherein the amino acid sequence (m) consists of one amino acid sequence selected from SEQ ID NOs: 1 to 3 of Sequence Listing, or an amino acid sequence where several amino acid sequences selected from SEQ ID NOs: 1 to 3 of Sequence Listing that are directly or indirectly connected to each other, and the amino acid sequence (n) consists of an amino acid sequence shown in SEQ ID NO: 4 of Sequence Listing, with proviso that the above amino acid sequence (m) does not contain two or more sequences that are identical to each other, among the sequences shown in SEQ ID NOs: 1 to 3 of Sequence Listing, and each of two or more amino acid sequences (m) in the polypeptide (X) is identical. In addition, the above polypeptide (Y) is a polypeptide containing an amino acid sequence having substitution, deletion, insertion or addition of one or several amino acids in at least one of any amino acid sequences selected from SEQ ID NOs: 1 to 3 of Sequence Listing and the amino acid sequence shown in SEQ ID NO: 4 of Sequence Listing, contained in the above polypeptide (X), wherein the polypeptide has a function equivalent to the above polypeptide (X). In the first invention of the present invention, the polypeptide (X) is exemplified by a polypeptide having a sequence containing two or three amino acid sequences (m) and a polypeptide having a sequence containing two or three amino acid sequences (n). Specific example of the polypeptide (X) includes polypeptides having the amino acid sequences shown in SEQ ID NO: 5, 16, 19, 22, 25, 27, 29, 32, 36, 39, 41, 47 and 49 of Sequence Listing. In addition, in the first invention of the present invention, the lymphocytes are exemplified by antigen-specific cytotoxic T lymphocytes and lymphokine-activated cells.

In addition, in the first invention of the present invention, a method for preparing lymphocytes, further including the step of transducing a foreign gene into the lymphocytes is provided. A method for transducing the foreign gene is exemplified by a method of transducing using a retroviral vector, an adenoviral vector, an adeno-associated viral vector, a lentiviral vector or a simian viral vector. In the first invention of the present invention, a CD3 ligand is exemplified by an anti-CD3 antibody, and a CD28 ligand is exemplified by an anti-CD28 antibody.

A second invention of the present invention relates to lymphocytes obtained by the first invention of the present invention. In addition, a third invention of the present invention relates to a medicament containing the second invention of the present invention as an effective ingredient.

A fourth invention of the present invention relates to a polypeptide selected from (a) and (b) described below. The polypeptide represented by (a) is a polypeptide having an amino acid sequence selected from the group consisting of SEQ ID NOs: 5, 16, 19, 22, 25, 27, 29, 32, 36, 39, 41, 47 and 49 of Sequence Listing, and the polypeptide represented by (b) is a polypeptide having an amino acid sequence having deletion, insertion, addition or substitution of one or several amino acids in the amino acid sequence of the above polypeptide (a).

A fifth invention of the present invention relates to a nucleic acid selected from (c) to (g) described below. The nucleic acid represented by (c) encodes a polypeptide having an amino acid sequence selected from the group consisting of SEQ ID NOs: 5, 16, 19, 22, 25, 27, 29, 32, 36, 39, 41, 47 and 49 of Sequence Listing; the nucleic acid represented by (d) encodes a polypeptide having an amino acid sequence having deletion, insertion, addition or substitution of one or several amino acids in the amino acid sequence selected from the group consisting of SEQ ID NOs: 5, 16, 19, 22, 25, 27, 29, 32, 36, 39, 41, 47 and 49 of Sequence Listing, the polypeptide having a function equivalent to the polypeptide having an amino acid sequence selected from SEQ ID NOs: 5, 16, 19, 22, 25, 27, 29, 32, 36, 39, 41, 47 and 49 of Sequence Listing; the nucleic acid represented by (e) consists of a nucleotide sequence selected from SEQ ID NOs: 6, 17, 20, 23, 26, 28, 30, 33, 37, 40, 42, 48 and 50 of Sequence Listing; the nucleic acid represented by (f) is a nucleic acid which hybridizes to the above nucleic acid (e) under stringent conditions, wherein the polypeptide encoded by the nucleic acid has a function equivalent to the polypeptide encoded by the above nucleic acid (e); and the nucleic acid represented by (g) is a nucleic acid resulting from one or more substitutions, deletions, insertions or additions of one or several bases in the nucleotide sequence of the above nucleic acid (e), wherein the polypeptide encoded by the nucleic acid has a function equivalent to the polypeptide encoded by the above nucleic acid (e).

BRIEF DESCRIPTION OF THE DRAWINGS

FIG. 1 A schematic view showing a domain structure of fibronectin.

FIG. 2 A chart showing a method for preparing H296-H296.

DETAILED DESCRIPTION OF THE INVENTION

The present invention relates to an effective method for preparing lymphocytes, which is suitably used in the field of medicine.

In the present invention, it has been found that lymphocytes having a high expansion fold and also a high cytotoxic activity are obtained by including the step of culturing lymphocytes in the presence of a modified recombinant fibronectin fragment, in which a part of a heparin binding domain of fibronectin overlaps, and the present invention has been completed thereby.

According to the present invention, a method for preparing lymphocytes is provided. The method of the present invention gives a high cell proliferation rate and the lymphocytes obtained by the present invention are suitably used, for example, in adoptive immunotherapy. Accordingly, a significant contribution to the field of medicine is expected by the method of the present invention. In addition, according to the present invention, a novel modified recombinant fibronectin fragment is provided.

The present invention will be concretely explained hereinafter.

(1) Polypeptide (X) or Polypeptide (Y) Used in Present Invention

The polypeptide (X) described herein is a polypeptide containing two or more amino acid sequences (m) and one or more amino acid sequences (n) as essential regions.

The amino acid sequence (m) is an amino acid sequence consisting of one or a plural number of amino acid sequences selected from SEQ ID NOs: 1 to 3 which are parts of a heparin binding domain of the fibronectin, with proviso that the amino acid sequence (m) is an amino acid sequence which does not contain two or more of each identical sequence shown in SEQ ID NOs: 1 to 3 of Sequence Listing, or an amino acid sequence constituted by the combination of the amino acid sequences shown in SEQ ID NOs: 1 to 3 of Sequence Listing. For example, the amino acid sequence (m) does not contain two or more amino acid sequences shown in SEQ ID NO: 1 of Sequence Listing, and the same is true on the amino acid sequence shown in SEQ ID NO: 2 or 3 of Sequence Listing. In addition, each of two or more amino acid sequences (m) existing in the polypeptide (X) show the identical amino acid sequence. Here, the amino acid sequences shown in SEQ ID NOs: 1 to 3 of Sequence Listing show partial amino acid sequences of the heparin binding domain of the fibronectin, and each of the amino acid sequences is an amino acid sequence of III-12, III-13 or III-14 (see FIG. 1).

As the amino acid sequence (m), those in which a polypeptide comprising the amino acid sequences has a heparin binding activity can be preferably used. The heparin binding activity can be evaluated by assaying binding of the polypeptide comprising the amino acid sequence (m) to heparin using a known method. For example, utilizing a method of determining the cell adhesion activity of Williams D. A., et al. [*Nature*, 352, 438-441 (1991)], the binding of the polypeptide comprising the amino acid sequence (m) to heparin can be evaluated by using heparin, for example, a labeled heparin in place of the cell.

It is preferable that the polypeptide (X) contains, for example, 2 to 5 amino acid sequences (m), preferably 2 to 4 amino acid sequences (m), and more preferably 2 to 3 amino acid sequences (m).

The amino acid sequence (n) is an amino acid sequence shown in SEQ ID NO: 4 of Sequence Listing, which is CS-1 domain of the fibronectin. It is preferable that the polypeptide (X) contains, for example, 1 to 5 amino acid sequences (n), preferably 1 to 4 amino acid sequences (n), and more preferably 1 to 3 amino acid sequences (n). It is preferable that the polypeptide (X) preferably contains the same number of the amino acid sequence (n) as the amino acid sequence (m) contained in the polypeptide (X).

As described above, the polypeptide (X) is a polypeptide containing two or more amino acid sequences (m) and one or more amino acid sequences (n), and any two or more amino acid sequences (m) in the polypeptide (X) are the identical sequences. Other amino acid residues may be contained, so long as the desired effects of the present invention are obtained. For example, amino acid residues from methionine, His-tag sequence, linker and the like may be contained.

The positional relation between two or more amino acid sequences (m) and one or more amino acid sequences (n) in the polypeptide (X) is not particularly limited, so long as the desired effects of the present invention are obtained. For example, one that the amino acid sequence (n) is connected to at least one amino acid sequence (m) at a C-terminal side is preferable. In addition, it is preferable that the amino acid sequence (m) is located at an N-terminal side, and the amino acid sequence (n) is located at a C-terminal side, of the polypeptide (X). More preferably, it is preferable that the amino acid sequence (m) and the amino acid sequence (n) are alternately located in the polypeptide (X).

In the present invention, the polypeptide (X) is exemplified by, for example, a polypeptide consisting of the amino acid sequence shown in SEQ ID NO: 5 of Sequence Listing (H296-H296), a polypeptide consisting of the amino acid sequence shown in SEQ ID NO: 16 of Sequence Listing (H296-H296-HT), a polypeptide consisting of the amino acid sequence shown in SEQ ID NO: 19 of Sequence Listing (CH296-CH296-HT), a polypeptide consisting of the amino acid sequence shown in SEQ ID NO: 22 of Sequence Listing (H105-H105-HT), a polypeptide consisting of the amino acid sequence shown in SEQ ID NO: 25 of Sequence Listing (H296-H296-HT), a polypeptide consisting of the amino acid sequence shown in SEQ ID NO: 27 of Sequence Listing (H296-H296-H296), a polypeptide consisting of the amino acid sequence shown in SEQ ID NO: 29 of Sequence Listing (H105-H105), a polypeptide consisting of the amino acid sequence shown in SEQ ID NO: 32 of Sequence Listing (H271-H296), a polypeptide consisting of the amino acid sequence shown in SEQ ID NO: 36 of Sequence Listing (H296-H271), a polypeptide consisting of the amino acid sequence shown in SEQ ID NO: 39 of Sequence Listing (15aaH105-H105-HT), a polypeptide consisting of the amino acid sequence shown in SEQ ID NO: 41 of Sequence Listing (15aaH105-H105), a polypeptide consisting of the amino acid sequence shown in SEQ ID NO: 47 of Sequence Listing (H105-H105Nc-HT), and a polypeptide consisting of the amino acid sequence shown in SEQ ID NO: 49 of Sequence Listing (H105-H105Nc).

H296-H296 is a polypeptide constituted by III-12, III-13, III-14, CS-1, alanine, methionine, III-12, III-13, III-14, and CS-1, in the order from an N-terminal side.

H296-H296-H296-HT is a polypeptide constituted by His-tag sequence (MNHKVHHHHHHIEGRH)(SEQ ID NO: 53), methionine, III-12, III-13, III-14, CS-1, histidine, methionine, III-12, III-13, III-14, CS-1, histidine, methionine, III-12, III-13, III-14, and CS-1, in the order from an N-terminal side.

CH296-CH296-HT is a polypeptide constituted by His-tag sequence (MNHKVHHHHHHIEGRH)(SEQ ID NO: 53), methionine, III-8, III-9, III-10, aspartic acid, lysine, proline, serine, methionine, III-12, III-13, III-14, CS-1, histidine, methionine, III-8, III-9, III-10, aspartic acid, lysine, proline, serine, methionine, III-12, III-13, III-14, and CS-1, in the order from an N-terminal side.

H105-H105-HT is a polypeptide constituted by His-tag sequence (MNHKVHHHHHHIEGRH)(SEQ ID NO: 53), methionine, III-14, CS-1, histidine, methionine, III-14, and CS-1, in the order from an N-terminal side.

H296-H296-HT is a polypeptide constituted by His-tag sequence (MNHKVHHHHHHIEGRH)(SEQ ID NO: 53), methionine, III-12, III-13, III-14, CS-1, histidine, methionine, III-12, III-13, III-14, and CS-1, in the order from an N-terminal side.

H296-H296-H296 is a polypeptide obtained by removing His-tag sequence at an N-terminal side of H296-H296-H296-HT, and can be prepared by cutting His-tag sequence from H296-H296-H296-HT according to a known method.

H105-H105 is a polypeptide obtained by removing His-tag sequence at an N-terminal side of H105-H105-HT, and can be prepared by cutting His-tag sequence from H105-H105-HT according to a known method.

H271-H296 is a polypeptide constituted by III-12, III-13, III-14, alanine, methionine, III-12, III-13, III-14, and CS-1, in the order from an N-terminal side.

H296-H271 is a polypeptide constituted by III-12, III-13, III-14, CS-1, alanine, methionine, III-12, III-13, and III-14, in the order from an N-terminal side.

15aaH105-H105-HT is a polypeptide constituted by His-tag sequence (MNHKVHHHHHHIEGRH)(SEQ ID NO: 53), methionine, 15 amino acids at a C-terminal side of III-13, II-14, CS-1, alanine, methionine, alanine, III-14, and CS-1, in the order from an N-terminal side.

15aaH105-H105 is a polypeptide obtained by removing His-tag sequence at an N-terminal side of 15aaH105-H105-HT, and can be prepared by cutting His-tag sequence from 15aaH105-H105-HT according to a known method.

H105-H105Nc-HT is a polypeptide constituted by His-tag sequence (MNHKVHHHHHHIEGRH)(SEQ ID NO: 53), methionine, III-14, CS-1, alanine, methionine, alanine, III-14, and CS-1, in the order from an N-terminal side. Incidentally, the polypeptide is different only in 2 amino acids at a linker moiety contained between CS-1 and III-14, as compared to the above-mentioned H105-H105-HT.

H105-H105Nc is a polypeptide obtained by removing His-tag sequence at an N-terminal side of H105-H105Nc-HT, and can be prepared by cutting His-tag sequence from H105-H105Nc-HT according to a known method. Incidentally, the polypeptide is different only in 2 amino acids at a linker moiety contained between CS-1 and III-14, as compared to the above-mentioned H105-H105.

Incidentally, these polypeptides are novel polypeptides prepared for the first time in the present invention. The detail such as a method for preparing these polypeptides is described in "(4) Modified Fibronectin Polypeptide" described later.

As the useful information relating to the preparation of the polypeptide (X), the information relating to fibronectin can be referred to Kimiduka F., et al. [*J. Biochem.*, 110, 284-291 (1991)], Komblihtt A. R., et al. [*EMBO J.*, 4(7), 1755-1759 (1985)], Sekiguchi K., et al. [*Biochemistry*, 25(17), 4936-4941 (1986)], and the like. In addition, the nucleic acid sequence encoding fibronectin or the amino acid sequence of fibronectin is disclosed in GenBank Accession No. NM_002026 and NP_002017.

The polypeptide (Y) described in the present specification is a polypeptide (Y) containing an amino acid sequence having substitution, deletion, insertion or addition of one or a plural number of amino acids in at least one of any amino acid sequences selected from SEQ ID NOs: 1 to 3 of Sequence Listing and the amino acid sequence shown in SEQ ID NO: 4 of Sequence Listing, contained in the above polypeptide (X), wherein the polypeptide has a function equivalent to the above polypeptide (X). In other words, the polypeptide (Y) is a polypeptide having substitution, deletion, insertion or addition of an amino acid in the amino acid sequence (m) or the amino acid sequence (n), which is the essential component of the above polypeptide (X), and is not a polypeptide having substitution, deletion, insertion or addition of an amino acid in any amino acid sequence other than these amino acid sequences (m) and (n). The substitution, deletion, insertion or addition is exemplified by, for example, those resulting from one or more substitutions, deletions, insertions or additions of 1 to 20 amino acids, and even more preferably those resulting from one or more substitutions, deletions, insertions or additions of 1 to 5 amino acids.

It is preferable that the substitution or the like of an amino acid is carried out to an extent that it can change physico-chemical characteristics and the like of the polypeptide (X) within the range that the inherent function of the polypeptide (X) can be maintained. For example, it is preferable that the substitution or the like of an amino acid is conservative, within the range that the characteristics inherently owned by the polypeptide (X) (for example, hydrophobicity, hydrophilicity, electric charge, pK and the like) are not substantially changed. Specifically, it is preferable that the substitution of an amino acid is a substitution within each of the groups of: 1. glycine, alanine; 2 valine, isoleucine, leucine; 3. aspartic acid, glutamic acid, asparagine, glutamine; 4. serine, threonine; 5. lysine, arginine; 6. phenylalanine, tyrosine, and that deletion, addition or insertion of amino acids is deletion, addition or insertion of an amino acid having characteristics similar to the characteristics of the surroundings of the subject site in the polypeptide (X) within the range that would not substantially change the characteristics of the surroundings of the subject site.

The substitution or the like of an amino acid may be those naturally occurring caused by a difference between species or individuals, or may be those artificially induced. Artificial induction may be carried out by a known method and is not particularly limited. For example, in accordance with a known method, a given nucleic acid having substitution, deletion, addition or insertion of one or a plural number of bases in the nucleic acid encoding the above-mentioned polypeptide (X) is prepared, whereby the polypeptide (Y) containing an amino acid sequence having substitution or the like in the amino acid sequence of the polypeptide (X) can be prepared. In addition, when the above-mentioned polypeptide (X) is obtained in a genetic engineering manner, in a case where, for example, the polypeptide is prepared using *Escherichia coli* or the like as a host, methionine at an N-terminal side sometimes does not exist by the effect of methionine peptidase derived from *Escherichia coli* or the like, and the polypeptide as mentioned above is also shown as the preferred example of the polypeptide (Y) in the present invention.

The polypeptide (Y) of the present invention is exemplified by a polypeptide containing an amino acid sequence having substitution, deletion, insertion or addition of one or a plural number of amino acids in at least one of any amino acid sequences selected from SEQ ID NOs: 1 to 3 of Sequence Listing and the amino acid sequence shown in SEQ ID NO: 4 of Sequence Listing, preferably contained in H296-H296, H296-H296-H296-HT, CH296-CH296-HT, H105-H105-HT, H296-H296-HT, H296-H296-H296, H105-H105, H271-H296, H296-H271, 15aaH105-H105-HT, 15aaH105-H105, H105-H105Nc-HT, or H105-H105Nc as described above, wherein the polypeptide has a function equivalent to the above H296-H296, H296-H296-H296-HT, CH296-CH296-HT, H105-H105-HT, H296-H296-HT, H296-H296-H296, H105-H105, H271-H296, H296-H271, 15aaH105-H105-HT, 15aaH105-H105, H105-H105Nc-HT, or H105-H105Nc. The polypeptide (Y) is exemplified by a polypeptide resulting from one or more substitutions, deletions, insertions or additions of preferably 1 to 20 amino acids, and even more preferably 1 to 5 amino acids.

In addition, the phrase "having a function equivalent" herein refers to that, when the preparation of lymphocytes set forth below is carried out using the polypeptide (X) which is a comparative control, the equivalent cell proliferation rate is obtained, or the equivalent cytotoxic activity is maintained. In other words, the preparation of lymphocytes is carried out in accordance with the method for preparing lymphocytes set forth below, especially, the methods described in Examples 2 to 21, 25 to 33, 42 to 44, 47 to 51, 54 to 60, and 64 to 66 set forth below, whereby its function can be appropriately confirmed. In addition, as the polypeptide (Y), a polypeptide having a heparin binding activity is preferred. The heparin binding activity can be evaluated in accordance with the above-mentioned method for assaying the activity. Each of the polypeptide (X) and the polypeptide (Y) can be used in the method for preparing lymphocytes set forth below alone or in admixture of plural kinds.

The polypeptide (X) and polypeptide (Y) used in the present invention have a clearly high cell proliferation rate, as compared to known fibronectin fragments, CH-296 (polypeptide containing a cell binding domain, a heparin binding domain and CS-1 domain of the fibronectin) and H-296 (polypeptide containing a heparin binding domain and CS-1 domain of the fibronectin), in the method for preparing lymphocytes of the present invention set forth below, and when the polypeptide (X) and the polypeptide (Y) are used in the preparation of antigen-specific CTLs in the present invention, a high cytotoxic activity can be maintained, as described in Examples 9 to 15, and 36 to 38 set forth below. Therefore, when these polypeptides are used, there are very useful advantages, as compared to a case where a known fibronectin fragment is used. Incidentally, one of the factors that the polypeptide used in the present invention exhibits very useful effects mentioned above includes that these polypeptides have a very high immobilization efficiency to a solid phase such as a cell culture equipment, as shown in Example 35 and Example 61 set forth below. However, as shown in Examples 36 to 38 set forth below, even when the amount immobilized to the cell culture equipment was matched, the polypeptide used in the present invention exhibits a very high effect, as compared to a known fibronectin fragment. For example, even when lymphocytes are prepared by the method of the present invention using H296-H296 and H-296 in twice the amount thereof in molar conversion, lymphocytes prepared using H296-H296 exhibit a clearly higher effect. In view of the above, it is shown that the effects of the polypeptide (X) or (Y) used in the present invention on the preparation of the lymphocytes is not only a simple additive effect exhibited by a high immobilization efficiency and duplication of domain of the fibronectin fragment. Further, the polypeptide (X) or (Y) is used for expansion of antigen-specific CTLs, whereby maintenances of a high cell proliferation rate and cytotoxic activity can be realized without using feeder cells, as shown in (2)-1-3 set forth below. Avoiding the use of feeder cells on expansion of antigen-specific CTLs is very creative from the aspects of safety, procedure of cell culture and its cost, and a burden on a donor of the feeder cells or a patient, but it has been unable to be realized in the conventional expansion of antigen-specific CTLs. Also in this regard, the method of the present invention is a very useful method, which is not predictable from the preparation of lymphocytes using the conventional fibronectin fragment.

The number of the amino acids constituting these polypeptide (X) or polypeptide (Y) is not particularly limited, and is preferably from 100 to 3000 amino acids, more preferably from 150 to 2800 amino acids, and even more preferably from 200 to 2600 amino acids.

(2) Method for Preparing Lymphocytes

The method for preparing lymphocytes of the present invention will be concretely explained hereinafter. The method of the present invention is a method for preparing lymphocytes characterized in that the method includes the step of culturing in the presence of the above-mentioned polypeptide (X) and/or polypeptide (Y) (which may be hereinafter referred to as step of culturing of the present invention). Here, in the specification of the present application, the polypeptide (X) and/or polypeptide (Y) may be referred to as the effective ingredient in the present invention.

The method for preparing lymphocytes of the present invention is carried out by the step of culturing of the present invention during the entire period of the culture in the preparation of lymphocytes, or during any partial period. In other words, the present invention encompasses those embodiments which include the above-mentioned step of culturing in a part of the steps of preparing lymphocytes. When the above-mentioned step of culturing is included in a part of the steps of preparing lymphocytes, it is preferable that the above-mentioned step of culturing is included preferably in an early stage of the culture, and it is preferable that the above-mentioned step of culturing is included more preferably at the initiation of the culture.

The lymphocytes obtained by the method of the present invention are not particularly limited, and include, for example, cytotoxic T lymphocytes (CTLs), helper T cells, lymphokine-activated cells, tumor-infiltrating lymphocytes (TILs), NK cells, naive cells, memory cells, γδT cells, NKT cells, and a cell population containing at least one kind of the above-mentioned cells, and the like. Among them, the present invention is more suitable for the preparation of antigen-specific CTLs and lymphokine-activated cells. The methods for preparing these cells are specifically described in (2)-1 and (2)-2 set forth below. Here, the lymphokine-activated cells herein refer to a functional cell population, which is obtained by adding IL-2 to peripheral blood (peripheral blood leukocyte), umbilical cord blood, tissue fluid or the like containing lymphocytes, and culturing the cells for several days. The above-mentioned cell population may be generally referred to as the lymphokine-activated killer cells (LAK cells). Since the cell population also contains a cell which does not have a cytotoxicity (for example, naive cell, and the like), the cell population is referred to as the lymphokine-activated cells in the specification of the present application.

Incidentally, the cytotoxic activity of the lymphocytes obtained by the method of the present invention can be assessed by a known method. For example, the cytotoxic activity of the cytotoxic lymphocytes to a target cell labeled with a radioactive substance, a fluorescent substance or the like can be assessed by determining radioactivity or fluorescence intensity from the target cell destroyed by the cytotoxic lymphocytes. The cytotoxic activity can also be detected by determining the amount of cytokine such as GM-CSF or IFN-γ specifically released from cytotoxic lymphocytes or the target cell. In addition, the cytotoxic activity can also be directly confirmed by use of an antigenic peptide-MHC complex labeled with a fluorescent dye or the like. In this case, the cytotoxic activity of the cytotoxic lymphocytes can be assessed, for example, by contacting cytotoxic lymphocytes with a first fluorescent marker coupled with a cytotoxic lymphocyte-specific antibody, followed by contacting with an antigenic peptide-MHC complex coupled with a second fluorescent marker, and analyzing the presence of double-labeled cell with flow cytometry.

The step of culturing in the present invention is purposed for induction of antigen-specific CTLs from cells capable of being formed into CTLs, maintenance of antigen-specific CTLs, or expansion of the above-mentioned lymphocytes such as antigen-specific CTLs or naive cells. In the method for preparing lymphocytes of the present invention, the kind of cells subjected to the method, conditions for culture and the like are appropriately adjusted, to carry out the culture of lymphocytes, whereby lymphocytes useful for adoptive immunotherapy and the like can be prepared. Here, it is defined herein that the "lymphocytes" also encompass a group of cells containing a lymphocyte, and that the "CTLs" also encompass a group of cells containing a CTL. The cell used in the culture can be properly set depending upon the kinds of the lymphocytes prepared. The cells which are collected from a living body can be directly used or those which have been subjected to frozen storage can be used.

As the cell culture equipment used in the step of culturing in the present invention, for example, without particular limitation, a petri dish, a flask, a bag, a large scale fermenter (jar fermenter), a bioreactor and the like can be used. Here, as a bag, for example, a $CO_2$ gas-permeable bag for cell culture can be used. In addition, upon industrial preparation of a large amount of lymphocytes, a large scale fermenter (jar fermenter) can be used. Furthermore, the culture can be carried out in either open system or closed system. It is preferable that the culture is carried out preferably in closed system, from the viewpoint of safety of the resulting lymphocytes.

In the present invention, the phrase "in the presence of the above-mentioned effective ingredient" refers to that, when the culture of lymphocytes is carried out, the above-mentioned effective ingredient is present in a state that the ingredient can exhibit its functions, and an existing manner of the effective ingredient is not particularly limited. For example, when the effective ingredient is dissolved in the medium to be used, the amount of the effective ingredient in the present invention contained in the medium where the culture is carried out is not particularly limited, so long as the desired effects are obtained. For example, the effective ingredient is contained in an amount of preferably from 0.0001 to 10000 μg/mL, more preferably from 0.001 to 10000 μg/mL, even more preferably 0.005 to 5000 μg/mL, and even more preferably from 0.01 to 1000 μg/mL.

The components used in the medium, containing the effective ingredient in the present invention (for example, anti-CD3 antibody, anti-CD28 antibody, interleukin-2, or the like) may be dissolved in the medium to be co-present, or may be immobilized to an appropriate solid phase, for example, a cell culture equipment (including any of those of an open system and a closed system), such as a petri dish, a flask or a bag, or to a cell culture carrier such as beads, a membrane or a slide glass, and used. The materials for those solid phases are not particularly limited, so long as the materials can be used for cell culture. When the components are immobilized to, for example, the above-mentioned equipment, it is preferable to immobilize a given amount of each component based on the amount of the medium to be placed in the equipment so that, upon placing the medium in the equipment, the medium is contained in a proportion similar to that of a desired concentration in the case where the components are dissolved in the medium and used. The amount of the components immobilized is not particularly limited, so long as the desired effects can be obtained. The above-mentioned carrier is used by immersing the carrier in a culture medium in the cell culture equipment during the cell culture. When the above-mentioned components are immobilized to the above-mentioned carrier, it is preferable to immobilize a given amount of each component based on the amount of the medium placed in the equipment, so that the medium is contained in a proportion similar to that of a desired concentration upon placing the carrier in the medium, in the case where the components are dissolved in the medium and used. The amount of the components immobilized is not particularly limited, so long as the desired effects can be obtained.

For example, the immobilization of the polypeptide (X) and/or the polypeptide (Y) can be carried out in the same manner as in the immobilization of the fibronectin fragment described in WO 97/18318 and WO 00/09168. Once various components mentioned above or the effective ingredient in the present invention is immobilized to the solid phase, the lymphocytes are obtained by the method of the present invention, and thereafter the lymphocytes can be easily separated from the effective ingredient in the present invention simply by separating the lymphocytes from the solid phase, so that the contamination of the effective ingredient or the like into the lymphocytes can be prevented.

The culture may be carried out under the known conditions for culturing lymphocytes, and the conditions used for the usual cell culture can be employed. For example, cells can be cultured under the conditions of 37° C. in the presence of 5% $CO_2$ and the like. In addition, the medium can be diluted by adding a fresh medium to the cell culture medium, the medium can be exchanged with a fresh one, or the cell culture equipment can be exchanged at appropriate intervals. The medium used, other components simultaneously used and the like can be properly set depending upon the kinds of the lymphocytes prepared, as described below.

In addition, there may be cultured using together with the above-mentioned components the fibronectin described in WO 03/080817 or a known fibronectin fragment. As the known fibronectin fragments, H-296 and CH-296 described in Preparation Examples 1 and 2 set forth below can be preferably used.

Furthermore, there may be cultured using together with the above-mentioned components a compound selected from the group consisting of acidic polysaccharides, acidic oligosaccharides, acidic monosaccharides and salts thereof which are effective for induction of cytotoxic T cells having an antigen-specific cytotoxic activity, described in WO 02/14481, or a substance selected from the following (A) to (D) described in WO 03/016511:

(A) a substance having a binding activity to CD44;
(B) a substance capable of regulating a signal emitted by binding of a CD44 ligand to CD44;
(C) a substance capable of inhibiting binding of a growth factor to a growth factor receptor; and
(D) a substance capable of regulating a signal emitted by binding of a growth factor to a growth factor receptor.

The above-mentioned substance having a binding activity to CD44 is exemplified by, for example, a CD44 ligand and/or an anti-CD44 antibody. The substance capable of regulating a signal emitted by binding of a CD44 ligand to CD44 includes, for example, various inhibitors or activators for kinase and phosphatase. The substance capable of inhibiting binding of a growth factor to a growth factor receptor includes, for example, a substance having a binding activity to a growth factor and forming a complex with the growth factor, thereby inhibiting the binding of the growth factor to a growth factor receptor, or a substance having a binding activity to a growth factor receptor, thereby inhibiting the binding of the growth factor to a growth factor receptor. Furthermore, the substance capable of regulating a signal emitted by binding of a growth factor to a growth factor receptor includes, for example, various inhibitors or activators for kinase and phosphatase. The concentration of these components in the medium is not particularly limited, so long as the desired effects can be obtained. Also, these components may be dissolved in a medium to be co-present, or may be immobilized to an appropriate solid phase mentioned above, and used. Here, each of various substances mentioned above can be used alone or in admixture of two or more kinds.

As the medium used in the step of culturing lymphocytes in the present invention, a known medium used for cell culture may be used, and various cytokines or the like may be further added depending upon the kinds of lymphocytes prepared as described below.

In the step of culturing lymphocytes in the present invention, serum and plasma can be also added to a medium. The amounts of serum and plasma added to a medium are not particularly limited, and are preferably from 0 to 20% by volume. Especially when autologous serum or plasma is used, the amount is preferably from 0 to 5% by volume, in consideration of a burden on a patient. In addition, in the step of culturing lymphocytes, the concentration of serum and plasma in the medium can be stepwise decreased. For example, when a medium is exchanged or added in the step of culturing lymphocytes, the concentration of serum or plasma in a new medium is adjusted to a low level, whereby the culture of lymphocytes can be carried out with decreasing the plasma or plasma used. It is one of the advantageous effects of the present invention that the amounts of serum and plasma added to a medium can be decreased as described above. Incidentally, origin of the serum or plasma may be either autologous (meaning that the origin is the same as that of the lymphocytes cultured) or nonautologous (meaning that the origin is different from that of the lymphocytes cultured). Preferably, autologous serum or plasma can be used, from the viewpoint of safety.

For example, in the method of the present invention, when the expansion of lymphocytes is carried out, the number of cells at the initiation of culture used in the present invention is not particularly limited. For example, the number of cells is exemplified by, for example, from 1 cell/mL to $1\times10^8$ cells/mL, preferably from 1 cell/mL to $5\times10^7$ cells/mL, and more preferably from 1 cell/mL to $2\times10^7$ cells/mL.

(2)-1 Method for Preparing Antigen-Specific CTLs

An example of preparing antigen-specific CTLs according to the method of the present invention (which may be hereinafter referred to as the method for preparing antigen-specific CTLs in the present invention) will be described in detail hereinafter.

When antigen-specific CTLs are prepared by the method of the present invention, the step of culturing in the present invention can be carried out in a culture for inducing antigen-specific CTLs from cells capable of being formed into CTLs (method for inducing antigen-specific CTLs in the present invention), a culture for maintaining antigen-specific CTLs (method for maintaining antigen-specific CTLs in the present invention), or a culture for expanding antigen-specific CTLs (method for expanding antigen-specific CTLs in the present invention).

(2)-1-1 Method for Inducing Antigen-Specific CTLs of Present Invention

An embodiment of the step of culturing lymphocytes in the present invention for inducing antigen-specific CTLs will be explained. The induction of antigen-specific CTLs is carried out by culturing cells capable of being formed into CTLs together with an appropriate antigen-presenting cell or antigen, in order to give the cells capable of being formed into CTLs an ability to recognize the desired antigen.

The cells capable of being formed into CTLs are exemplified by peripheral blood mononuclear cells (PBMCs), naive cells, memory cells, umbilical cord blood mononuclear cells, hemopoietic stem cells, lymphokine-activated cells, and the like. Any of these cells which are collected from a living body can be used, or which are obtained via culture ex vivo, can be directly used or those which has been subjected to frozen storage can be used. The antigen-presenting cell is not particularly limited, so long as the cell is capable of presenting an antigen to be recognized to T cell. For example, monocyte, B cell, T cell, macrophage, dendritic cell, fibroblast or the like, which is allowed to present a desired antigen, and subjected to X-ray irradiation or the like to make deficient in the ability for proliferation as occasion demands, can be used in the present invention. The antigen is not particularly limited, and includes, for example, exogenous antigens such as bacteria and viruses, endogenous antigens such as tumor-associated antigens (cancer antigens), and the like. In addition, stimulation with an antigen-presenting cell can be carried out in several times during the culture period.

In addition, in the induction of antigen-specific CTLs, the medium may preferably contain appropriate proteins, cytokines, and other components in addition to the effective ingredient in the present invention. A medium containing interleukin-2 (which may be hereinafter referred to as IL-2) is preferably used in the present invention. The concentration of IL-2 in the medium is not particularly limited, and is, for example, preferably from 0.01 to $1\times10^5$ U/mL, and more preferably from 0.1 to $1\times10^4$ U/mL.

In addition, the general conditions for inducing antigen-specific CTLs may be set in accordance with the known conditions [Bednarek M. A. et al., *J. Immunology*, 147(12), 4047-4053, (1991)]. The culture conditions are not particularly limited, and the conditions which are used in ordinary cell culture can be employed. For example, the culture can be carried out under the conditions of 37° C. in the presence of 5% $CO_2$, and the like. This culture is usually carried out for about 2 to about 15 days. In addition, the step of diluting a cell culture medium, the step of exchanging the medium, or the step of exchanging a cell culture equipment may be carried out at appropriate intervals.

The antigen-specific CTLs are induced by carrying out the step of culturing in the present invention as mentioned above, whereby a cell proliferation rate after the induction of the antigen-specific CTLs is high, and upon further subjecting the induced antigen-specific CTLs to expansion, a very high cell proliferation rate can be realized. Further, the antigen-specific CTLs induced as described above are characterized in that a high cytotoxic activity as observed immediately after the induction is maintained even when CTLs are maintained over a long period of time or expanded. The above-mentioned maintenance and expansion can be carried out preferably according to the method for maintaining antigen-specific CTLs and the method for expanding antigen-specific CTLs, set forth below. Even when other known methods, in other words, maintenance and expansion of antigen-specific CTLs are carried out in the absence of the above-mentioned polypeptide (X) and/or polypeptide (Y), the resulting cells maintain the above-mentioned high cytotoxic activity, and a high cell proliferation rate is recognized. Regarding these effects, a significantly high effect is exhibited, for example, as compared to the results obtained by carrying out the induction of antigen-specific CTLs in the presence of H-296, a known fragment of fibronectin (see Examples 9 to 14 set forth below). Further, when the expansion is carried out using antigen-specific CTLs obtained by the method for inducing antigen-specific CTLs in the present invention, a high cell proliferation rate can be recognized without using feeder cells. In addition, for example, the antigen-specific CTLs induced are cloned, whereby the stable antigen-specific CTLs can be maintained.

(2)-1-2 Method for Maintaining Antigen-Specific CTLs of Present Invention

The method for maintaining antigen-specific CTLs in the present invention is a method for maintaining antigen-specific CTLs with keeping its cytotoxic activity. The method is characterized in that the step of culturing in the present invention described above is carried out upon the maintenance of the antigen-specific CTLs, whereby cytotoxic activity of the antigen-specific CTLs can be maintained.

The antigen-specific CTLs to which the above-mentioned method is applicable are not particularly limited, and the method is used for maintaining antigen-specific CTLs obtained by a known method, antigen-specific CTLs obtained by the method for inducing antigen-specific CTLs in the present invention described above, or antigen-specific CTLs obtained by the method for expanding antigen-specific CTLs set forth below. In addition, the antigen-specific CTLs as used herein mean a cell population that contains the antigen-specific CTLs.

The medium used is not particularly limited, and a known medium can be used. The medium may also contain appropriate proteins, cytokines (for example, IL-2), and other components, in the same manner as in the induction of antigen-specific CTLs as described above.

The general conditions for maintaining antigen-specific CTLs may be set in accordance with a known method [for example, Carter J. et al., *Immunology*, 57(1), 123-129, (1996)]. The culture conditions are not particularly limited, and the conditions which are used in ordinary cell culture can be employed. For example, the culture can be carried out under the conditions of 37° C. in the presence of 5% $CO_2$, and the like. The cultured days are not particularly limited. In addition, the step of diluting a cell culture medium, the step of exchanging a medium, or the step of exchanging a cell culture equipment may be carried out at appropriate intervals.

(2)-1-3 Method for Expanding Antigen-Specific CTLs of Present Invention

The method for expanding antigen-specific CTLs in the present invention is a method for rapidly expanding the number of cells of antigen-specific CTLs with keeping its cytotoxic activity. The method is characterized in that the step of culturing in the present invention described above is carried out upon the expansion of the antigen-specific CTLs. Here, the step of culturing in the present invention may be carried out during the entire period of the expansion, or during a part of the period. It is preferable that the step of culturing in the present invention is carried out preferably at the initiation of the culture. It is preferable that the cultured period of the step of culturing in the present invention is, for example, from 1 to 8 days, preferably from 2 to 7 days, more preferably from 3 to 7 days, and for 3 days or more from the viewpoint of realizing a higher expansion fold.

The antigen-specific CTLs to which the above-mentioned method is applicable are not particularly limited. For example, the antigen-specific CTLs obtained by a known method, the antigen-specific CTLs obtained by the method for inducing antigen-specific CTLs in the present invention described above, or the antigen-specific CTLs maintained according to the method for maintaining antigen-specific CTLs described above are used.

The medium used is not particularly limited, and a known medium can be used. The medium may also contain appropriate proteins, cytokines, and other components, for example, IL-2 or the like, in the same manner as in the induction of antigen-specific CTLs described above.

The general conditions for expanding antigen-specific CTLs may be set in accordance with a known method [for example, Carter J. et al., *Immunology*, 57(1), 123-129, (1996)].

In the method for expanding antigen-specific CTLs in the present invention, it is preferable that the cells are co-cultured with an anti-CD3 antibody, preferably with an anti-human CD3 monoclonal antibody, and more preferably with OKT3, in addition to the above-mentioned effective ingredient, from the viewpoint of realizing a high expansion fold. The concentration of the anti-CD3 antibody during culture is not particularly limited, and is, for example, from 0.001 to 100 µg/mL, and more preferably from 0.01 to 100 µg/ml. In addition, the cells can be further co-cultured with an anti-CD28 antibody, and more preferably with an anti-human CD28 monoclonal antibody, as co-stimulation. Also, a lymphocyte-stimulating factor such as lectin can be co-cultured. Furthermore, these components can be immobilized to an appropriate solid phase and used, as mentioned above.

In addition, in the method for expanding antigen-specific CTLs in the present invention, the cells can be co-cultured with appropriate feeder cells as occasion demands In the method for expanding antigen-specific CTLs, the feeder cells are not particularly limited, so long as the feeder cells stimulate CTLs cooperatively with the above-mentioned anti-CD3 antibody to activate T cell receptor or each of stimulation receptor. In the present invention, the feeder cells are not particularly limited, and autologous or nonautologous PBMCs and EBV-B cells are used. It is preferable to use cells other than EBV-B cells from the viewpoint of safety. Usually, feeder cells are used after their proliferating ability are taken away after subjecting the cells to an irradiation with X-rays or the like, or a treatment with an agent such as mitomycin. Incidentally, the content of the feeder cells in the medium may be determined according to a known method, and is not particularly limited. For example, the content is preferably from 1 to $1 \times 10^7$ cells/mL.

However, as described above, in the adoptive immunotherapy, it is preferable that feeder cells are not used, from the viewpoint of safety and the viewpoint of its cost, and a burden on a patient of the feeder cells or a patient. One of the great features of the method for expanding antigen-specific CTLs in the present invention also resides in that even when feeder cells are not used, a high expansion fold is realized. In other words, according to the present invention, there is provided a method for expanding antigen-specific CTLs without using feeder cells. Incidentally, when the antigen-specific CTLs are prepared without using feeder cells, it is desired that, as antigen-specific CTLs subjected to the expansion method in the present invention, antigen-specific CTLs obtained by the method for inducing antigen-specific CTLs in the present invention described above are used, from the viewpoint of realizing a high expansion fold.

(2)-2 Method for Preparing Lymphokine-Activated Cells

An example of preparing lymphokine-activated cells according to the method in the present invention (which may be hereinafter referred to the method for preparing lymphokine-activated cells in the present invention) will be described in detail hereinafter.

The method for preparing lymphokine-activated cells in the present invention is characterized in that the step of culturing in the present invention is carried out in the presence of IL-2 using cells capable of being formed into lymphokine-activated cells. The step of culturing in the present invention may be carried out during the entire period of the expansion, or during a part of the period. It is preferable that the step of culturing in the present invention is carried out preferably at the initiation of the culture. It is preferable that the cultured period of the step of culturing in the present invention is, for example, from 1 to 8 days, preferably from 2 to 7 days, more preferably from 3 to 7 days, and for 3 days or more, from the viewpoint of realizing a higher expansion fold.

The cells capable of being formed into lymphokine-activated cells are not particularly limited, and include, for example, peripheral blood mononuclear cells (PBMCs), NK cells, umbilical cord blood mononuclear cells, hemopoietic stem cells, blood components containing these cells, and the like, and cells can be used so long as the cells are hemocytes. In addition, a material containing the above-mentioned cells, for example, a blood such as peripheral blood or umbilical cord blood; one obtained by removing components such as erythrocyte and plasma from the blood; a marrow fluid and the like can be used.

In addition, the general conditions for culturing lymphokine-activated cells may be set in accordance with the known conditions [for example, see Saibo Kogaku (*Cell Technology*), 14(2), 223-227, (1995); Saibo Baiyo (*Cell Culture*), 17(6), 192-195, (1991); *THE LANCET*, 356, 802-807, (2000); *Current Protocols in Immunology*, supplement 17, UNIT 7.7]. The culture conditions are not particularly limited, and the conditions which are used in ordinary cell culture can be employed. For example, the culture can be carried out under the conditions of 37° C. in the presence of 5% $CO_2$, and the like. This culture is usually carried out for about 2 to about 15 days, and it is preferable that the step of culturing in the present invention is carried out in an early stage of the culture, as described above. In addition, the step of diluting a cell culture medium, the step of exchanging a medium, or the step of exchanging a cell culture equipment may be carried out at appropriate intervals.

The medium used is not particularly limited, and a known medium can be used. The medium may also contain appropriate proteins, cytokines, and other components, in the same manner as in the induction and expansion of antigen-specific CTLs described above.

In the method for preparing lymphokine-activated cells in the present invention, it is preferable that the cells are co-cultured with an anti-CD3 antibody, particularly preferably with an anti-human CD3 monoclonal antibody, and more preferably with OKT3, in addition to the above-mentioned effective ingredient, from the viewpoint of realizing a high expansion fold. The concentration of the anti-CD3 antibody in a medium is not particularly limited, and is, for example, from 0.001 to 100 μg/mL, and more preferably from 0.01 to 100 μg/ml. In addition, the cells can be further co-cultured with an anti-CD28 antibody, and particularly preferably with an anti-human CD28 monoclonal antibody, as co-stimulation. Also, the cells can be co-cultured with a lymphocyte-stimulating factor such as lectin. Furthermore, these components can be immobilized to an appropriate solid phase and used.

The cells obtained by the method for preparing lymphokine-activated cells in the present invention contain CD45RA-positive-CCR7-positive cells, CD45RA-positive-CD62L-positive cells, CD45RA-positive-CCR7-positive-CD62L-positive cells, CD27-positive cells and CD28-positive cells in a high ratio, as described in Examples 33, 43, 44, 47, and 54 to 56. In other words, the lymphokine-activated cells obtained by the method contain naive T-like cells in a high ratio, and are highly suitable for utilization for adoptive immunotherapy.

(2)-3 Method for Preparing Lymphocytes of Present Invention, Including Step of Transducing Foreign Gene The present invention also provides, in the above-mentioned method for preparing lymphocytes, a method for preparing lymphocytes, further including the step of transducing a foreign gene. In other words, one embodiment of the present invention provides a method for preparing lymphocytes, further including the step of transducing a foreign gene into the lymphocytes. Here, the term "foreign" refers to those which are foreign to lymphocytes into which a gene is to be transduced.

By carrying out the method for preparing lymphocytes of the present invention, particularly, the method for expanding lymphocytes, the ability for proliferation of the cultured lymphocytes is enhanced. Therefore, by combining the method for preparing lymphocytes of the present invention with the step of transducing a gene, increase in the gene-transducing efficiency is expected.

A means for transducing a foreign gene is not particularly limited, and an appropriate means can be selected from known methods for transducing a gene to be used. The step of transducing a gene can be carried out at any given point during the preparation of lymphocytes. For example, it is preferable to carry out the step during the cell proliferation in the method for expanding CTLs or method for preparing lymphokine-activated cells of the present invention described above.

As the above-mentioned method for transducing a gene, any of methods using a viral vector, and methods without using the vector can be employed in the present invention. The details of those methods have been already published in numerous literatures.

The above-mentioned viral vector is not particularly limited, and a known viral vector ordinarily used in the method for transducing a gene, for example, retroviral vector, lentiviral vector, adenoviral vector, adeno-associated viral vector, simian viral vector, vaccinia viral vector, sendai viral vector, or the like is used. Especially preferably, as the viral vector, retroviral vector, adenoviral vector, adeno-associated viral vector, lentiviral vector, or simian viral vector is used. As the above-mentioned viral vector, those lacking replication ability so that the viral vector cannot self-replicate in an infected cell are preferable. In addition, upon the gene transduction, a substance which improves transducing efficiency may be used, for example, RetroNectin (registered trademark, manufactured by TAKARA BIO INC.) and other fibronectin fragments can be also used.

The retroviral vector and lentiviral vector are used for the purpose of gene therapy or the like because the vectors can stably incorporate a foreign gene inserted therein into chromosomal DNA in the cell into which the vectors are to be transduced. Since the vectors have a high infection efficiency to the cell during mitosis and proliferation, the gene transduction is preferably carried out in the step of preparing lymphocytes, for example, in the step of expanding in the present invention.

As the method for transducing a gene without using a viral vector, for example, a method using a carrier such as liposome or ligand-polylysine, calcium phosphate method, electroporation method, particle gun method or the like can be used without limiting the present invention thereto. In this case, a foreign gene incorporated into a plasmid DNA or linear DNA is transduced.

The foreign gene to be transduced into lymphocytes in the present invention is not particularly limited, and any gene which is desired to be transduced into the above-mentioned cells can be selected. As the gene as described above, besides a gene encoding a protein (for example, enzymes, cytokines, receptors or the like), for example, a gene encoding an antisense nucleic acid, siRNA (small interfering RNA) or a ribozyme can be used. In addition, an appropriate marker gene which allows for selection of cells into which a gene is transduced may be simultaneously transduced.

The above-mentioned foreign gene can be, for example, inserted into a vector, a plasmid or the like, so as to be expressed under the control of an appropriate promoter, and used. In addition, in order to achieve an efficient transcription of a gene, there may exist in vector other regulating elements which cooperate with a promoter or a transcription initiation site, for example, an enhancer sequence or a terminator sequence. In addition, for the purpose of inserting a foreign gene into a chromosome of lymphocytes in which the gene is to be transduced by homologous recombination, for example, a foreign gene may be arranged between flanking sequences containing nucleotide sequences each having homology to nucleotide sequences located on both sides of the desired target insertion site of the gene in the chromosome. The foreign gene to be transduced may be one that is a naturally occurring or an artificially generated, or may be one in which DNA molecules having different origins from each other are bound by a known means such as ligation. Moreover, the foreign gene may be one having a sequence in which a mutation is introduced into a naturally occurring sequence depending upon its purpose.

According to the method of the present invention, for example, a gene encoding an enzyme associated with the resistance to a drug used for the treatment of a patient with cancer or the like can be transduced into lymphocytes, thereby giving the lymphocytes a drug resistance. If the lymphocytes as described above are used, adoptive immunotherapy and drug therapy can be combined, and therefore, higher therapeutic effects can be obtained. The drug resistance gene is exemplified by, for example, a multidrug resistance gene.

On the other hand, conversely to the above-mentioned embodiment, a gene to give sensitivity to a particular drug can be transduced into lymphocytes, thereby giving the lymphocytes sensitivity to the drug. In this case, the lymphocytes after being transplanted to a living body can be removed by administering the drug. The gene for giving sensitivity to a drug is exemplified by, for example, a thymidine kinase gene.

Other genes to be transduced are exemplified by a gene encoding a TCR recognizing a surface antigen of target cells and a gene encoding a chimeric receptor having an antigen-recognizing site of an antibody to the surface antigen of target cells and containing an intracellular region of TCR (CD3 or the like).

(3) Lymphocytes Obtained by Method of Present Invention, Medicament Containing Lymphocytes, Method for Treating Disease Using Medicament, and Medium for Culturing Lymphocytes Containing Effective Ingredient in Present Invention Further, the present invention provides lymphocytes obtained by the above-mentioned method of the present invention. In addition, the present invention provides a medicament (therapeutic agent) containing the lymphocytes as an effective ingredient. Particularly, the above-mentioned therapeutic agent containing the lymphocytes is suitably used in adoptive immunotherapy. In the adoptive immunotherapy, the lymphocytes suitable for treating a patient are administered to the patient by, for example, intravenous administration. The therapeutic agent is very useful for use in the above-mentioned diseases and donor lymphocyte infusion. The therapeutic agent can be prepared by, for example, blending the lymphocytes prepared by the method of the present invention as an effective ingredient with, for example, a known organic or inorganic carrier suitable for parenteral administration, an excipient, a stabilizing agent and the like, according to a method known in the pharmaceutical field. Incidentally, the amount of the lymphocytes of the present invention contained in the therapeutic agent, the dose of the therapeutic agent, and conditions for the therapeutic agent can be appropriately determined according to the known adoptive immunotherapy, and are not particularly limited. For example, the dose is exemplified by, preferably from $1\times10^5$ to $1\times10^{12}$ cells/day, more preferably from $1\times10^6$ to $5\times10^{11}$ cells/day, and even more preferably from $1\times10^6$ to $1\times10^{11}$ cells/day, for adult per day. Usually, the lymphocytes are administered intravenously, intra-arterially, subcutaneously, intraperitoneally or the like, by injection or drip. In an administration of the medicament of the present invention, for example, a component capable of functioning as a vaccine against cancer to be treated, in other words, a cancer vaccine, can be administered, and not particularly limited thereto. For example, a tumor antigen, a cell capable of presenting an antigen, a cell having presented an antigen, a cell from tumor tissue lacking its proliferating ability by the artificial manipulation, an extract from tumor tissue, or the like can be also administered. In addition, in the administration of the medicament, a lymphocyte-stimulating factor, for example, anti-CD3 antibody, anti-CD28 antibody, a cytokine (IL-2, IL-15, IL-7, IL-12, IFN-γ, IFN-α, IFN-β, or the like), a chemokine, or the like can be appropriately administered. Here, the term "lymphocyte-stimulating factor" as used herein encompasses lymphocyte-proliferating factor.

Diseases to which the lymphocytes prepared by the method of the present invention are administered are not particularly limited, and are exemplified by, for example, cancer, leukemia, malignant tumor, hepatitis, and infectious diseases caused by a virus such as influenza or HIV, bacteria, or a fungus, for example, tuberculosis, MRSA, VRE, and deep-seated mycosis. In addition, when a foreign gene is further transduced thereinto as described above, the effects are expected for various genetic diseases. The lymphocytes prepared by the method VVVVVVVVV can also be utilized for donor lymphocyte infusion and the like for the purpose of prevention from an infectious disease after bone marrow transplantation or irradiation, and remission of recurrent leukemia.

In addition, as another embodiment of the present invention, a method for treating the disease using the above-mentioned medicament is provided. The method for treating a disease is characterized in that the method uses the lymphocytes prepared by the above-mentioned method for preparing lymphocytes. Various conditions for administrating the medicament are such that the method can be carried out in accordance with the known adoptive immunotherapy and the disclosure of administration of the above-mentioned medicament.

As another embodiment of the present invention, a medium containing the effective ingredient in the present invention is provided. The medium further contains other optional components, for example, a medium component, proteins, and cytokines (preferably IL-2), which are used for a known cell culture, and other desired components. The amount of the effective ingredient in the present invention and the like contained in the medium is not particularly limited, so long as the desired effects of the present invention can be obtained. The amount contained can be appropriately determined as desired, for example, in accordance with the amount of the effective ingredient and the like contained in the above-mentioned medium used in the method of the present invention. One embodiment of the medium in the present invention encompasses a medium containing a cell culture carrier to which the effective ingredient in the present invention is immobilized and a medium provided by encapsulating the cell culture equipment immobilized with the effective ingredient in the present invention.

(4) Modified Fibronectin Polypeptide

In the present invention, there is also provided a novel polypeptide selected from the following (a) and (b), which is very useful in a use in the above-mentioned method for preparing lymphocytes:

(a) a novel polypeptide having an amino acid sequence selected from the group consisting of SEQ ID NO: 5 (H296-H296), SEQ ID NO: 16 (H296-H296-H296-HT), SEQ ID NO: 19 (CH296-CH296-HT), SEQ ID NO: 22 (H105-H105-HT), SEQ ID NO: 25 (H296-H296-HT), SEQ ID NO: 27 (H296-H296-H296), SEQ ID NO: 29 (H105-H105), SEQ ID NO: 32 (H271-H296), SEQ ID NO: 36 (H296-H271), SEQ ID NO: 39 (15aaH105-H105-HT), SEQ ID NO: 41 (15aaH105-H105), SEQ ID NO: 47 (H105-H105Nc-HT) and SEQ ID NO: 49 (H105-H105Nc) of Sequence Listing; and (b) a novel polypeptide having an amino acid sequence having deletion, insertion, addition or substitution of one or a plural number of amino acids in the amino acid sequence of the above polypeptide (a), the polypeptide having a function equivalent to the above polypeptide (a).

In addition, in the present invention, there is also provided a novel nucleic acid selected from the following (c) to (g):

(c) a nucleic acid encoding a polypeptide having an amino acid sequence selected from SEQ ID NOs: 5, 16, 19, 22, 25, 27, 29, 32, 36, 39, 41, 47 and 49 of Sequence Listing;

(d) a nucleic acid encoding a polypeptide having an amino acid sequence having deletion, insertion, addition or substitution of one or a plural number of amino acids in the amino acid sequence selected from SEQ ID NOs: 5, 16, 19, 22, 25, 27, 29, 32, 36, 39, 41, 47 and 49 of Sequence Listing, the polypeptide having a function equivalent to the polypeptide having an amino acid sequence selected from SEQ ID NOs: 5, 16, 19, 22, 25, 27, 29, 32, 36, 39, 41, 47 and 49 of Sequence Listing;

(e) a nucleic acid consisting of a nucleotide sequence selected from the group consisting of SEQ ID NO: 6 (nucleotide sequence of nucleic acid encoding H296-H296), SEQ ID NO: 17 (nucleotide sequence of nucleic acid encoding H296-H296-H296-HT), SEQ ID NO: 20 (nucleotide sequence of nucleic acid encoding CH296-CH296-HT), SEQ ID NO: 23 (nucleotide sequence of nucleic acid encoding H105-H105-HT), SEQ ID NO: 26 (nucleotide sequence of nucleic acid encoding H296-H296-HT), SEQ ID NO: 28 (nucleotide sequence of nucleic acid encoding H296-H296-H296), SEQ ID NO: 30 (nucleotide sequence of nucleic acid encoding H105-H105), SEQ ID NO: 33 (nucleic acid encoding H271-H296), SEQ ID NO: 37 (nucleic acid encoding H296-H271), SEQ ID NO: 40 (nucleic acid encoding 15aaH105-H105-HT), SEQ ID NO: 42 (nucleic acid encoding 15aaH105-H105), SEQ ID NO: 48 (nucleic acid encoding H105-H105Nc-HT) and SEQ ID NO: 50 (nucleic acid encoding H105-H105Nc) of Sequence Listing;

(f) a nucleic acid which hybridizes to the above nucleic acid (e) under stringent conditions, wherein the polypeptide encoded by the nucleic acid has a function equivalent to the polypeptide encoded by the above nucleic acid (e); and (g) a nucleic acid resulting from one or more substitutions, deletions, insertions or additions of one or a plural number of bases in the nucleotide sequence of the above nucleic acid (e), wherein the polypeptide encoded by the nucleic acid has a function equivalent to the polypeptide encoded by the above nucleic acid (e).

Incidentally, the above nucleic acid (c) is a nucleic acid encoding the above polypeptide (a), and the above nucleic acid (d) is a nucleic acid encoding the above polypeptide (b). In addition, the above polypeptide (a) is subjected to protein expression using the above nucleic acid (c), methionine residue at an N-terminal of the above polypeptide (a) is sometimes digested.

Here, in the present specification, the above-mentioned novel polypeptide may be referred to as the polypeptide of the present invention, and the above-mentioned novel nucleic acid may be referred to as the nucleic acid of the present invention.

The polypeptide of the present invention, the nucleic acid of the present invention, and the methods for preparing the polypeptide and the nucleic acid will be explained hereinafter.

The above polypeptide (b) of the present invention is exemplified by, preferably a polypeptide resulting from one or more substitutions, deletions, insertions or additions of 1 to 20 amino acids, more preferably a polypeptide resulting from one or more substitutions, deletions, insertions or additions of 1 to 10 amino acids, and even more preferably a polypeptide resulting from one or more substitutions, deletions, insertions or additions of 1 to 5 amino acids, in at least one amino acid sequence selected from the group consisting of SEQ ID NOs: 5, 16, 19, 22, 25, 27, 29, 32, 36, 39, 41, 47 and 49 of Sequence Listing. In addition, the above polypeptide (b) of the present invention encompasses a polypeptide in which His-tag sequence (first to 15th amino acid sequences in SEQ ID NO: 16, first to 15th amino acid sequences in SEQ ID NO: 19, first to 15th amino acid sequences in SEQ ID NO: 22, first to 15th amino acid sequences in SEQ ID NO: 25, first to 15th amino acid sequences in SEQ ID NO: 39, and first to 15th amino acid sequences in SEQ ID NO: 47) has been deleted from a polypeptide having the amino acid sequence shown in SEQ ID NOs: 16, 19, 22, 25, 39 or 47 of Sequence Listing, and a polypeptide in which His-tag sequence has been added to the amino acid sequence shown in SEQ ID NO: 5. Further, a methionine residue at an N-terminal of the polypeptide having the amino acid sequence shown in SEQ ID NO: 5 is deleted. It is expected that the methionine residue has been deleted by methionine aminopeptidase upon expression. In the present invention, deletion and insertion of the amino acid of the polypeptide (b) encompass insertion and deletion of the methionine residue at an N-terminal mentioned above. Incidentally, the substitution or the like of the amino acids may be carried out to an extent that it can change physicochemical characteristics and the like of a polypeptide within the range that the inherent function of the polypeptide can be maintained. The substitution or the like of the amino acids in this regard can be preferably carried out in the same manner in the description of "(1) Polypeptide (X) or Polypeptide (Y) Used in Present Invention."

The nucleic acid selected from the group consisting of SEQ ID NOs: 6, 17, 20, 23, 26, 28, 30, 33, 37, 40, 42, 48 and 50 of Sequence Listing, encoding the polypeptide of the present invention can be obtained by the method including the steps of obtaining a nucleic acid encoding each of domains constituting the polypeptide of the present invention using a nucleic acid encoding a natural fibronectin or a nucleic acid encoding a recombinant fibronectin fragment, for example, CH-296, H-296 or the like described above, and linking the resulting nucleic acids together by the known method. For example, as described in Examples 1, 22 to 24, 39 to 41, 45, 46, 52 and 53 set forth below, the above-mentioned nucleic acid can be obtained by the method including the steps of obtaining a nucleic acid encoding a part or all of a heparin binding domain and a nucleic acid encoding CS-1 domain from a nucleic acid encoding CH-296, and overlappingly linking the resulting nucleic acids together.

The nucleic acid of the present invention also includes a nucleic acid which hybridizes to a nucleic acid containing the nucleotide sequence selected from the group consisting of SEQ ID NOs: 6, 17, 20, 23, 26, 28, 30, 33, 37, 40, 42, 48 and 50 of Sequence Listing under stringent conditions and encodes a polypeptide having a function equivalent to that of the polypeptide of the present invention, i.e., the desired effects in the preparation of the lymphocytes described above. The term "stringent conditions" mentioned above are not particularly limited, and can be set by, for example, appropriately determining temperature and salt concentration upon hybridization, preferably additionally upon washing, depending on the DNA which hybridizes to the DNA containing these nucleotide sequences. The stringent conditions include, for example, the conditions described in a literature such as *Molecular cloning, A laboratory manual* 3$^{rd}$ edition (Sambrook et al., *Molecular cloning, A laboratory manual* 3$^{rd}$ edition, 2001, published by Cold Spring Harbor Laboratory Press).

Specifically, for example, the stringent conditions are exemplified by incubation at 50° C., preferably at 65° C. in a solution containing 6×SSC (1×SSC being 0.15 M NaCl, 0.015 M sodium citrate, pH 7.0), 0.5% SDS, 5×Denhardt's (0.1% bovine serum albumin (BSA), 0.1% polyvinyl pyrrolidone, 0.1% Ficoll 400) and 100 µg/mL salmon sperm DNA. When Tm value of the DNA used is known, the above-mentioned temperature may be lower than that value by 5° to 12° C. Furthermore, in the step of removing the DNA hybridizing non-specifically by washing, from the viewpoint of further improving accuracy, a condition that washing is carried out under conditions, such as a condition of lower ionic strength, for example, 2×SSC, and more stringently 0.1×SSC, and/or a condition of higher temperature, for example, 25° C. or more, more stringently 37° C. or more, further more stringently 42° C. or more, and even further more stringently 50° C. or more, varying depending on the Tm value of the nucleic acid used, or the like, may be added.

The present invention also encompasses a nucleic acid molecule which hybridizes to the polynucleotide of the present invention under lower stringent hybridization conditions. Variations of stringency of the hybridization and signal detection are carried out mainly by manipulation of formamide concentration (lower percentile of formamide results in lowered stringency), salt concentration or temperature. For example, lower stringent conditions include overnight incubation at 37° C. in a solution containing 6×SSPE (20× SSPE=3 M NaCl; 0.2 M NaH$_2$PO$_4$; 0.02 M EDTA, pH 7.4), 0.5% SDS, 30% formamide, 100 µg/mL salmon sperm blocking DNA; followed by washing with 1×SSPE and 0.1% SDS at 50° C. Furthermore, in order to accomplish lower stringency, the washing carried out after the stringent hybridization can be carried out at a higher salt concentration (for example, 5×SSC).

The above-mentioned conditions can be modified by adding and/or substituting an alternative blocking reagent used for suppressing background in a hybridization experiment. Typical blocking reagent includes Denhardt's reagent, BLOTTO, heparin, denatured salmon sperm DNA and commercially available product formulation. In addition, other elements other than the above-mentioned hybridization conditions are needed to be modified depending on this modification, in some cases.

In addition, the nucleic acid of the present invention includes a nucleic acid resulting from one or more substitutions, deletions, insertions or additions of one or a plural number of bases in the nucleotide sequence of a nucleic acid selected from the group consisting of SEQ ID NOs: 6, 17, 20, 23, 26, 28, 30, 33, 37, 40, 42, 48 and 50 of Sequence Listing. For example, the nucleic acid of the present invention is exemplified by, a nucleic acid resulting from one or more substitutions, deletions, insertions or additions of 1 to 60 bases, more preferably a nucleic acid resulting from one or more substitutions, deletions, insertions or additions of 1 to 30 bases, and even more preferably a nucleic acid resulting from one or more substitutions, deletions, insertions or additions of 1 to 15 bases, in the nucleotide sequence described in SEQ ID NO: 6, 17, 20, 23, 26, 28, 30, 33, 37, 40, 42, 48 or 50 of Sequence Listing. Incidentally, the substitution or the like of the bases may be carried out to an extent that it can change physicochemical characteristics and the like of a polypeptide within the range that the function of the polypeptide encoded by the nucleic acid can be maintained. The detail and the method of substitution or the like of the bases are in accordance with the description regarding the substitution or the like of the amino acids mentioned above.

On the other hand, the polypeptide of the present invention, especially, a polypeptide having an amino acid sequence selected from the group consisting of SEQ ID NOs: 5, 16, 19, 22, 25, 27, 29, 33, 37, 40, 42, 47 and 49 of Sequence Listing can be obtained in a genetic engineering manner, using the nucleic acid thus obtained. In other words, the polypeptide can be obtained by inserting the nucleic acid into an appropriate expression vector, for example, pET vector, pCold vector, or the like, without particular limitation, to express the polypeptide by a known method, for example, in *Escherichia coli* or the like.

EXAMPLES

The present invention will be more specifically described hereinafter by the Examples, without intending to limit the scope of the present invention thereto.

Preparation Example 1

Preparation of H-296

H-296, a polypeptide comprising a heparin binding domain and a CS-1 domain of fibronectin, was prepared using *Escherichia coli* HB101/pHD102 (FERM BP-7420) in accordance with the descriptions of U.S. Pat. No. 5,198,423.

Preparation Example 2

Preparation of CH-296

CH-296, a polypeptide comprising a cell binding domain, a heparin binding domain and a CS-1 domain of fibronectin, was prepared using *Escherichia coli* HB101/pCH102 (FERM BP-2800) in accordance with the descriptions of U.S. Pat. No. 5,198,423.

Example 1

Generation of H296-H296

Of the procedures described in the present specification, the basic procedures such as the generation of plasmids and the digestion with restriction enzymes were performed in accordance with the method described in *Molecular Cloning: A Laboratory Manual* 3rd edition, 2001, edited by T. Maniatis et al., published by Cold Spring Harbor Laboratory Press.
(1) Construction of Expression Vectors
(i) Construction of H-296 Expression Vector A polypeptide consisting of amino acids 278-574 (base numbers 835-1725) from the N-terminal of the amino acid sequence of CH-296 shown in SEQ ID NO: 7 of Sequence Listing is referred to as H-296, and in order that a modified fibronectin fragment in which two of these H-296's connected to each other (H296-H296) is allowed to express, an expression vector was constructed in the following manner Reference is made to FIG. 2 hereinbelow.

First, from the nucleotide sequence of CH-296 shown in SEQ ID NO: 8 of Sequence Listing (see WO 03/080817), synthetic primers H296-NcoF and H296-HindR having nucleotide sequences shown in SEQ ID NOs: 9 and 10 of Sequence Listing were synthesized with a DNA synthesizer, and purified according to a conventional method. The above-mentioned synthetic primer H296-NcoF is a synthetic DNA having a recognized sequence with a restriction enzyme NcoI in the base numbers 11-16, and further having a nucleotide sequence corresponding to amino acid numbers 278-283 of the amino acid sequence of CH-296 (SEQ ID NO: 7) in the base numbers 13-30. In addition, the synthetic primer H296-HindR is a synthetic DNA having a recognized sequence with a restriction enzyme HindIII in the base numbers 11-16, and further having a nucleotide sequence corresponding to amino acid numbers 570-574 of the amino acid sequence of CH-296 (SEQ ID NO: 7) in the base numbers 20-34.

PCR was carried out using the above-mentioned synthetic primers. The reaction conditions for PCR are given hereinafter. Concretely, about 0.1 µg of pCH102 as a template DNA, 5 µL of 10× Ex Taq Buffer (manufactured by TAKARA BIO, INC.), 5 µL of a dNTP mixture (manufactured by TAKARA BIO, INC.), 10 pmol of a synthetic primer H296-NcoF, 10 pmol of a synthetic primer H296-HindR, and 0.5 U TaKaRa Ex Taq (manufactured by TAKARA BIO, INC.) were added together, and a sterile water was added thereto to make up a total volume of 50 µL. The above reaction mixture was set in TaKaRa PCR Thermal Cycler SP (manufactured by TAKARA BIO, INC.), and 30 cycles of reaction, each cycle comprising 94° C. for 1 minute, 55° C. for 1 minute, and 72° C. for 3 minutes, were performed.

After the termination of the reaction, 5 µL of the reaction mixture was electrophoresed with 1.0% agarose gel, and a desired DNA fragment having a size of about 0.9 kbp was confirmed. The remainder of the reaction mixture for PCR was electrophoresed, and a fragment thereof was collected and purified, and the purified mixture was subjected to ethanol precipitation. The DNA collected after the ethanol precipitation was suspended in 10 µL of a sterile water, and subjected to a double digestion with a restriction enzyme NcoI (manufactured by TAKARA BIO, INC.) and a restriction enzyme HindIII (manufactured by TAKARA BIO, INC.), and the digest was electrophoresed with 1.0% agarose gel, thereby extracting and purifying the NcoI and HindIII digest, to give an NcoI-HindIII-digested DNA fragment.

Next, in accordance with the methods described in Examples 1 to 6 of WO 99/27117, a pCold04NC2 vector (hereinafter, this pCold04NC2 vector is simply referred to as "pCold14 vector") was prepared.

Next, the above-mentioned pCold14 vector was cleaved with the same restriction enzymes as those used in the preparation of the above-mentioned NcoI-HindIII-digested DNA fragment, and the terminals of the products were subjected to a dephosphorization treatment to prepare a product, and the product was mixed with the above-mentioned NcoI-HindIII-digested DNA fragment, and ligated using a DNA ligation kit (manufactured by TAKARA BIO, INC.). Thereafter, *Escherichia coli* JM109 was transformed with 20 µL of the ligation reaction mixture, and the resulting transformant was grown on an LB medium (containing 50 µg/mL ampicillin) containing agar in a concentration of 1.5% (w/v).

The plasmid inserted with a desired DNA fragment was confirmed by sequencing, and this recombinant plasmid was referred to as pCold14-H296. This pCold14-H296 is a plasmid containing a nucleotide sequence encoding the amino acid sequence of the amino acid numbers 278-574 of CH-296.
(ii) Construction of H296-H296 Expression Vector Next, a synthetic primer H296-NcoR having the nucleotide sequence as shown in SEQ ID NO: 11 of Sequence Listing was synthesized with a DNA synthesizer, on the basis of the nucleotide sequences published in WO 03/080817, and purified according to a conventional method. The above-mentioned synthetic primer H296-NcoR is a synthetic DNA having a recognized sequence with a restriction enzyme NcoI in the base numbers 10-15, and further having a nucleotide sequence corresponding to amino acid numbers 574-569 of the amino acid sequence of CH-296 (SEQ ID NO: 7) in the base numbers 17-34. PCR was performed using the above-mentioned synthetic primer and a primer NC2-5'UTR obtained by annealing a 5'UTR moiety of pCold14 vector as shown in SEQ ID NO: 12 of Sequence Listing. The reaction conditions for PCR are given hereinafter.

Concretely, about 0.1 µg of pCold14-H296 as a template DNA, 10 µL of 10× Pyrobest Buffer II (manufactured by TAKARA BIO, INC.), 8 µL of the dNTP mixture, 20 pmol of a synthetic primer NC2-5'UTR, 20 pmol of a synthetic primer H296-NcoR, and 5 U Pyrobest DNA Polymerase (manufactured by TAKARA BIO, INC.) were added together, and a sterile water was added thereto to make up a total volume of 100 µL. The above reaction mixture was set in the TaKaRa PCR Thermal Cycler SP, and 30 cycles of reaction, each cycle comprising 96° C. for 1 minute and 68° C. for 4 minutes, were performed.

After the termination of the reaction, 5 µL of the reaction mixture was electrophoresed with 1.0% agarose gel, and a desired DNA fragment having a size of about 0.9 kbp was confirmed. The remainder of the reaction mixture for PCR was collected and purified with a Bio-Rad column, and the purified mixture was subjected to ethanol precipitation. The DNA collected after the ethanol precipitation was suspended in 39 µL of a sterile water, to make up a total volume of the reaction mixture of 50 µL, the reaction mixture was digested with the restriction enzyme NcoI, and the digest was electrophoresed with 1.0% agarose gel, thereby extracting and purifying an NcoI, NcoI digest, to give an NcoI-NcoI-digested DNA fragment.

Next, the pCold14-H296 prepared in (i) was digested with the restriction enzyme NcoI, and the terminals of the digest were subjected to a dephosphorization treatment to prepare a product, and the product was mixed with the above-mentioned NcoI-NcoI-digested DNA fragment, and ligated with the DNA ligation kit. Thereafter, *Escherichia coli* JM109 was transformed with 20 µL of the ligation reaction mixture, and the resulting transformant was grown on an LB medium (containing 50 µg/mL ampicillin) containing agar in a concentration of 1.5% (w/v).

The plasmid inserted with a desired DNA fragment was confirmed by sequencing, and this recombinant plasmid was referred to as pCold14-H296-H296. This pCold14-H296-H296 is a plasmid containing two nucleotide sequences encoding the amino acid sequence of the amino acid numbers 278-574 of CH-296 connected with an amino acid "A" inserted therebetween. The amino acid sequence of the protein expressed by the plasmid is shown in SEQ ID NO: 5 of Sequence Listing, and the nucleotide sequence is shown SEQ ID NO: 6 of Sequence Listing.

(2) Expression and Purification

*Escherichia coli* BL21 was transformed with pCold14-H296-H296 prepared in the above-mentioned (1), and the resulting transformant was grown on LB medium (containing 50 µg/mL ampicillin) containing agar having a concentration of 1.5% (w/v). The obtained colonies were inoculated on 30 mL LB liquid medium (containing 50 µg/mL ampicillin), and cultured overnight at 37° C. An entire amount of the cultured medium was inoculated on 3 L of the same LB medium, and cultured at 37° C. up to a logarithmic growth phase. Here, this culture was carried out using a 5 L minijar fermenter (manufactured by Biott) under the conditions of 120 r/min and Air=1.0 L/min After the above-mentioned culture, the culture medium was cooled to 15° C., IPTG was then added so as to have a final concentration of 1.0 mM, and the culture was carried out in this state at 15° C. for 24 hours to induce expression. Thereafter, the cells were harvested by centrifugation, and resuspended in about 40 mL of a cell disruption solution [50 mM Tris-HCl (pH 7.5), 1 mM EDTA, 1 mM DTT, 1 mM PMSF, 50 mM NaCl]. The cells were disrupted by ultrasonic disruption, and the disruption was centrifuged (11,000 r/min, 20 minutes), thereby separating the disruption into an extract of the supernatant and precipitates. The extract of the supernatant obtained was dialyzed against 2 L of buffer A[50 mM Tris-HCl (pH 7.5), 50 mM NaCl], and subjected to further purification by ion-exchange chromatography using about 40 mL of the dialyzed extract in the manner described below.

Concretely, a column (φ4 cm×20 cm) of SP-Sepharose (manufactured by Amersham Pharmacia) having a resin volume corresponding to 100 mL, saturated with the buffer A was furnished, and the dialyzed sample was applied thereto. Thereafter, the elution of the target protein was carried out with a 50 mM to 1 M sodium chloride concentration gradient in 250 mL of the buffer A and 250 mL of buffer B [50 mM Tris-HCl (pH 7.5), 1 M NaCl]. The fractionation was carried out in a 5 mL portion, and the fraction was analyzed by 10% SDS-PAGE, to collect about 100 mL of a fraction richly containing a target protein having a molecular weight of about 65 kDa, and the fraction was dialyzed against 2 L of the buffer A.

Next, a column (φ3 cm×16 cm) of Q-Sepharose (manufactured by Amersham Pharmacia) having a resin volume corresponding to 50 mL, saturated with the buffer A was furnished, and the dialyzed sample was applied thereto. Thereafter, the elution of the target protein was carried out with a 50 mM to 1 M sodium chloride concentration gradient in 250 mL of the buffer A and 250 mL of the buffer B. The fractionation was carried out in a 5 mL portion, and the fraction was analyzed by 10% SDS-PAGE, to collect about 100 mL of a fraction richly containing a target protein having a molecular weight of about 65 kDa, and the fraction was dialyzed against 2 L of buffer D [50 mM sodium carbonate buffer (pH 9.5)].

Subsequently, the dialyzed fraction was concentrated about 20 times to a volume of 5 mL with Centricone-10 (manufactured by Millipore Corporation), and the concentrate was further confirmed by 10% SDS-PAGE. Consequently, a target protein having a molecular weight of about 65 kDa was detected in a nearly single band, which was referred to as H296-H296. Thereafter, a protein concentration was determined using a MicroBCA kit (manufactured by Pierce). As a result, the protein concentration was found to be 2.16 mg/mL (about 33 µM, calculated from its molecular weight). In addition, the N-terminal analysis was carried out; as a result, methionine was digested, so that the N-terminal was Ala.

Example 2

Induction of CTLs Having Specific Cytotoxic Activity Using H296-H296

(1) Isolation and Storage of PBMCs

Apheresis was performed on a human healthy donor having HLA-A2.1. The collected blood was then diluted 2-fold with phosphate buffered saline (PBS), overlaid on Ficoll-paque (manufactured by Amersham Biosciences), and centrifuged at 600×g for 20 minutes. After the centrifugation, the peripheral blood mononuclear cells (PBMCs) in the intermediate layer were collected with a pipette, and washed. The collected PBMCs were suspended in RPMI 1640 medium (manufactured by Sigma) so as to have a concentration of $5 \times 10^7$ cells/mL, and thereafter a storage mixture prepared by mixing CP-1 (manufactured by KYOKUTO PHARMACEUTICAL INDUSTRIAL CO., LTD.) and 25% human serum albumin (BUMINATE, manufactured by Baxter Limited) in a ratio of 17:8 was added in an equivolume to the suspension, and suspended, and stored in liquid nitrogen. Upon the induction of CTLs, these stored PBMCs were rapidly thawed in water bath at 37° C., and washed with the RPMI 1640 medium containing 10 µg/mL DNase (manufactured by Calbiochem). Thereafter, the number of viable cells was counted by trypan blue staining method. The cells were subjected to each experiment.

(2) Immobilization of H296-H296 Fragment

H296-H296 was immobilized to a culture equipment used in the following experiment. Concretely, PBS containing H296-H296 (final concentration: 25 µg/mL) was added to a 24-well cell culture plate (manufactured by Becton, Dickinson and Company) in a volume of 1 mL/well each, and the mixture was incubated overnight at 4° C. In addition, the above-mentioned plate was washed twice with PBS before use, and then washed once with the RPMI 1640 medium.

(3) Induction of Anti-Influenza Virus Memory CTLs

The induction of anti-influenza virus memory CTLs was performed by partially modifying the method of Bednarek et al. [Bednarek M. A. et al., *J. Immunology*, 147(12), 4047-4053 (1991)]. Concretely, PBMCs prepared in Example 2-(1) were suspended in the RPMI 1640 medium containing 5% human AB serum, 1 mM sodium pyruvate, 2 mM L-glutamine, 1×NEAA Mixture (all manufactured by Cambrex), and 1% streptomycin-penicillin (manufactured by Nakalai Tesque Inc.) (hereinafter simply referred to as "5HRPMI") so as to have a concentration of $4\times10^6$ cells/mL Thereafter, the suspension was put in the 24-well cell culture plate prepared in Example 2-(2) in a volume of 1 mL/well, and the cells were incubated in a 5% $CO_2$ humidified incubator at 37° C. for 1.5 hours, to isolate plastic-adherent monocytes (As the control, a plate without the immobilization treatment with H296-H296 was used.). Thereafter, nonadherent cells were collected using the RPMI 1640 medium, and stored on ice as responder cells. To isolated monocytes was added 0.5 mL each of 5HRPMI containing as an antigen peptide 5 μg/mL epitope peptide derived from influenza virus protein (HLA-A2.1-binding peptide derived from the matrix protein as shown in SEQ ID NO: 13 of Sequence Listing) and 1 μg/mL β2 microglobulin (manufactured by Scrips). The mixture was incubated at room temperature for 2 hours, and thereafter the cells were subjected to X-ray irradiation (1.42 C/kg) for antigen-presenting cells. The peptide solution was removed by aspiration from each of the wells, and the wells were washed with the RPMI 1640 medium. Thereafter, the responder cells previously stored on ice were suspended in 5HRPMI so as to have a concentration of $1\times10^6$ cells/mL, and the suspension was added to antigen-presenting cells in a volume of 1 mL per well. Thereafter, the plate was cultured at 37° C. in the presence of 5% $CO_2$. On the first day from the initiation of the culture, 1 mL of 5HRPMI containing 60 U/mL IL-2 (PROLEUKIN, manufactured by CHIRON) was added to each well. Also, on the fifth day, a half of the culture supernatant was removed, and 1 mL each of IL-2-containing medium, the same as that mentioned above, was added thereto. On the seventh day, the antigen-presenting cells were prepared in the same manner as above, and the responder cells which had been cultured for one week were then harvested, and centrifuged at 440×g for 10 minutes. After the centrifugation, the responder cells were suspended in 1 mL of 5HRPMI. The suspension was added to the antigen-presenting cells prepared in a volume of 1 mL/well each to re-stimulate the cells. Here, as the plate, one immobilized with H296-H296 was used (as the control, a plate without the immobilization being used). On the first day from re-stimulation, 1 mL of 5HRPMI containing 60 U/mL IL-2 was added to each well. Also, on the fourth or fifth day, a half of the culture supernatant was removed, 1 mL each of the medium having the same content as that before removal was then added thereto, and the culture was further continued to induce CTLs. The cell proliferation rate after the 14-day culture is shown in Table 1. The cell proliferation rate was defined by a ratio of the number of cells at the point of time of the termination of the induction to the number of responder cells at the initiation of the induction of CTLs as a proliferation rate.

TABLE 1

| Sample | Cell Proliferation Rate (fold) |
| --- | --- |
| Control | 2.3 |
| H296-H296 | 4.9 |

As a result, the group immobilized with H296-H296 showed a high proliferation rate, as compared to the control group without the immobilization. In other words, it was clarified that the proliferation rate of the cells was enhanced by using H296-H296 during the induction of CTLs.

Example 3

Expansion of CTLs of Example 2 Using Feeder Cells (1) Immobilization of H296-H296 Fragment H296-H296 was immobilized to a culture equipment used in the following experiment. Concretely, PBS containing H296-H296 (final concentration: 25 μg/mL) was added to a 12.5 $cm^2$ flask (standing culture) (manufactured by Becton, Dickinson and Company) in a volume of 2.7 mL/well each, and the mixture was incubated overnight at 4° C. In addition, the above-mentioned flask was washed twice with PBS before use, and then washed once with the RPMI 1640 medium.

(2) Expansion of CTLs of Example 2 Using Feeder Cells

CTLs which had been induced in the presence of H296-H296 (the control being CTLs induced in the absence of H296-H296), prepared in Example 2-(3) were adjusted to a concentration of $3\times10^4$ cells/mL On the other hand, allogenic PBMCs not having HLA-A2.1 which were collected in the same manner as in Example 2-(1) were obtained by mixing two donors, and the mixture was then subjected to X-ray irradiation (0.851 C/kg), and the cells were washed with the medium and then made into a suspension having a concentration of $4\times10^6$ cells/mL (used as feeder cells). These CTLs in an amount of $3\times10^4$ cells and the feeder cells in an amount of $4\times10^6$ cells were suspended in 5 mL of the RPMI 1640 medium containing 10% Hyclone FBS (manufactured by Hyclone), 1 mM sodium pyruvate, 2 mM L-glutamine, 1×NEAA Mixture and 1% streptomycin-penicillin (hereinafter simply referred to as "10Hyclone RPMI"), and an anti-CD3 antibody (anti-human CD3 monoclonal antibody (OKT3); manufactured by Janssen-Pharma) having a final concentration of 50 ng/mL was further added thereto. The mixture was placed into the 12.5 $cm^2$ flask (standing culture), and the cells were cultured in a humidified $CO_2$ incubator at 37° C. for 14 days. Here, a flask immobilized with H296-H296 of Example 3-(1) was used (as the control, a flask without the immobilization being used). Stimulation by a peptide was not added at all during this culture. On the first day of the initiation of the expansion, 5 mL of 10Hyclone RPMI and IL-2 having a final concentration of 120 U/mL were added thereto. Further, on the fifth day and on from the initiation of the culture, procedures of removing a half of the culture supernatant, and thereafter adding 5 mL of 10Hyclone RPMI containing 60 U/mL IL-2 to each flask were carried out every 2 to 3 days, and the expansion was carried out for 14 days. The results are shown in Table 2. The proliferation rate during the expansion was defined by a ratio of the number of cells at the point of time of the termination of the expansion to the number of cells at the initiation of the expansion as a proliferation rate, and the proliferation rate from the induction was defined by a ratio of the number of cells at the point of time of the termination of the expansion to the number of responder cells at the initiation of the induction as a proliferation rate.

TABLE 2

| | Cell Proliferation Rate (fold) | |
| --- | --- | --- |
| Sample | During the Expansion | from the Induction |
| Control | 45.5 | 104.6 |
| H296-H296 | 193.1 | 954.6 |

As a result, the CTLs of the group immobilized with H296-H296 during the induction and expansion of CTLs showed higher proliferation rates than the control group without the immobilization of H296-H296. In other words, it was clarified that the proliferation rates of the cells were enhanced by using H296-H296 during the induction and the expansion of CTLs.

Example 4

Assay of Cytotoxic Activity of CTLs of Example 3

The cytotoxic activity of the CTLs on the fourteenth day from the initiation of expansion prepared in Example 3 was evaluated by a method for cytotoxic activity using Calcein-AM [Lichtenfels R. et al., *J. Immunol. Methods,* 172(2), 227-239 (1994)]. HLA-A2.1-having EBV transformed B-cells (name of cells: 221A2.1), which were cultured overnight in the presence or in the absence of an epitope peptide, were suspended in the RPMI 1640 medium containing 5% FBS (fetal bovine serum, manufactured by Cambrex) so as to have a concentration of $1\times10^6$ cells/mL, and Calcein-AM (manufactured by DOJINDO LABORATORIES) was then added thereto so as to have a final concentration of 25 µM, and the cells were cultured at 37° C. for 1 hour. The cells were washed with a medium without containing Calcein-AM, and thereafter obtained as Calcein-labeled target cells. The Calcein-labeled target cells were mixed with 30-fold amount of K562 cells (ATCC CCL-243), to provide cells for cytotoxic activity. Here, the K562 cells were used for excluding non-specific cytotoxic activity by NK cells admixed in the responder cells.

The anti-influenza virus memory CTLs prepared in Example 3 were serially diluted with the 5HRPMI as effector cells, so as to have a concentration of from $1\times10^5$ to $3\times10^6$ cells/mL. Thereafter, the dilution was previously dispensed to each well of a 96-well cell culture plate (manufactured by Becton, Dickinson and Company) in a volume of 100 µL/well each, and to these wells were added the cells for cytotoxic activity in a volume of 100 µL/well each prepared so that the Calcein-labeled target cells had a concentration of $1\times10^5$/mL. Upon assaying, a ratio of the effector cells (E) to the Calcein-labeled target cells (T) is expressed as an E/T ratio, and the assays were conducted at E/T ratios of 30, 10, 3, and 1. The plate containing the above cell suspension was centrifuged at 400×g for 1 minute, and thereafter the cells were incubated in a humidified $CO_2$ incubator at 37° C. for 4 hours. Four hours later, 100 µL of the culture supernatant was collected from each well, and the amount of Calcein released into the culture supernatant was determined with a fluorescence plate reader (spectrofluorometer) (manufactured by BERTHOLD TECHNOLOGIES) (excited at 485 nm/measured at 538 nm) "Specific Cytotoxic Activity (%)" was calculated in accordance with the following formula 1:

Specific Cytotoxic Activity (%)={(Found Value in Each Well−Minimum Released Amount)/(Maximum Released Amount−Minimum Released Amount)}×100   Formula 1

In the above formula, the minimum released amount is the amount of Calcein released in the well containing only the cells for assaying cytotoxic activity, showing an amount of Calcein spontaneously released from the Calcein-labeled target cells. In addition, the maximum release shows an amount of Calcein released when the cells are completely disrupted by adding 0.1% of the surfactant Triton X-100 (manufactured by Nakalai Tesque Inc.) to the cells for assaying cytotoxic activity. In addition, in the E/T ratio of 3, the extent to which the cytotoxic activity before the expansion is maintained was calculated as "Cytotoxic Activity Maintenance (%)" according to the following formula 2:

Cytotoxic Activity Maintenance (%)=[Cytotoxic Activity (%) After Expansion/Cytotoxic Activity (%) Before Expansion]×100   Formula 2

The results of the assays are shown in Table 3.

TABLE 3

| Sample | Cytotoxic Activity (%) After Expansion of CTLs E/T Ratio | | | | Effect of Activity Maintenance (%) |
|---|---|---|---|---|---|
|  | 30 | 10 | 3 | 1 | E/T = 3 |
| Control | n.t. | 72.7 | 36.6 | 12.1 | 73.9 |
| H296-H296 | 89.6 | 83.9 | 62.4 | 28.9 | 123.3 | n.t.: not tested

The cytotoxic activity against the Calcein-labeled target cells cultured in the absence of the peptide was almost 0%, confirming that the non-specific activity was not found therefor. In the cytotoxic activity against the Calcein-labeled target cells cultured in the presence of the peptide, those of the group immobilized with the H296-H296 fragment during the induction and the expansion of CTLs maintained specific, high cytotoxic activities even after the expansion for 14 days. On the other hand, in the control group without being immobilized with H296-H296 in both during the induction and the expansion of CTLs, the activity was clearly lowered. In other words, it was clarified that the expansion of CTLs could be carried out in a state that a specific, high cytotoxic activity was maintained for a long period of time by using H296-H296 during the induction and the expansion of CTLs.

Example 5

Determination of Content Ratio of TCR Vβ17-Positive Cells in Cell Population of CTLs of Example 3

The peptide derived from HLA-A2.1-binding influenza virus protein presently used in the induction is shown by Lehner et al. to be recognized by TCR Vβ17-positive T cells [Lehner P. J. et al., *J. Exp. Med.,* 181, 79-91 (1995)]. Therefore, the determination of the content ratio of the TCR Vβ17-positive cells could serve as an index for the anti-influenza virus memory CTLs.

The CTLs in an amount of $2\times10^5$ cells which were prepared in Example 3 were washed with PBS, and the cells were suspended in 15 µL of PBS containing 1% bovine serum albumin (BSA) (manufactured by Sigma), FITC-labeled mouse IgG1 or FITC-labeled mouse anti-human TCR Vβ17 antibody (both manufactured by BECKMAN COULTER) was added thereto, and the mixture was then incubated on ice for 30 minutes. After the incubation, the cells were washed twice with PBS containing 0.1% BSA, and suspended in PBS containing 1% BSA. These cells were subjected to flow cytometry using Cytomics FC500 (manufactured by BECKMAN COULTER), and the content ratio of TCR Vβ17-positive cells was determined. The determination results are shown in Table 4.

TABLE 4

| Sample | Content Ratio (%) of TCR Vβ17-Positive Cells |
| --- | --- |
| Control | 24.9 |
| H296-H296 | 85.3 |

The CTLs of the group immobilized with H296-H296 during the induction and the expansion of CTLs clearly showed a high content ratio of positive cells, as compared to that of the control group without the immobilization. Here, the content ratio of the CTLs after the induction, in other words, TCR Vβ17-positive cells before the expansion, was 78.0% for the group immobilized with H296-H296, and 73.0% for the control group without the immobilization. In other words, it was found that the expansion could be carried out while maintaining a high content ratio of the anti-influenza virus memory CTLs by using H296-H296 during the induction and the expansion of CTLs.

Example 6

Expansion of CTLs of Example 2 Without Using Feeder Cells (1) Immobilization of Anti-CD3 Antibody and H296-H296 Fragment H296-H296 was immobilized to a culture equipment used in the following experiment for the expansion of CTLs without using the feeder cells. Concretely, PBS containing an anti-CD3 antibody (final concentration: 5 μg/mL) and H296-H296 (final concentration: 25 μg/mL) was added to a 96-well cell culture plate in a volume of 160 μL/well each, and the mixture was incubated overnight at 4° C. (the control being immobilized only with the anti-CD3 antibody). In addition, the above-mentioned plate was washed twice with PBS before use, and then washed once with the RPMI 1640.

(2) Expansion of CTLs Without Using Feeder Cells

CTLs which had been induced in the presence of H296-H296 (the control being CTLs induced in the absence of H296-H296), prepared in Example 2-(3) were washed with 5HRPMI, the $1 \times 10^5$ cells were then suspended in 300 μL of 5HRPMI, and the culture was initiated in a humidified $CO_2$ incubator at 37° C. using the 96-well culture plate prepared in Example 6-(1). On the first day of the initiation of the culture, IL-2 was added so as to have a final concentration of 120 U/mL. Further, on the fifth day and on after the initiation of the culture, subculture was carried out with a plate without the immobilization every 2 to 3 days, and IL-2 having a final concentration of 100 U/mL was added. Stimulation by a peptide was not added at all during this culture, and the expansion was carried out for 13 days. The cell proliferation rate is shown in Table 5.

TABLE 5

| Sample | Cell Proliferation Rate (fold) | |
| --- | --- | --- |
| | During the Expansion | from the Induction |
| Control | 9.2 | 21.1 |
| H296-H296 | 30.6 | 149.8 |

As a result, those of the group immobilized with H296-H296 during the induction and expansion showed higher proliferation rates than the control group without the immobilization. In other words, it was clarified that the expansion of CTLs could be carried out without using the feeder cells by using H296-H296 during the induction and the expansion.

Example 7

Assay of Cytotoxic Activity of CTLs of Example 6

The specific cytotoxic activity of CTLs for the CTLs obtained in Example 6-(2) was assayed in the same manner as in Example 4. The results are shown in Table 6.

TABLE 6

| Sample | Cytotoxic Activity (%) After Expansion of CTLs E/T Ratio | | | | Effect of Activity Maintenance (%) |
| --- | --- | --- | --- | --- | --- |
| | 30 | 10 | 3 | 1 | E/T = 3 |
| Control | n.t. | 53.3 | 20.8 | 8.2 | 42.2 |
| H296-H296 | 84.8 | 80.0 | 53.0 | 25.8 | 104.8 | n.t.: not tested

The cytotoxic activity against the Calcein-labeled target cells cultured in the absence of the peptide was almost 0%, confirming that the non-specific activity was not found therefor. Regarding the cytotoxic activity against the Calcein-labeled target cells cultured in the presence of the peptide, the CTLs of the group with addition of H296-H296 during the induction and the expansion maintained specific, high cytotoxic activities than those of the control group even after the expansion for 13 days. In other words, it was clarified that the expansion could be carried out in a state that a specific, high cytotoxic activity was maintained for a long period of time according to a method without using the feeder cells by using H296-H296 during the induction and the expansion of CTLs.

Example 8

Determination of Content Ratio of TCR Vβ17-Positive Cells in Cell Population of CTLs of Example 6

The content ratio of TCR Vβ17-positive cells was determined for the CTLs in an amount of $2 \times 10^5$ cells prepared in Example 6-(2) in the same manner as in Example 5. As to the control group using the CTLs expanded in the absence of H296-H296, since the number of cells obtained after the expansion was small, the test was not conducted. The results are shown in Table 7.

TABLE 7

| Sample | Content Ratio (%) of TCR Vβ17-Positive Cells |
| --- | --- |
| H296-H296 | 81.5 |

The group in which H296-H296 was used during the induction and the expansion showed a high content ratio of positive cells. Here, the content ratio of the CTLs after the induction, in other words, the TCR Vβ17-positive cells before the expansion, was 78.0% for the group immobilized with H296-H296. In other words, it was found that the expansion could be carried out while maintaining a high content ratio of the anti-influenza virus memory CTLs in a system without using feeder cells by using H296-H296 during the induction and the expansion.

Example 9

Induction of CTLs Having Specific Cytotoxic Activity Using H296-H296 and H-296

(1) Immobilization of H296-H296 and H-296 Fragments

H296-H296 and H-296 were immobilized to a culture equipment used in the following experiment. Concretely, PBS containing each of H296-H296 and H-296 (final concentration: 25 µg/mL) was added to a 24-well cell culture plate in a volume of 1 mL each, and the mixture was incubated overnight at 4° C. In addition, the above-mentioned plate was washed twice with PBS before use, and then washed once with the RPMI 1640 medium.

(2) Induction of Anti-Influenza Virus Memory CTLs

Using the PBMCs isolated and stored in accordance with the method described in Example 2-(1), the induction of the anti-influenza virus memory CTLs was carried out in the same manner as in Example 2-(3). During the induction, the culture plate used was the one prepared in Example 9-(1) (as the control, a plate without immobilization of H296-H296 and H-296 being used). The cell proliferation rate on the fourteenth day from the initiation of the induction is shown in Table 8.

TABLE 8

| Sample | Cell Proliferation Rate (fold) |
|---|---|
| Control | 1.1 |
| H296-H296 | 4.3 |
| H-296 | 3.2 |

As a result, the group immobilized with H296-H296 showed the highest proliferation rate, followed by the group immobilized with H-296, and the control group without the immobilization showed a low proliferation rate as compared to these. In other words, it was clarified that the cell proliferation rate was enhanced by using H296-H296 or H-296 during the induction of CTLs, and that one in which H296-H296 was used gave an even higher effect.

Example 10

Assay of Cytotoxic Activity of CTLs of Example 9

The specific cytotoxic activity of CTLs for the CTLs obtained in Example 9 was assayed in the same manner as in Example 4. The results are shown in Table 9.

TABLE 9

| Sample | Cytotoxic Activity (%) After Induction of CTLs E/T Ratio | | | |
|---|---|---|---|---|
| | 30 | 10 | 3 | 1 |
| Control | n.t. | 54.4 | 24.4 | 5.8 |
| H296-H296 | 66.9 | 59.2 | 32.8 | 9.9 |
| H-296 | 62.9 | 57.4 | 32.6 | 8.6 | n.t.: not tested

The cytotoxic activity against the Calcein-labeled target cells cultured in the absence of the peptide was almost 0%, confirming that the non-specific activity was not found therefor. Regarding the cytotoxic activity against the Calcein-labeled target cells cultured in the presence of the peptide, the CTLs of the group immobilized with H296-H296 or H-296 during the induction maintained specific, high cytotoxic activities, as compared to the CTLs of the control group. In other words, the induction of CTLs having high cytotoxic activities could be carried out by using H296-H296 or H-296 during the induction of CTLs.

Example 11

Determination of Content Ratio of TCR Vβ17-Positive Cells in Cell Population of CTLs of Example 9

The content ratio of TCR Vβ17-positive cells was determined for the CTLs in an amount of $2 \times 10^5$ cells prepared in Example 9 in the same manner as in Example 5. The results are shown in Table 10. Incidentally, the content ratio of the Vβ17-positive cells of the responder cells before the induction of CTLs was 2.5%.

TABLE 10

| Sample | Content Ratio (%) of TCR Vβ17-Positive Cells |
|---|---|
| Control | 50.6 |
| H296-H296 | 73.5 |
| H-296 | 73.2 |

The group in which H296-H296 or H-296 was used during the induction showed a high content ratio of positive cells, as compared to the control group without use. In other words, it was clarified that the anti-influenza virus memory CTLs could be efficiently induced by using H296-H296 or H-296 during the induction.

Example 12

Expansion of CTLs of Example 9 Without Using Feeder Cells (1) Immobilization of Anti-CD3 Antibody and H296-H296 or H-296

H296-H296 or H-296 was immobilized to a culture equipment used in the following experiment for the expansion of CTLs without using the feeder cells. Concretely, PBS containing an anti-CD3 antibody (final concentration: 5 µg/mL) and H296-H296 or H-296 (final concentration: 25 µg/mL) was added to a 96-well cell culture plate in a volume of 160 µL/well each, and the mixture was incubated overnight at 4° C. (the control being immobilized only with the anti-CD3 antibody). In addition, the above-mentioned plate was washed twice with PBS before use, and then washed once with the RPMI 1640.

(2) Expansion of CTLs Without Using Feeder Cells

CTLs which had been induced in the presence of H296-H296 or H-296 (the control being CTLs induced in its absence) prepared in Example 9 were washed with 5HRPMI, the $1 \times 10^5$ cells were then suspended in 300 µL of 5HRPMI, and the culture was initiated in a humidified $CO_2$ incubator at 37° C. using the 96-well culture plate prepared in Example 12-(1). On the first day of the initiation of the culture, IL-2 was added thereto so as to have a final concentration of 500 U/mL, and on the fifth day and on from the initiation of the culture, subculture was carried out with a plate without the immobilization using 5HRPMI, and IL-2 having a final concentration of 500 U/mL was added thereto. In other words, the subculture was carried out at a concentration of $1 \times 10^5$ cells/ mL on the fifth day from the initiation of the culture, a concentration of $1.5\times10^5$ cells/mL on the eighth day, and a concentration of $3.2\times10^5$ cells/mL on the twelfth day. Stimulation by a peptide was not added at all during this culture, and the expansion was carried out for 15 days. The cell proliferation rate is shown in Table 11.

TABLE 11

| Sample | Cell Proliferation Rate (fold) | |
| --- | --- | --- |
| | During the Expansion | from the Induction |
| Control | 1.2 | 1.3 |
| H296-H296 | 56.0 | 240.8 |
| H-296 | 34.0 | 109.1 |

The group immobilized with H296-H296 during the induction and the expansion showed the highest proliferation rate, followed by the group immobilized with H-296 during the induction and the expansion, and the control group without the immobilization showed the lowest proliferation rate. In other words, it is clarified that the expansion of the CTLs could be carried out without using the feeder cells, by using H296-H296 or H-296 during the induction and the expansion, and the effect was higher for one in which H296-H296 was used.

Example 13

Assay of Cytotoxic Activity of CTLs of Example 12

The specific cytotoxic activity of CTLs for the CTLs obtained in Example 12-(2) was assayed in the same manner as in Example 4. The results are shown in Table 12. Here, no test was conducted for E/T ratio 30.

TABLE 12

| Sample | Cytotoxic Activity (%) After Expansion of CTLs E/T Ratio | | | Effect of Activity Maintenance (%) |
| --- | --- | --- | --- | --- |
| | 10 | 3 | 1 | E/T = 3 |
| Control | n.t. | n.t. | −0.4 | n.t. |
| H296-H296 | 65.5 | 41.5 | 16.8 | 126.4 |
| H-296 | 34.6 | 12.4 | 3.7 | 38.1 | n.t.: not tested

The cytotoxic activity against the Calcein-labeled target cells cultured in the absence of the peptide was almost 0%, confirming that the non-specific activity was not found therefor. Regarding the cytotoxic activity against the Calcein-labeled target cells cultured in the presence of the peptide, the CTLs of the group with addition of H296-H296 during the induction and the expansion maintained specific, high cytotoxic activities even after the expansion for 15 days. In addition, the CTLs of the group with the addition of H-296 during the induction and the expansion maintained specific cytotoxic activity, though being lower than the group with the addition of H296-H296. In other words, it was clarified that the expansion could be carried out according to a method without using feeder cells, in a state that a specific cytotoxic activity was maintained for a long period of time by using H296-H296 or H-296 during the induction and the expansion of CTLs, and a higher effect was obtained for that of H296-H296.

Example 14

Determination of Content Ratio of TCR Vβ17-Positive Cells in Cell Population of CTLs of Example 12

The content ratio of TCR Vβ17-positive cells was determined for the CTLs in an amount of $2\times10^5$ cells prepared in Example 12-(2) in the same manner as in Example 5. The results are shown in Table 13.

TABLE 13

| Sample | Content Ratio (%) of TCR Vβ17-Positive Cells |
| --- | --- |
| Control | 13.2 |
| H296-H296 | 83.1 |
| H-296 | 16.4 |

The group in which H296-H296 was used during the induction and the expansion showed the highest content ratio of positive cells, followed by the group in which H-296 was used during the induction and the expansion, and the control group without the immobilization showed the lowest content ratio of the positive cells. Here, the content ratio of the CTLs after the induction, in other words, TCR Vβ17-positive cells before the expansion, was 50.6% for the control group, 73.5% for the group immobilized with H296-H296, and 73.2% for the group immobilized with H-296. In other words, it was found that the expansion could be carried out while maintaining a high content ratio of the anti-influenza virus memory CTLs in a system without using the feeder cells by using H296-H296 during the induction and the expansion.

Example 15

Expansion of CTLs of Example 9 Without Using Feeder Cells Assuming 30 mL of Blood Collection (1) Immobilization of Anti-CD3 Antibody and H296-H296 or CH-296 Fragment H296-H296 or CH-296 was immobilized to a culture equipment used in the following experiment for the expansion of CTLs without using the feeder cells. Concretely, PBS containing an anti-CD3 antibody (final concentration: 5 μg/mL) and H296-H296 or CH-296 (final concentration: 25 μg/mL) was added to a 96-well cell culture plate in a volume of 160 μL/well each, and the mixture was incubated overnight at 4° C. (the control being immobilized only with the anti-CD3 antibody). In addition, the above-mentioned plate was washed twice with PBS before use, and then washed once with the RPMI medium.

(2) Expansion of CTLs Without Using Feeder Cells

CTLs which had been induced using H296-H296 in Example 9 were washed with the RPMI 1640 medium containing 3% human AB serum, 1 mM sodium pyruvate, 2 mM L-glutamine, 1×NEAA Mixture, and 1% streptomycin-penicillin (hereinafter simply referred to as "3HRPMI"), the $1\times10^5$ cells were then suspended in 300 μL of 3HRPMI, the suspension was put in the 96-well culture plate prepared in Example 15-(1), and the culture was initiated in a humidified CO$_2$ incubator at 37° C. During the culture, in a culture scale using PBMCs in an amount of $3\times10^7$ cells assumed to be obtained from 30 mL of blood collection, the expansion was carried out by limiting the amount of human AB serum from the induction to the expansion to a maximum of 15 mL, and the amount of the RPMI medium used to a maximum of 10 L.

On the first day of the initiation of the culture, IL-2 having a final concentration of 500 U/mL was added thereto, and on the fifth day, the cells at a concentration of 1×10$^5$ cells/mL were subcultured in a plate without the immobilization using a 1% human AB serum-containing RPMI medium, and IL-2 having a final concentration of 500 U/mL was added thereto. On the eighth day from the initiation of culture, the cells at a concentration of 1.5×10$^5$ cells/mL were subcultured in a plate without the immobilization using the RPMI medium containing a 0.2% human AB serum, and IL-2 having a final concentration of 500 U/mL was added thereto, and on the twelfth day, only IL-2 having a final concentration of 500 U/mL was added thereto. Stimulation by a peptide was not added at all during this culture, and the expansion was carried out for 15 days. The cell proliferation rate is shown in Table 14.

TABLE 14

| Sample | Cell Proliferation Rate (fold) | |
|---|---|---|
| | During the Expansion | from the Induction |
| Control | 35.3 | 151.7 |
| H296-H296 | 56.7 | 243.6 |
| CH-296 | 50.8 | 218.9 |

The CTLs of the group immobilized with H296-H296 or CH-296 during the expansion showed a higher proliferation rate than the group without the immobilization with H296-H296 or CH-296 during the expansion. In other words, the CTLs obtained using H296-H296 during the induction showed a high cell proliferation effect by using H296-H296 or CH-296 during the expansion.

Example 16

Induction of CTLs Having Specific Cytotoxic Activity Using H296-H296 (Self-Plasma)

Using the PBMCs isolated and stored according to the method described in Example 2-(1), the induction of the anti-influenza virus memory CTLs was carried out in the same manner as in Example 2-(3). During the induction, the RPMI medium containing 5% self plasma, 1 mM sodium pyruvate, 2 mM L-glutamine, the 1×NEAA Mixture, and 1% streptomycin-penicillin (hereinafter simply referred to as "5Plasma RPMI") was used. The cell proliferation rate on the fourteenth day from the initiation of the induction thus prepared is shown in Table 15.

TABLE 15

| Sample | Cell Proliferation Rate (fold) |
|---|---|
| Control | 1.7 |
| H296-H296 | 4.1 |

In the group immobilized with H296-H296 during the induction, a higher proliferation rate was obtained than the control group without the immobilization of H296-H296. In other words, it was clarified that in the medium containing self-plasma, the proliferation rate of the cells could be enhanced by using H296-H296 during the induction of the CTLs.

Example 17

Determination of Content Ratio of TCR Vβ17-Positive Cells in Cell Population of CTLs of Example 16

The content ratio of TCR Vβ17-positive cells was determined for the CTLs in an amount of 2×10$^5$ cells prepared in Example 16 in the same manner as in Example 5. The results are shown in Table 16. Incidentally, the content ratio of the Vβ17-positive cells of the responder cells before the induction of CTLs was 2.5%.

TABLE 16

| Sample | Content Ratio (%) of TCR Vβ17-Positive Cells |
|---|---|
| Control | 72.1 |
| H296-H296 | 80.1 |

The group immobilized with H296-H296 during the induction showed a high content ratio of positive cells, as compared to the control group without the immobilization with H296-H296. In other words, it was clarified that the anti-influenza virus memory CTLs could be efficiently induced by using H296-H296 during the induction.

Example 18

Expansion of CTLs of Example 16 Using Feeder Cells

Using the CTLs induced in the presence of H296-H296 prepared in Example 16 (the control being CTLs induced in the absence of H296-H296), the expansion of CTLs was carried out in the same manner as in Example 3. During the expansion, the culture was carried out using the 5Plasma RPMI medium, and the expansion was carried out for 14 days. The cell proliferation rate after 14 days is shown in Table 17.

TABLE 17

| Sample | Cell Proliferation Rate (fold) | |
|---|---|---|
| | During the Expansion | from the Induction |
| Control | 276.5 | 468.7 |
| H296-H296 | 337.8 | 1380.7 |

The group immobilized with H296-H296 during the induction and the expansion showed a higher proliferate rate than the group without the immobilization of H296-H296. In other words, it was clarified that the proliferation rate of the cells was enhanced by using H296-H296 during the induction or the expansion.

Example 19

Assay of Cytotoxic Activity of CTLs of Example 18

The specific cytotoxic activity of CTLs for the CTLs obtained in Example 18 was assayed in the same manner as in Example 4. The results are shown in Table 18.

TABLE 18

| | Cytotoxic Activity (%) After Expansion of CTLs E/T Ratio | | | | Effect of Activity Maintenance (%) |
|---|---|---|---|---|---|
| Sample | 30 | 10 | 3 | 1 | E/T = 3 |
| Control | 52.6 | 24.1 | 9.5 | 5.2 | 18.0 |
| H296-H296 | 88.6 | 83.2 | 57.7 | 26.9 | 117.0 |

The cytotoxic activity against the Calcein-labeled target cells cultured in the absence of the peptide was almost 0%, confirming that the non-specific activity was not found therefor. Regarding the cytotoxic activity against the Calcein-labeled target cells cultured in the presence of the peptide, the group immobilized with H296-H296 during the induction and the expansion maintained specific, high cytotoxic activities even after the expansion for 14 days. On the other hand, regarding the control group without the immobilization of H296-H296 during the induction and the expansion, its activity was clearly lowered. In other words, it was clarified that in the expansion using self-plasma, the expansion of the CTLs could be carried out in a state that a specific, high cytotoxic activity was maintained for a long period of time, by using H296-H296 during the induction and the expansion of CTLs.

Example 20

Determination of Content Ratio of TCR Vβ17-Positive Cells in Cell Population of CTLs of Example 18

The content ratio of TCR Vβ17-positive cells was determined for the CTLs in an amount of $2 \times 10^5$ cells prepared in Example 18 in the same manner as in Example 5. The results are shown in Table 19.

TABLE 19

| Sample | Content Ratio (%) of TCR Vβ17-Positive Cells |
|---|---|
| Control | 8.6 |
| H296-H296 | 62.0 |

The group immobilized with H296-H296 during the induction and the expansion clearly showed a high content ratio of positive cells, as compared to the control group without the immobilization. Here, the content ratio of TCR Vβ17-positive cells for the CTLs after the induction, in other words, those before the expansion is, as shown in Table 16, 80.1% for the group immobilized with H296-H296, and 72.1% for the group without the immobilization. In other words, in the expansion using self-plasma, it was clarified that the expansion could be carried out while maintaining a high content ratio of the anti-influenza virus memory CTLs, by using H296-H296 during the induction and the expansion of CTLs.

Example 21

Expansion of Lymphocytes (Lymphokine-Activated Cells) Using H296-H296

(1) Isolation and Storage of PBMCs

Apheresis was performed on a human healthy donor, obtained with informed consent. The collected blood was then diluted 2-folds with phosphate buffered saline (PBS), overlaid on Ficoll-paque, and centrifuged at 500×g for 20 minutes. The peripheral blood mononuclear cells (PBMCs) in the intermediate layer were collected with a pipette, and washed. The collected PBMCs were suspended in a storage solution of 90% FBS/10% DMSO (manufactured by SIGMA), and stored in liquid nitrogen. Upon the expansion of the lymphocytes, these stored PBMCs were rapidly thawed in water bath at 37° C., and washed with the RPMI 1640 medium containing 10 μg/mL DNase. Thereafter, the number of viable cells was counted by trypan blue staining method, and the cells were subjected to each experiment.

(2) Immobilization of Anti-Human CD3 Antibody and H296-H296 Fragment

An anti-human CD3 antibody and H296-H296 were immobilized to a culture equipment used in the following experiment. Concretely, PBS containing an anti-human CD3 antibody (final concentration: 5 μg/mL) and H296-H296 (final concentration: 25 μg/mL) was added to a 12-well cell culture plate (manufactured by Becton, Dickinson and Company) in a volume of 1.9 mL/well each. During the addition, to the group with addition of H296-H296 was added H296-H296 prepared in Example 1 so as to have a final concentration (25 μg/mL).

After these culture equipments were incubated at room temperature for 5 hours, the culture equipments were stored at 4° C. until use. Immediately before use, PBS containing the antibody and H296-H296 was removed by aspiration from these culture equipments, and thereafter each well was washed twice with PBS, and then once with the RPMI medium, and the culture equipments were subjected to each experiment.

(3) Expansion of Lymphocytes

PBMCs which were prepared in Example 21-(1) were suspended in AIM-V (manufactured by Invitrogen) containing 3% human AB serum (hereinafter simply referred to as "3% AIM-V"), so as to have a concentration of $1 \times 10^6$ cells/mL. Thereafter, the 3% AIM-V was added to a plate immobilized with the anti-human CD3 antibody or a plate immobilized with the anti-human CD3 antibody and the H296-H296, prepared in Example 21-(2), in a volume of 2 mL/well, and the cell suspension was added thereto in a volume of 1 mL/well each. IL-2 was added thereto so as to have a final concentration of 1000 U/mL, and these plates were subjected to culture at 37° C. in 5% $CO_2$ (zeroth day of culture). On the fourth day from the initiation of culture, each group was diluted with AIM-V containing 1% human AB serum so as to have a concentration of $0.075 \times 10^6$ cells/mL (volume of culture medium: 6 mL), and the diluted culture medium was transferred to a 12.5 cm²-cell culture flask to which nothing was immobilized, and IL-2 was added thereto so as to have a final concentration of 500 U/mL. The serum concentration was determined assuming that the PBMCs obtained from the 30 mL blood collection were cultured in 10 L of the medium. The culture was continued, and on the seventh day, to a 25 cm²-cell culture flask (standing culture) to which nothing was immobilized was transferred a culture medium diluted with AIM-V containing 0.1% human AB serum in the control group (without immobilization with H296-H296), and that diluted with AIM-V containing 0.09% human AB serum (volume of the culture medium: 12.6 mL) in the group with immobilization of H296-H296, so as to have a concentration of $0.25 \times 10^6$ cells/mL in each group. To both the groups, IL-2 was added so as to have a final concentration of 500 U/mL On the tenth day from the initiation of the culture, the cell suspension was diluted with AIM-V containing the human AB serum of the same serum concentration (volume of culture medium: 12.6 mL) as that of the seventh day so as to have a concentration of $0.413 \times 10^6$/mL, and each dilution was transferred to a fresh 25 cm²-cell culture flask (standing culture) to which nothing was immobilized. To each group, IL-2 was added so as to have a final concentration of 500 U/mL. On the fifteenth day from the initiation of culture, the number of viable cells was counted by trypan blue staining method, and an expansion fold was calculated by comparing the number of the counted cells with the number of cells at the initiation of culture. The results are shown in Table 20.

TABLE 20

| Serum Concentration (%) | Cultured Days | Sample | Expansion Fold (fold) |
|---|---|---|---|
| 3 → 1 → 0.1 | 15 Days | Control (Without Immobilization of H296-H296) | 343 |
| 3 → 1 → 0.09 | 15 Days | H296-H296 | 498 |

As shown in Table 20, the group in which the culture equipment immobilized with H296-H296 at an early stage of the expansion of the lymphocytes was used had a high expansion fold of the lymphocytes as compared to the control group. It was clarified from this matter that H296-H296 is suitably used during the expansion of the lymphocytes.

Example 22

Generation of H296-H296-H296-HT (1) Construction of H296-H296-H296-HT Expression Vector In order to allow expression of a modified fibronectin fragment (H296-H296-H296-HT) in which three H-296's were connected, an expression vector was constructed in the manner described below.

(i) Construction of H296-HT Expression Vector

From the nucleotide sequence of CH-296 (SEQ ID NO: 8 of Sequence Listing), a synthetic primer H296-NdeF having the nucleotide sequence shown in SEQ ID NO: 14 of Sequence Listing was synthesized with a DNA synthesizer, and purified according to a conventional method. The above-mentioned synthetic primer H296-NdeF is a synthetic DNA having a recognized sequence with a restriction enzyme NdeI in the base numbers 9-14, and further having a nucleotide sequence corresponding to amino acid numbers 278-285 of the amino acid sequence of CH-296 in the base numbers 12-35.

PCR was carried out using the above-mentioned synthetic primer and a synthetic primer H296-HindR. The reaction conditions for PCR are given hereinafter. Concretely, about 0.1 µg of pCH102 as a template DNA, 5 µL of the 10× Ex Taq Buffer, 5 µL of the dNTP mixture, 10 pmol of a synthetic primer H296-NdeF, 10 pmol of a synthetic primer H296-HindR, and 0.5 U TaKaRa Ex Taq were added together, and a sterile water was added thereto to make up a total volume of 50 µL. The above reaction mixture was set in the TaKaRa PCR Thermal Cycler SP, and 30 cycles of reaction, each cycle comprising 94° C. for 1 minute, 55° C. for 1 minute, and 72° C. for 3 minutes, were performed. After the termination of the reaction, 5 µL of the reaction mixture was electrophoresed with 1.0% agarose gel, and a desired DNA fragment having a size of about 0.9 kbp was confirmed. The remainder of the reaction mixture for PCR was electrophoresed, and a fragment thereof was collected and purified, and the purified mixture was subjected to ethanol precipitation. The DNA collected after the ethanol precipitation was suspended in 10 µL of a sterile water, and subjected to a double digestion with a restriction enzyme NdeI (manufactured by TAKARA BIO, INC.) and a restriction enzyme HindIII, and the digest was electrophoresed with 1.0% agarose gel, thereby extracting and purifying the NdeI, HindIII digest, to give an NdeI-HindIII-digested DNA fragment.

Next, pColdI vector (manufactured by TAKARA BIO, INC.) was digested with the restriction enzymes NdeI and HindIII to prepare a product, and the product was mixed with the above-mentioned NdeI-HindIII-digested DNA fragment, and ligated with the DNA ligation kit. Thereafter, *Escherichia coli* JM109 was transformed with 20 µL of the ligation reaction mixture, and the resulting transformant was grown on an LB medium (containing 50 µg/mL ampicillin) containing agar in a concentration of 1.5% (w/v). A recombinant plasmid inserted with the desired DNA fragment was referred to as pColdI-H296.

(ii) Construction of H296-H296-H296-HT Expression Vector

Next, from the nucleotide sequence of CH-296 (SEQ ID NO: 8 of Sequence Listing), a synthetic primer H296-NdeR having the nucleotide sequence shown in SEQ ID NO: 15 of Sequence Listing was synthesized with a DNA synthesizer, and purified according to a conventional method. The above-mentioned synthetic primer H296-NdeR is a synthetic DNA having a recognized sequence with a restriction enzyme NdeI in the base numbers 4-9, and further having a nucleotide sequence corresponding to amino acid numbers 574-569 of the amino acid sequence of CH-296 (SEQ ID NO: 7 of Sequence Listing) in the base numbers 10-27.

PCR was carried out using the above-mentioned synthetic primer and a synthetic primer H296-NdeF. The reaction conditions for PCR are given hereinafter. Concretely, about 0.1 µg of pCH102 as a template DNA, 5 µL of the 10× Ex Taq Buffer, 5 µL of the dNTP mixture, 10 pmol of a synthetic primer H296-NdeF, 10 pmol of a synthetic primer H296-NdeR, and 0.5 U TaKaRa Ex Taq were added together, and a sterile water was added thereto to make up a total volume of 50 µL. The above reaction mixture was set in the TaKaRa PCR Thermal Cycler SP, and 30 cycles of reaction, each cycle comprising 94° C. for 1 minute, 55° C. for 1 minute, and 72° C. for 3 minutes, were performed. After the termination of the reaction, 5 µL of the reaction mixture was electrophoresed with 1.0% agarose gel, and a desired DNA fragment having a size of about 0.9 kbp was confirmed. The remainder of the reaction mixture for PCR was electrophoresed, and a fragment thereof was collected and purified, and the purified mixture was subjected to ethanol precipitation. The DNA collected after the ethanol precipitation was suspended in 10 µL of a sterile water, and digested with a restriction enzyme NdeI, the digest was ligated using the DNA ligation kit, and the resulting DNA fragment having a size of 1.8 kbp or more was then extracted and purified by electrophoresing on 1.0% agarose gel.

Next, the above-mentioned pColdI-H296 was digested with NdeI, and the terminals of the products were subjected to a dephosphorization treatment to prepare a product, and the product was mixed with the above-mentioned DNA fragment, and ligated using the DNA ligation kit. Thereafter, *Escherichia coli* JM109 was transformed with 20 µL of the ligation reaction mixture, and the resulting transformant was grown on an LB medium (containing 50 µg/mL ampicillin) containing agar in a concentration of 1.5% (w/v).

The desired plasmid inserted with a DNA fragment encoding a protein in which three H-296's were connected was confirmed by sequencing, and this recombinant plasmid was referred to as pColdI-H296-3. This pColdI-H296-3 is a plasmid containing a DNA sequence encoding a polypeptide in which three nucleotide sequences encoding the amino acid sequence of the amino acid numbers 278-574 of CH-296 are connected with an amino acid "H" inserted therebetween, the polypeptide having a His tag sequence at an N-terminal thereof. The protein is named H296-H296-H296-HT, and an amino acid sequence thereof is shown in SEQ ID NO: 16 of Sequence Listing, and a nucleotide sequence thereof is shown in SEQ ID NO: 17 of Sequence Listing.

(2) Expression and Purification of H296-H296-H296-HT

*Escherichia coli* BL21 was transformed with pColdI-H296-3 prepared in the above-mentioned (1), and the resulting transformant was grown on LB medium (containing 50 μg/mL ampicillin) containing agar having a concentration of 1.5% (w/v). The obtained colonies were inoculated to 200 mL of LB liquid medium (containing 50 μg/mL ampicillin), and cultured at 37° C. until OD reached 0.4 to 0.6 (about 5 to 8 hours). Thereafter, the culture medium was cooled to 15° C., IPTG was then added so as to have a final concentration of 1.0 mM, and the cells were cultured in this state at 15° C. for 24 hours to induce expression. Thereafter, the cells were harvested by centrifugation, and suspended in about 10 mL of Binding Buffer [50 mM Tris-HCl (pH 8.5), 150 mM NaCl, 1 mM MgCl$_2$]. Thereafter, the cells were disrupted by ultrasonic disruption, and the disruption was centrifuged (11,000 r/min for 20 minutes), to give an extract of the supernatant. The extract of the supernatant obtained was added to 2 mL of Ni-NTA resin, and the mixture was stirred at 4° C. for 1 hour. Thereafter, the resin was sequentially treated with 10 mL of the Binding Buffer, 10 mL of Washing Buffer A [20 mM Tris-HCl (pH 8.5), 100 mM NaCl, 1 mM MgCl$_2$, 10% glycerol, 20 mM Imidazole], 10 mL of Washing Buffer B [20 mM Tris-HCl (pH 8.5), 800 mM NaCl, 1 mM MgCl$_2$, 10% glycerol, 20 mM Imidazole], and 10 mL of the Washing Buffer A. Thereafter, the target protein to which the resin was bound was eluted with 3 mL of Elution Buffer [20 mM Tris-HCl (pH 8.5), 100 mM NaCl, 1 mM MgCl$_2$, 10% glycerol, 200 mM Imidazole]. The eluate obtained was concentrated to a volume of 0.3 mL using a Viva column (manufactured by Sartorius). The concentrate obtained was analyzed by SDS-PAGE, and as a result, a target protein having a molecular weight of about 99 kDa was detected in a nearly single band. Thereafter, the concentration of the protein was determined with the MicroBCA kit, and as a result, the concentration was 2.5 mg/mL (about 25 μM, calculated from the molecular weight).

Example 23

Generation of CH296-CH296-HT

In order to allow expression of a modified fibronectin fragment (CH296-CH296-HT) in which two CH-296's were connected, an expression vector was constructed in the manner described below.

(1) Construction of CH296-CH296-HT Expression Vector (i) Construction of CH296-HT Expression Vector From the nucleotide sequence of CH-296, a synthetic primer CH296-NdeF having the nucleotide sequence shown in SEQ ID NO: 18 of Sequence Listing was synthesized with a DNA synthesizer, and purified according to a conventional method. The above-mentioned synthetic primer CH296-NdeF is a synthetic DNA having a recognized sequence with a restriction enzyme NdeI in the base numbers 9-14, and further having a nucleotide sequence corresponding to amino acid numbers 1-6 of the amino acid sequence of CH-296 in the base numbers 15-32.

PCR was carried out using the above-mentioned synthetic primer and a synthetic primer H296-HindR. The reaction conditions for PCR are given hereinafter. Concretely, about 0.1 μg of pCH102 as a template DNA, 5 μL of the 10× Ex Taq Buffer, 5 μL of the dNTP mixture, 10 pmol of a synthetic primer CH296-NdeF, 10 pmol of a synthetic primer H296-HindR, and 0.5 U TaKaRa Ex Taq were added together, and a sterile water was added thereto to make up a total volume of 50 μL. The above reaction mixture was set in the TaKaRa PCR Thermal Cycler SP, and 30 cycles of reaction, each cycle comprising 94° C. for 1 minute, 55° C. for 1 minute, and 72° C. for 3 minutes, were performed. After the termination of the reaction, 5 μL of the reaction mixture was electrophoresed with 1.0% agarose gel, and a desired DNA fragment having a size of about 1.7 kbp was confirmed. The remainder of the reaction mixture for PCR was electrophoresed, and a fragment thereof was collected and purified, and the purified mixture was subjected to ethanol precipitation. The DNA collected after the ethanol precipitation was suspended in 10 μL of a sterile water, and subjected to a double digestion with a restriction enzyme NdeI and a restriction enzyme HindIII, and the digest was electrophoresed with 1.0% agarose gel, thereby extracting and purifying the NdeI, HindIII digest, to give an NdeI-HindIII-digested DNA fragment.

Next, the pColdI vector was digested with NdeI and HindIII to prepare a product, and the product was mixed with the above-mentioned NdeI-HindIII-digested DNA fragment, and ligated with the DNA ligation kit. Thereafter, *Escherichia coli* JM109 was transformed with 20 μL of the ligation reaction mixture, and the resulting transformant was grown on an LB medium (containing 50 μg/mL ampicillin) containing agar in a concentration of 1.5% (w/v). A recombinant plasmid inserted with the desired DNA fragment was referred to as pColdI-CH296.

(ii) Construction of CH296-CH296-HT Expression Vector

PCR was carried out using a synthetic primer CH296-NdeF and a synthetic primer H296-NdeR. The reaction conditions for PCR are given hereinafter. Concretely, about 0.1 μg of pCH102 as a template DNA, 5 μL of 10× Ex Taq Buffer, 5 μL of the dNTP mixture, 10 pmol of a synthetic primer CH296-NdeF, 10 pmol of a synthetic primer H296-NdeR, and 0.5 U TaKaRa Ex Taq were added together, and a sterile water was added thereto to make up a total volume of 50 μL. The above reaction mixture was set in the TaKaRa PCR Thermal Cycler SP, and 30 cycles of reaction, each cycle comprising 94° C. for 1 minute, 55° C. for 1 minute, and 72° C. for 3 minutes, were performed.

After the termination of the reaction, 5 μL of the reaction mixture was electrophoresed with 1.0% agarose gel, and a desired DNA fragment having a size of about 1.7 kbp was confirmed. The remainder of the reaction mixture for PCR was electrophoresed, and a fragment thereof was collected and purified, and the purified mixture was subjected to ethanol precipitation. The DNA collected after the ethanol precipitation was suspended in 10 μL of a sterile water, and digested with a restriction enzyme NdeI, and a desired DNA fragment having a size of 1.7 kbp was extracted and purified by electrophoresing on 1.0% agarose gel.

Next, pColdI-CH296 was digested with NdeI, and the terminals of the products were subjected to a dephosphorization treatment to prepare a product, and the product was mixed with the above-mentioned DNA fragment, and ligated using the DNA ligation kit. Thereafter, *Escherichia coli* JM109 was transformed with 20 μL of the ligation reaction mixture, and the resulting transformant was grown on an LB medium (containing 50 μg/mL ampicillin) containing agar in a concentration of 1.5% (w/v).

The desired plasmid inserted with a DNA fragment encoding a protein in which two CH-296's were connected was confirmed by sequencing, and this recombinant plasmid was referred to as pColdI-CH296-2. This pColdI-CH296-2 is a plasmid containing a DNA sequence encoding a polypeptide in which two nucleotide sequences encoding the amino acid sequence of the amino acid numbers 1-574 of CH-296 added with methionine at the N-terminal are connected with an amino acid "H" inserted therebetween, the polypeptide having a His tag sequence at an N-terminal thereof. The protein is named CH296-CH296-HT, and an amino acid sequence thereof is shown in SEQ ID NO: 19 of Sequence Listing, and a nucleotide sequence thereof is shown in SEQ ID NO: 20 of Sequence Listing.

(2) Expression and Purification of CH296-CH296-HT

*Escherichia coli* BL21 was transformed with pColdI-CH296-2 prepared in the above-mentioned (1), and the expression and purification of CH296-CH296-HT were carried out in the same manner as in Example 22-(2). The concentrate obtained was analyzed by SDS-PAGE, and as a result, a target protein having a molecular weight of about 128 kDa was detected in a nearly single band. Thereafter, the concentration of the protein was determined with the MicroBCA kit, and as a result, the concentration was 3.1 mg/mL (about 24 µM, calculated from the molecular weight).

Example 24

Generation of H105-H105-HT (1) Construction of H105-H105-HT Expression Vector

In order to allow expression of a modified fibronectin fragment (H105-H105-HT) in which two H-105's were connected, wherein a polypeptide consisting of the amino acids 460-574 (base numbers 1381-1725) from the N-terminal side of the amino acid sequence of CH-296 is referred to as H-105, an expression vector was constructed in the manner described below.

(i) Construction of H105-HT Expression Vector

From the nucleotide sequence of CH-296, a synthetic primer H105-NdeF having the nucleotide sequence shown in SEQ ID NO: 21 of Sequence Listing was synthesized with a DNA synthesizer, and purified according to a conventional method. The above-mentioned synthetic primer H105-NdeF is a synthetic DNA having a recognized sequence with a restriction enzyme NdeI in the base numbers 9-14, and further having a nucleotide sequence corresponding to amino acid numbers 460-466 of the amino acid sequence of CH-296 in the base numbers 15-35.

PCR was carried out using the above-mentioned synthetic primer and H296-HindR. The reaction conditions for PCR are given hereinafter. Concretely, about 0.1 µg of pCH102 as a template DNA, 5 µL of 10× Ex Taq Buffer (manufactured by TAKARA BIO, INC.), 5 µL of a dNTP mixture (manufactured by TAKARA BIO, INC.), 10 pmol of a synthetic primer H105-NdeF, 10 pmol of a synthetic primer H296-HindR, and 0.5 U TaKaRa Ex Taq (manufactured by TAKARA BIO, INC.) were added together, and a sterile water was added thereto to make up a total volume of 50 µL. The above reaction mixture was set in TaKaRa PCR Thermal Cycler SP (manufactured by TAKARA BIO, INC.), and 30 cycles of reaction, each cycle comprising 94° C. for 1 minute, 55° C. for 1 minute, and 72° C. for 3 minutes, were performed. After the termination of the reaction, 5 µL of the reaction mixture was electrophoresed with 1.0% agarose gel, and a desired DNA fragment having a size of about 0.35 kbp was confirmed. The remainder of the reaction mixture for PCR was electrophoresed, and a fragment thereof was collected and purified, and the purified mixture was subjected to ethanol precipitation. The DNA collected after the ethanol precipitation was suspended in 10 µL of a sterile water, and subjected to a double digestion with a restriction enzyme NdeI (manufactured by TAKARA BIO, INC.) and a restriction enzyme HindIII (manufactured by TAKARA BIO, INC.), and the digest was electrophoresed with 1.0% agarose gel, thereby extracting and purifying the NdeI, HindIII digest, to give an NdeI-HindIII-digested DNA fragment.

Next, pColdI vector (manufactured by TAKARA BIO, INC.) was digested with NdeI and HindIII to prepare a product, and the product was mixed with the above-mentioned NdeI-HindIII-digested DNA fragment, and ligated with a DNA ligation kit (manufactured by TAKARA BIO, INC.). Thereafter, *Escherichia coli* JM109 was transformed with 20 µL of the ligation reaction mixture, and the resulting transformant was grown on an LB medium (containing 50 µg/mL ampicillin) containing agar in a concentration of 1.5% (w/v). A recombinant plasmid inserted with the desired DNA fragment was confirmed by sequencing and referred to as pColdI-H105. This pColdI-H105 is a plasmid containing a DNA sequence encoding a polypeptide having a His tag sequence and methionine at an N-terminal of a nucleotide sequence encoding the amino acid sequence of the amino acid numbers 460-574 of CH-296.

(ii) Construction of H105-H105-HT Expression Vector

PCR was carried out using H105-NdeF and H296-NdeR. The reaction conditions for PCR are given hereinafter. Concretely, about 0.1 µg of pCH102 as a template DNA, 5 µL of 10× Ex Taq Buffer (manufactured by TAKARA BIO, INC.), 5 µL of a dNTP mixture (manufactured by TAKARA BIO, INC.), 10 pmol of a synthetic primer H105-NdeF, 10 pmol of a synthetic primer H296-NdeR, and 0.5 U TaKaRa Ex Taq (manufactured by TAKARA BIO, INC.) were added together, and a sterile water was added thereto to make up a total volume of 50 µL. The above reaction mixture was set in TaKaRa PCR Thermal Cycler SP (manufactured by TAKARA BIO, INC.), and 30 cycles of reaction, each cycle comprising 94° C. for 1 minute, 55° C. for 1 minute, and 72° C. for 3 minutes, were performed.

After the termination of the reaction, 5 µL of the reaction mixture was electrophoresed with 1.0% agarose gel, and a desired DNA fragment having a size of about 0.35 kbp was confirmed. The remainder of the reaction mixture for PCR was electrophoresed, and a fragment thereof was collected and purified, and the purified mixture was subjected to ethanol precipitation. The DNA collected after the ethanol precipitation was suspended in 10 µL of a sterile water, and digested with a restriction enzyme NdeI (manufactured by TAKARA BIO, INC.), and a desired DNA fragment having a size of 0.35 kbp was extracted and purified by electrophoresing with 1.0% agarose gel.

Next, pColdI-H105 was digested with NdeI, and the terminals of the products were subjected to a dephosphorization treatment to prepare a product, and the product was mixed with the above-mentioned DNA fragment, and ligated using a DNA ligation kit (manufactured by TAKARA BIO, INC.). Thereafter, *Escherichia coli* JM109 was transformed with 20 µL of the ligation reaction mixture, and the resulting transformant was grown on an LB medium (containing 50 µg/ml ampicillin) containing agar in a concentration of 1.5% (w/v).

The desired plasmid inserted with a DNA fragment encoding a protein in which two H-105's were overlapped was confirmed by sequencing, and this recombinant plasmid was referred to as pColdI-H105-2. This pColdI-H105-2 is a plasmid containing a DNA sequence encoding a polypeptide in which two nucleotide sequences encoding the amino acid sequence of the amino acid numbers 460-574 of CH-296 are connected with an amino acid "HM" inserted therebetween, the polypeptide having a His tag sequence and methionine at an N-terminal thereof. The protein is named H105-H105-HT, and an amino acid sequence thereof is shown in SEQ ID NO: 22 of Sequence Listing, and a nucleotide sequence thereof is shown in SEQ ID NO: 23 of Sequence Listing.

(2) Expression and Purification of H105-H105-HT

*Escherichia coli* BL21 was transformed with pColdI-H105-2 prepared in the above-mentioned (1), and the expression and purification of H105-H105-HT were carried out in the same manner as in Example 22-(2). Here, the amounts of liquid volume of the culture medium, Binding Buffer, Washing Buffer A, Elution Buffer, and the concentrate were properly changed as occasion demands. The concentrate obtained was analyzed by SDS-PAGE, and as a result, a target protein having a molecular weight of about 28 kDa was detected in a nearly single band. Thereafter, the concentration of the protein was determined with the MicroBCA kit, and as a result, the concentration was 5.1 mg/mL (about 180 µM, calculated from the molecular weight).

Example 25

Induction of CTLs Having Specific Cytotoxic Activity Using FN Fragments (1) Immobilization of Each of FN Fragments Each of three kinds of FN Fragments, H296-H296, H296-H296-H296-HT, and CH296-CH296-HT, was immobilized to a culture equipment used in the following experiment. Concretely, PBS containing an FN fragment having a final concentration of from 4 to 25 µg/mL was added to the 24-well cell culture plate in a volume of 1 mL/well each, and the mixture was incubated overnight at 4° C. Here, as to the concentration of the FN fragment, the concentration of the FN fragments used was controlled in order to match the amount of each FN fragment immobilized to the culture equipment to a given level. The culture equipment was washed twice with PBS before use, and then washed once with the RPMI 1640 medium, and the culture equipments were subjected to each experiment.

(2) Induction of Anti-Influenza Virus Memory CTLs

Using the PBMCs isolated and stored according to the method described in Example 2-(1), the induction of the anti-influenza virus memory CTLs was carried out in the same manner as in Example 2-(3). During the induction, the plate used was the one prepared in Example 25-(1). H105-H105-HT was added to the wells prepared in the same manner as the control, so as to have a final concentration of 0.4 µg/mL (as the control, a plate without immobilization of the FN fragment being used), and the cells were cultured. The cell proliferation rate after 14 days of the culture is shown in Table 21.

TABLE 21

| FN Fragment | Cell Proliferation Rate (fold) |
| --- | --- |
| Control (Without Immobilization With FN Fragment) | 0.8 |
| H296-H296 | 2.3 |
| H296-H296-H296-HT | 1.5 |
| CH296-CH296-HT | 2.3 |
| H105-H105-HT | 1.8 |

The cell proliferation rate was defined by a ratio of the number of cells at the point of time of the termination of the induction to the number of responder cells at the initiation of the induction of CTLs as a proliferation rate. As a result, the groups in which the FN fragments were used showed high proliferation rates as compared to the control group without use of the FN fragment. In other words, it was clarified that the proliferation rates of the cells were enhanced by using the FN fragments during the induction of CTLs.

Example 26

Expansion Using Feeder Cells of CTLs Obtained in Example 25

(1) Immobilization of Each of FN Fragments

Each of three kinds of the FN Fragments was immobilized to a culture equipment used in the following experiment. Concretely, PBS containing an FN fragment having a final concentration of from 4 to 25 µg/mL was put in a 12.5 cm$^2$ flask (standing culture) in a volume of 2.7 mL each, and the mixture was incubated overnight at 4° C. Here, as to the concentration of the FN fragment, the concentration of the FN fragments used was controlled in order to match the amount of each FN fragment immobilized to the culture equipment to a given level. In addition, the above-mentioned flask was washed twice with PBS before use, and then washed once with the RPMI 1640 medium, and subjected to each experiment.

(2) Expansion Using Feeder Cells of CTLs Obtained in Example 25

The CTLs prepared in Example 25-(2) were subjected to expansion according to the method described in Example 3-(2). During the expansion, the cells were cultured in the 5HRPMI medium, one obtained by mixing three donors was used as feeder cells. In addition, as the culture equipment, a flask immobilized with each of the FN fragments in Example 26-(1) was used, and H105-H105-HT was added to a flask prepared in the same manner as that of the control so as to have a final concentration of 0.4 µg/mL (as the control, a flask without the immobilization being used), and the cells were cultured. The results are shown in Table 22.

TABLE 22

| | Cell Proliferation Rate (fold) | |
| --- | --- | --- |
| FN Fragment | During the Expansion | from the Induction |
| Control (Without Immobilization with FN Fragment) | 258.0 | 197.2 |
| H296-H296 | 313.3 | 712.5 |
| H296-H296-H296-HT | 250.0 | 363.1 |
| CH296-CH296-HT | 344.7 | 795.7 |
| H105-H105-HT | 254.7 | 464.3 |

The proliferation rate during the expansion was defined by a ratio of the number of cells at the point of time of the termination of the expansion to the number of cells at the initiation of the expansion as a proliferation rate, and the proliferation rate from the induction was defined by a ratio of the number of cells at the point of time of the termination of the expansion to the number of responder cells at the initiation of the induction as a proliferation rate. As a result, the CTLs of the groups immobilized with or solution-added with the FN fragments during the induction and the expansion of CTLs showed higher proliferation rates than the control group without using the FN fragments. In other words, it was clarified that the proliferation rates of the cells were enhanced by using the FN fragments during the induction and the expansion of CTLs.

Example 27

Assay of Cytotoxic Activity of CTLs Obtained in Example 26

The specific cytotoxic activity of CTLs for the CTLs obtained in Example 26-(2) was assayed in the same manner as in Example 4. During the assay, Calcein-labeled target cells were prepared using HLA-A2-having Lymphoblast (name of cell: T2:ATCC CRL-1992). The results for the cytotoxic activity after the expansion of CTLs are shown in Table 23, and the effects of activity maintenance are shown in Table 24. Here, as to the effects of maintaining the cytotoxic activity, the calculations were made on two points, E/T ratios of 3 and 1.

TABLE 23

| FN Fragment | Cytotoxic Activity (%) After Expansion of CTLs E/T Ratio | | | |
|---|---|---|---|---|
| | 30 | 10 | 3 | 1 |
| Control (Without Immobilization with FN Fragment) | 77.8 | 75.7 | 39.0 | 12.2 |
| H296-H296 | 90.6 | 85.5 | 62.7 | 34.0 |
| H296-H296-H296-HT | 83.4 | 80.3 | 56.7 | 22.5 |
| CH296-CH296-HT | 81.3 | 80.9 | 63.1 | 27.6 |
| H105-H105-HT | 86.0 | 84.0 | 65.3 | 36.5 |

TABLE 24

| FN Fragment | Effect of Activity Maintenance (%) E/T Ratio | |
|---|---|---|
| | 3 | 1 |
| Control (Without Immobilization with FN Fragment) | 49.2 | 29.7 |
| H296-H296 | 79.8 | 94.7 |
| H296-H296-H296-HT | 70.3 | 56.7 |
| CH296-CH296-HT | 87.3 | 92.1 |
| H105-H105-HT | 90.9 | 116.8 |

The cytotoxic activity against the Calcein-labeled target cells cultured in the absence of the peptide was almost 0%, confirming that the non-specific activity was not found therefor. In the cytotoxic activity against the Calcein-labeled target cells cultured in the presence of the peptide, the groups in which the FN fragments were used during the induction and the expansion of CTLs maintained specific, high cytotoxic activities even after the expansion for 14 days. On the other hand, in the control group without using the FN fragments in both during the induction and the expansion of CTLs, its activity was clearly lowered. In other words, it was clarified that the expansion of CTLs could be carried out in a state that a specific, high cytotoxic activity was maintained for a long period of time, by using the FN fragments during the induction and the expansion of CTLs.

Example 28

Determination of Content Ratio of TCR Vβ17-Positive-CD8-Positive Cells in Cell Population of CTLs Obtained in Example 26

The CTLs in an amount of $2 \times 10^5$ cells which were prepared in Example 26-(2) were washed with PBS, and the cells were suspended in 15 µL of PBS containing 1% BSA, FITC-labeled mouse IgG1/RD1-labeled mouse IgG1/PC5-labeled mouse IgG1 or FITC-labeled mouse anti-human TCR Vβ17 antibody and RD1-labeled mouse anti-human CD8 (manufactured by BECKMAN COULTER) was added thereto as a negative control, and the mixture was then incubated on ice for 30 minutes. After the incubation, the cells were washed twice with PBS containing 0.1% BSA, and suspended in PBS containing 0.1% BSA. These cells were subjected to flow cytometry using Cytomics FC500, and the content ratio of TCR Vβ17-positive-CD8-positive cells was determined. The determination results are shown in Table 25.

TABLE 25

| FN Fragment | TCR Vβ17+ CD8+ (%) |
|---|---|
| Control (Without Immobilization with FN Fragment) | 43.9 |
| H296-H296 | 77.3 |
| H296-H296-H296-HT | 55.3 |
| CH296-CH296-HT | 71.7 |
| H105-H105-HT | 74.4 |

The CTLs in which the FN fragments were used during the induction of CTLs and the expansion showed high content ratios of positive cells, as compared to the control group without use. Here, the CTLs after the induction, in other words those cells before the expansion, had content ratios of TCR Vβ17-positive-CD8-positive cells of from 47.9% to 63.8% for the groups in which the FN fragments were used, and 67.8% for the control group without use. In other words, it was found that the expansion could be carried out while maintaining a high content ratio of the anti-influenza virus memory CTLs by using the FN fragments during the induction and the expansion of CTLs.

Example 29

Expansion of CTLs Obtained in Example 25 Without Using Feeder Cells Assuming 60 mL of Blood Collection (1) Immobilization of Anti-CD3 Antibody and Each of FN Fragments An anti-CD3 antibody and three kinds of the FN fragments were immobilized to a culture equipment used in the following experiment for the expansion of CTLs without using the feeder cells. Concretely, PBS containing the anti-CD3 antibody (final concentration: 5 µg/mL) and the FN fragments having a final concentration of 4 to 25 µg/mL was added to a 48-well cell culture plate (manufactured by Becton, Dickinson and Company) in a volume of 375 µL/well each, and the mixture was incubated overnight at 4° C. (the control being immobilized only with the anti-CD3 antibody). In addition, the above-mentioned plate was washed twice with PBS before use, and then washed once with the RPMI 1640 medium. Here, as to the concentration of the FN fragment, in order to match the amount immobilized to the culture equipment for each of the FN fragments to a given level, the concentration of the FN fragments used was adjusted.

(2) Expansion of CTLs Without Using Feeder Cells

The CTLs in an amount of $1\times10^5$ cells which were prepared in Example 25-(2) were suspended in 600 μL of 5HRPMI, and the suspension was put in the 48-well culture plate prepared in Example 29-(1), and the culture was initiated in a humidified $CO_2$ incubator at 37° C. Here, H105-H105-HT was added to the wells prepared in the same manner as that of the control, so as to have a final concentration of 0.4 μg/mL, and the culture was initiated. During the culture, in a culture scale using PBMCs in an amount of $5\times10^7$ cells assumed to be obtained from 60 mL of blood collection, the expansion was carried out by limiting the amount of human AB serum used from the induction to the expansion to a maximum of 30 mL, and the amount of the RPMI medium used to a maximum of 12 L. On the first day of the initiation of the culture, IL-2 was added thereto so as to have a final concentration of 500 U/mL, and on the fifth day and on, the cells were subcultured with a plate without the immobilization using a medium having a given serum concentration, prepared by properly diluting 5HRPMI with 0HRPMI (the RPMI 1640 medium containing 0% human AB serum, 1 mM sodium pyruvate, 2 mM L-glutamine, 10 mM HEPES, and 1% streptomycin-penicillin), and IL-2 having a final concentration of 500 U/mL was added thereto. In other words, subculture was carried out at a concentration of $1\times10^5$ cells/mL on the fifth day from the initiation of culture, a concentration of $1.5\times10^5$ cells/mL on the eighth day, and a concentration of $3\times10^5$ cells/mL on the twelfth day. Stimulation by a peptide was not added at all during this culture, and the expansion was carried out for 15 days. The cell proliferation rate is shown in Table 26.

TABLE 26

| FN Fragment | Cell Proliferation Rate (fold) | |
|---|---|---|
| | During the Expansion | from the Induction |
| Control (Without Immobilization with FN Fragment) | 3.2 | 2.5 |
| H296-H296 | 128.1 | 291.5 |
| H296-H296-H296-HT | 105.2 | 152.8 |
| CH296-CH296-HT | 72.1 | 166.1 |
| H105-H105-HT | 36.3 | 65.5 |

The groups in which the FN fragments were used during the induction and the expansion showed high proliferation rates as compared to the control group without use. In other words, it was shown that the expansion of the CTLs could be carried out without using the feeder cells, by using the FN fragments during the induction and the expansion, and the FN fragment that gave the highest effect was H296-H296.

Example 30

Assay of Cytotoxic Activity of CTLs of Example 29

The specific cytotoxic activity of CTLs for the CTLs obtained in Example 29-(2) was assayed in the same manner as in Example 27. The results for the cytotoxic activity after the expansion of CTLs are shown in Table 27, and the effects of activity maintenance are shown in Table 28. Here, as to the results for the cytotoxic activity, no test was conducted at an E/T ratio of 30, and as to the effects of maintaining the cytotoxic activity, the calculations were made on two points, E/T ratios of 3 and 1.

TABLE 27

| FN Fragment | Cytotoxic Activity (%) After Expansion of CTLs E/T Ratio | | |
|---|---|---|---|
| | 10 | 3 | 1 |
| Control (Without Immobilization with FN Fragment) | n.t. | n.t. | 10.6 |
| H296-H296 | 83.1 | 57.3 | 27.1 |
| H296-H296-H296-HT | 67.6 | 34.4 | 15.7 |
| CH296-CH296-HT | 60.7 | 32.8 | 14.1 |
| H105-H105-HT | 83.5 | 66.0 | 36.9 | n.t. = not tested.

TABLE 28

| FN Fragment | Effect of Activity Maintenance (%) E/T Ratio | |
|---|---|---|
| | 3 | 1 |
| Control (Without Immobilization with FN Fragment) | n.t. | 25.8 |
| H296-H296 | 73.0 | 75.3 |
| H296-H296-H296-HT | 42.7 | 39.5 |
| CH296-CH296-HT | 45.3 | 47.2 |
| H105-H105-HT | 91.9 | 118.3 | n.t. = not tested.

The cytotoxic activity against the Calcein-labeled target cells cultured in the absence of the peptide was almost 0%, confirming that the non-specific activity was not found therefor. Regarding the cytotoxic activity against the Calcein-labeled target cells cultured in the presence of the peptide, the CTLs of the groups in which the FN fragments were used during the induction and the expansion maintained specific, high cytotoxic activities even after the expansion for 15 days, as compared to the control group. In other words, it was clarified that the expansion could be carried out according to a method without using the feeder cells in a state that a specific, high cytotoxic activity was maintained for a long period of time, by using the FN fragments during the induction and the expansion of CTLs, and that the FN fragments having higher effects were H296-H296 and H105-H105-HT.

Example 31

Determination of Content Ratio of TCR Vβ17-Positive Cells in Cell Population of CTLs Obtained in Example 29

The content ratio of TCR Vβ17-positive-CD8-positive cells was determined for the CTLs in an amount of $2\times10^5$ cells prepared in Example 29-(2) in the same manner as in Example 28. The results are shown in Table 29.

TABLE 29

| FN Fragment | TCR Vβ17$^+$ CD8$^+$ (%) |
|---|---|
| Control (Without Immobilization with FN Fragment) | 19.9 |
| H296-H296 | 81.9 |
| H296-H296-H296-HT | 25.4 |
| CH296-CH296-HT | 22.9 |
| H105-H105-HT | 80.9 |

The groups in which the FN fragments were used during the induction and the expansion showed high content ratios of positive cells. Here, the CTLs after the induction, in other words those cells before the expansion, had content ratios of TCR Vβ17-positive-CD8-positive cells of from 47.9% to 63.8% for the groups in which the FN fragments were used, and 67.8% for the control group without use. In other words, it was found that the expansion could be carried out while maintaining a high content ratio of the anti-influenza virus memory CTLs in a system without using the feeder cells, by using the FN fragments during the induction and the expansion, and it was shown that H296-H296 and H105-H105-HT were especially effective.

Example 32

Expansion of Lymphocytes (Lymphokine-Activated Cells) Using Each of FN Fragments (1) Immobilization of Anti-Human CD3 Antibody and Three Kinds of FN Fragments An anti-human CD3 antibody and three kinds of the FN fragments, namely, H296-H296, H296-H296-H296-HT, and CH296-CH296-HT, were respectively immobilized to a culture equipment used in the following experiment. Concretely, PBS containing an anti-human CD3 antibody (final concentration: 5 μg/mL) and each of FN fragments having a final concentration of 2 to 4 μg/mL was added to the 12-well cell culture plate in a volume of 1.9 mL/well each. Here, as to the concentration of the FN fragment, the concentration of the FN fragments used was controlled in order to match the amount of each FN fragment immobilized to the culture equipment to a given level. After these culture equipments were incubated at room temperature for 5 hours, the culture equipments were stored at 4° C. until use. Immediately before use, PBS containing the antibody and the FN fragments was removed by aspiration from these culture equipments, and thereafter each well was washed twice with PBS, and once with the RPMI medium, and the culture equipments were subjected to each experiment.

(2) Expansion of Lymphocytes

PBMCs which were prepared in Example 21-(1) were suspended in GT-T503 (manufactured by TARAKA BIO INC.) containing 0.5% human AB serum and 0.2% human serum albumin (hereinafter simply referred to as "0.5% GT-T503"), so as to have a concentration of $0.25 \times 10^6$ cells/mL. Thereafter, the 0.5% GT-T503 was previously added to a plate immobilized with the anti-human CD3 antibody or a plate immobilized with the anti-human CD3 antibody and the FN fragments, prepared in Example 32-(1), in a volume of 0.5 mL/well, and the cell suspension was added thereto in a volume of 1 mL/well each. H105-H105-HT was directly added to the wells prepared in the same manner as the control so as to have a final concentration of 0.67 μg/mL. Subsequently, IL-2 was added thereto so as to have a final concentration of 1000 U/mL, and these plates were subjected to culture at 37° C. in 5% $CO_2$ (zeroth day of culture). On the fourth day from the initiation of culture, the culture medium of each group was diluted 8-folds with the 0.5% GT-T503, and 6 mL of the dilution was transferred to a 12.5 cm² cell culture flask to which nothing was immobilized, and IL-2 was added thereto so as to each have a final concentration of 500 U/mL. The culture was continued, and on the seventh day, the culture medium of each group was diluted 4.2-folds with the 0.5% GT-T503, and 12.6 mL of the dilution was transferred to a fresh 25 cm² cell culture flask (standing culture) to which nothing was immobilized, and IL-2 was added thereto so as to each have a final concentration of 500 U/mL. On the eleventh day from the initiation of the culture, the cell culture medium of each group was diluted 2-folds with serum-free GT-T503 containing 0.2% human serum albumin, and the dilution in a volume of 12.6 mL was each transferred to a fresh 25 cm² cell culture flask (standing culture) to which nothing was immobilized. To each group IL-2 was added so as to have a final concentration of 500 U/mL. On the fourteenth day from the initiation of culture, the number of viable cells was counted by trypan blue staining method, and an expansion fold was calculated by comparing the number of the counted cells with the number of cells at the initiation of culture. The results are shown in Table 30.

TABLE 30

| FN Fragment | Expansion Fold (fold) |
| --- | --- |
| Control (Without Immobilization with FN Fragment) | 172 |
| H296-H296 | 514 |
| H296-H296-H296-HT | 477 |
| CH296-CH296-HT | 437 |
| H105-H105-HT | 408 |

As shown in Table 30, the groups in which the culture equipments immobilized with the FN fragments at an early stage of the expansion of the lymphocytes were used, or the groups with direct addition of a solution to the culture medium gave high expansion folds as compared to the control group. In other words, it was clarified that the four kinds of the FN fragments are suitably used during the expansion of the lymphocytes.

Example 33

Analyses of CD45RA-Positive-CCR7-Positive Cells, CD27-Positive Cells, and CD28-Positive Cells The cells prepared in Example 32-(2) were washed with PBS, and with 1% BSA/PBS. The cells were suspended in PBS containing 1% BSA, FITC-labeled mouse IgG1/RD1-labeled mouse IgG1/PC5-labeled mouse IgG1 (manufactured by BECKMAN COULTER) and was added thereto as a negative control. In the same manner, cells with addition of RD1-labeled mouse anti-human CD45RA antibody (manufactured by BECKMAN COULTER)/FITC-labeled mouse anti-human CCR7 antibody (manufactured by R & D Systems), and cells with addition of RD1-labeled mouse anti-human CD27 antibody (manufactured by BECKMAN COULTER)/FITC-labeled mouse anti-human CD28 antibody (manufactured by eBioscience) were furnished. After each of the antibodies was added, the mixture was incubated on ice for 30 minutes. After the incubation, the cells were washed with PBS containing 0.1% BSA, and re-suspended in PBS. The cells obtained were subjected to flow cytometry, and for each of the cell population, a proportion of the CD45RA-positive-CCR7-positive cells, the CD27-positive cells, or the CD28-positive cells was calculated. The results are shown Table 31, Table 32, and Table 33.

TABLE 31

| FN Fragment | CD45RA$^+$ CCR7$^+$ (%) |
| --- | --- |
| Control (Without Immobilization with FN Fragment) | 21.2 |
| H296-H296 | 71.9 |
| H296-H296-H296-HT | 70.8 |
| CH296-CH296-HT | 68.3 |
| H105-H105-HT | 73.5 |

TABLE 32

| FN Fragment | CD27+ (%) |
|---|---|
| Control (Without Immobilization with FN Fragment) | 54.1 |
| H296-H296 | 88.5 |
| H296-H296-H296-HT | 90.0 |
| CH296-CH296-HT | 89.3 |
| H105-H105-HT | 87.8 |

TABLE 33

| FN Fragment | CD28+ (%) |
|---|---|
| Control (Without Immobilization with FN Fragment) | 80.1 |
| H296-H296 | 96.0 |
| H296-H296-H296-HT | 96.5 |
| CH296-CH296-HT | 96.4 |
| H105-H105-HT | 94.2 |

As shown in Table 31, Table 32, and Table 33, in the groups in which the culture equipments immobilized with the FN fragments at an early stage of the expansion of the lymphocytes were used, or the group with direct addition of a solution to the culture medium, the CD45RA+CCR7+ cell population, the CD27+ cell population, and the CD28+ cell population gave higher effects, as compared to the control group. All of these are phenotypes found in naive T cells, so that the effects when transfusing the lymphocytes after the expansion back to the body can be expected. According to this example, it was clarified that the naive T-like cells can be proliferated in a high efficiency by using the four kinds of the FN fragments.

Example 34

Studies on Immobilization Buffer for H-296

An H-296 solution prepared by adding 0.2 M phosphate buffer or 0.2 M acetate buffer at a pH of 3.8 to a pH of 8.0 with an increment of 0.6, so as to have concentrations of 25 and 50 μg/mL, was each added to each well of a 96-well cell culture plate to allow immobilization at room temperature for 5 hours. The wells were washed three times with PBS, Block Ace (manufactured by Dainippon Pharmaceutical) which was diluted 4-folds with PBS was then added to each well, and the mixture was allowed to stand at room temperature for 1 hour. The wells were then washed three times with PBS, and an FNH3-8 antibody (manufactured by TAKARA BIO INC.) labeled with HRP was added to each well, and the mixture was allowed to stand at room temperature for 1 hour, and then washed three times with PBS. This plate was subjected to color development using ABTS (manufactured by SIGMA), and an immobilization rate was evaluated by measuring the absorbance at 405 nm. Here, the FNH3-8 antibody is an antibody that specifically recognizes III-12, a partial region of the fibronectin (see FIG. 1). The results are shown in Table 34.

TABLE 34

| | | 405 nm | |
|---|---|---|---|
| pH | Buffer | 25 μg/mL | 50 μg/mL |
| 8.0 | Phosphate Buffer | 0.104 | 0.174 |
| 7.4 | Phosphate Buffer | 0.080 | 0.169 |
| 6.8 | Phosphate Buffer | 0.075 | 0.167 |
| 6.2 | Phosphate Buffer | 0.131 | 0.244 |
| 5.6 | Acetate Buffer | 0.475 | 0.567 |
| 5.0 | Acetate Buffer | 0.392 | 0.451 |
| 4.4 | Acetate Buffer | 0.428 | 0.379 |
| 3.8 | Acetate Buffer | 0.243 | 0.213 |

It was clarified from Table 34 that in the case where the acetate buffer having a pH lower than the phosphate buffer was used, H-296 had a higher immobilization efficiency to the culture plate, and the case of immobilization using acetate buffer having a pH of 5.6 showed a high immobilization rate.

Example 35

Comparison of Amounts of H-296 and H296-H296 Immobilized

An H-296 solution stepwise diluted with 0.2 M acetate buffer (pH 5.6) (hereinafter referred to as "pH 5.6 acetate buffer") and an H296-H296 solution stepwise diluted with PBS (pH 7.4) were each immobilized to a 96-well cell culture plate, and allowed to stand for 5 hours. The amount of the FN fragment immobilized on this plate was determined in the same manner as in Example 34. The results are shown in Table 35.

TABLE 35

| | 405 nm | |
|---|---|---|
| FNfr Concentration (μg/mL) | H-296 (pH 5.6 Acetate Buffer) | H296-H296 (PBS) |
| 200 | 0.964 | |
| 100 | 0.499 | |
| 50 | 0.304 | |
| 25 | 0.224 | 2.022 |
| 12.5 | 0.277 | 1.731 |
| 6.25 | 0.221 | 1.291 |
| 3.125 | | 1.010 |
| 1.563 | | 0.732 |

As a result, H296-H296 had a very high efficiency of immobilization to the culture plate, as compared to H-296, and it was shown that the amount of H-296 immobilized using a pH 5.6 acetate buffer of 200 μg/mL and the amount of H296-H296 immobilized using PBS of about 3 μg/mL were nearly congruent in a weight ratio.

Example 36

Induction of CTLs Having Specific Cytotoxic Activity Using H-296 or H296-H296 of Which Amount Immobilized to Culture Equipment Had Been Matched (1) Immobilization of Each of FN Fragments Each of two kinds of FN Fragments, H-296 and H296-H296, was immobilized to a culture equipment used in the following experiment. Concretely, a pH 5.6 acetate buffer or PBS, containing an FN fragment having a final concentration as shown in Table 36 was added to the 24-well cell culture plate in a volume of 1 mL/well each, and the mixture was incubated overnight at 4° C. The culture equipment was washed twice with PBS before use, and then washed once with the RPMI 1640 medium, and the culture equipments were subjected to each experiment.

TABLE 36

| FN Fragment | Immobilization Buffer | Final Concentration |
| --- | --- | --- |
| H-296 | pH 5.6 Acetate Buffer | 200 μg/mL |
| H296-H296 | PBS | 3 μg/mL |

Here, from Example 35 described above, the amount immobilized to the culture plate using the above-mentioned H-296 having a final concentration of 200 μg/mL H-296 is equivalent to that using H296-H296 having a final concentration of 3 μg/mL.

(2) Induction of Anti-Influenza Virus Memory CTLs

Using the PBMCs isolated and stored according to the method described in Example 2-(1), the induction of the anti-influenza virus memory CTLs was carried out in the same manner as in Example 2-(3). During the induction, the plate used was the one prepared in Example 36-(1) (as the control, a plate without immobilization of the FN fragment being used). The cell proliferation rate after 14 days of the culture is shown in Table 37.

TABLE 37

| FN Fragment | Cell Proliferation Rate (fold) |
| --- | --- |
| Control (Without Immobilization with FN Fragment) | 1.2 |
| H-296 (200 μg/mL) | 1.5 |
| H296-H296 (3 μg/mL immobilized) | 2.1 |

The cell proliferation rate was defined by a ratio of the number of cells at the point of time of the termination of the induction to the number of responder cells at the initiation of the induction of CTLs as a proliferation rate. As a result, the groups in which the FN fragments were used showed high proliferation rates as compared to the control group without use. In other words, it was clarified that the proliferation rates of the cells were enhanced by using the FN fragments during the induction of CTLs. In addition, even while the amount immobilized to the plate was in an equivalent level for H-296 (200 μg/mL) and H296-H296 (3 μg/mL), the cell proliferation rate for H296-H296 (3 μg/mL) was higher.

Example 37

Expansion of CTLs of Example 36 Without Using Feeder Cells Assuming 30 mL of Blood Collection (1) Immobilization of Anti-CD3 Antibody and Each of FN Fragments An anti-CD3 antibody and two kinds of the FN fragments were immobilized to a culture equipment used in the following experiment for the expansion of CTLs without using the feeder cells. Concretely, a pH 5.6 acetate buffer or PBS, each containing the anti-CD3 antibody (final concentration: 5 μg/mL) and the FN fragments having a concentration as shown in Table 36 was added to a 96-well cell culture plate in a volume of 160 μL/well each, and the mixture was incubated overnight at 4° C. (the control being immobilized only with the anti-CD3 antibody). In addition, the above-mentioned plate was washed twice with PBS before use, and then washed once with the RPMI 1640.

(2) Expansion of CTLs Without Using Feeder Cells

The CTLs prepared in Example 36-(2) in an amount of $1 \times 10^5$ cells were subjected to expansion in the same manner as in Example 15-(2). During the expansion, the 96-well culture plate prepared in Example 37-(1) was used, and the culture was initiated using 5HRPMI. On the first day of the initiation of the culture, IL-2 was added thereto so as to have a final concentration of 500 U/mL, and on the fifth day and on, the cells were subcultured with a plate to which nothing was immobilized, using a medium having a given serum concentration, prepared by properly diluting 5HRPMI with 0HRPMI, and IL-2 having a final concentration of 500 U/mL was added thereto. In other words, subculture was carried out at a concentration of $0.75 \times 10^5$ cells/mL on the fifth day from the initiation of culture, a concentration of $1.5 \times 10^5$ cells/mL on the eighth day, and a concentration of $3 \times 10^5$ cells/mL on the twelfth day. Stimulation by a peptide was not added at all during this culture, and the expansion was carried out for 15 days. The cell proliferation rate is shown in Table 38.

TABLE 38

| | Cell Proliferation Rate (fold) | |
| --- | --- | --- |
| FN Fragment | During the Expansion | from the Induction |
| Control (Without Immobilization with FN Fragment) | 3.8 | 4.7 |
| H-296 (200 μg/mL) | 27.6 | 41.9 |
| H296-H296 (3 μg/mL) | 73.2 | 150.4 |

The groups in which the FN fragments were used during the induction and the expansion showed high proliferation rates as compared to the control group without use. In other words, the expansion of the CTLs could be carried out without using the feeder cells, by using the FN fragments during the induction and the expansion. In addition, even while the amount immobilized to the plate was at an equivalent level for H-296 (200 μg/mL) and H296-H296 (3 μg/mL), the cell proliferation rate for H296-H296 (3 μg/mL) was even marked higher.

Example 38

Assay of Cytotoxic Activity of CTLs of Example 37

The specific cytotoxic activity of CTLs for the CTLs obtained in Example 37-(2) was assayed in the same manner as in Example 27. The results for the cytotoxic activity after the expansion of CTLs are shown in Table 39, and the effects of activity maintenance are shown in Table 40. Here, as to the results for the cytotoxic activity, no test was conducted at an E/T ratio of 30, and as to the effects of maintaining the cytotoxic activity, the calculations were made on two points, E/T ratios of 3 and 1.

TABLE 39

| | Cytotoxic Activity (%) After Expansion of CTLs E/T Ratio | | |
| --- | --- | --- | --- |
| FN Fragment | 10 | 3 | 1 |
| Control (Without Immobilization with FN Fragment) | n.t. | n.t. | 2.9 |
| H-296 | 18.5 | 7.8 | 6.0 |
| H296-H296 (3 μg/mL) | 55.7 | 24.0 | 9.9 |

TABLE 39-continued

|  | Cytotoxic Activity (%) After Expansion of CTLs E/T Ratio | | |
|---|---|---|---|
| FN Fragment | 10 | 3 | 1 | n.t. = not tested.

TABLE 40

|  | Effect of Activity Maintenance (%) E/T Ratio | |
|---|---|---|
| FN Fragment | 3 | 1 |
| Control (Without Immobilization with FN Fragment) | n.t. | 9.6 |
| H-296 | 12.5 | 20.1 |
| H296-H296 (3 μg/mL) | 41.2 | 34.4 | n.t. = not tested.

The cytotoxic activity against the Calcein-labeled target cells cultured in the absence of the peptide was almost 0%, confirming that the non-specific activity was not found therefor. Regarding the cytotoxic activity against the Calcein-labeled target cells cultured in the presence of the peptide, the CTLs of the groups in which the FN fragments were used during the induction and the expansion maintained specific, high cytotoxic activities even after the expansion for 15 days, as compared to the control group. In other words, it was clarified that the expansion could be carried out according to a method without using the feeder cells in a state that a specific, high cytotoxic activity was maintained for a long period of time, by using the FN fragments during the induction and the expansion of CTLs, and that the FN fragment that gave a higher effect was H296-H296.

Example 39

Generation of H296-H296-HT (1) Construction of H296-H296-HT Expression Vector

In order to allow expression of a modified fibronectin fragment (H296-H296-HT) in which two H-296's were connected, an expression vector was constructed in the manner described below.

(i) Construction of pT7-H296 Vector

From the nucleotide sequence of CH-296 (SEQ ID NO: 8 of Sequence Listing), a synthetic primer CS1-NdeR having the nucleotide sequence shown in SEQ ID NO: 24 of Sequence Listing was synthesized with a DNA synthesizer, and purified according to a conventional method. The synthetic primer CS1-NdeR is a synthetic DNA having a recognized sequence with a restriction enzyme NdeI in the base numbers 4-9, and further having a nucleotide sequence corresponding to amino acid numbers 574-569 of the amino acid sequence of CH-296 (SEQ ID NO: 7 of Sequence Listing) in the base numbers 10-27.

PCR was carried out using the above-mentioned synthetic primers. The reaction conditions for PCR are given hereinafter. Concretely, about 0.1 μg of the pColdI-H296 constructed in Example 22-(1)-(i) as a template DNA, 10 μL of the 10× Ex Taq Buffer, 8 μL of the dNTP mixture, 20 pmol of a synthetic primer H296-NdeF, 20 pmol of a synthetic primer CS1-NdeR, and 1 U TaKaRa Ex Taq were added together, and a sterile water was added thereto to make up a total volume of 100 μL. The above reaction mixture was set in the TaKaRa PCR Thermal Cycler SP, and 30 cycles of reaction, each cycle comprising 94° C. for 1 minute, 55° C. for 1 minute, and 72° C. for 3 minutes, were performed. After the termination of the reaction, 5 μL of the reaction mixture was electrophoresed with 1.0% agarose gel, and a desired DNA fragment having a size of about 0.9 kbp was confirmed. The remainder of the reaction mixture for PCR was electrophoresed, and a fragment thereof was collected and purified.

Next, pT7Blue T-vector (manufactured by Novagen (Merck), TAKARA BIO INC.) was mixed with the above-mentioned DNA fragment, and ligated with the DNA ligation kit. Thereafter, *Escherichia coli* JM109 was transformed with 10 μL of the ligation reaction mixture, and the resulting transformant was grown on an LB medium (containing 50 μg/mL ampicillin) containing agar in a concentration of 1.5% (w/v). A recombinant plasmid inserted with the desired DNA fragment was referred to as pT7-H296.

(ii) Construction of H296-H296-HT Expression Vector pT7-H296 was digested with NdeI, to give a DNA fragment having a size of about 0.9 kbp, and the fragment was electrophoresed with 1.0% agarose gel, thereby collecting and purifying the fragment. Next, the pColdI-H296 constructed in Example 22-(1)-(i) was digested with NdeI, and the terminals of the digest were subjected to a dephosphorization treatment to prepare a product, and the product was mixed with the above-mentioned DNA fragment having a size of about 0.9 kbp, and ligated using the DNA ligation kit. Thereafter, *Escherichia coli* JM109 was transformed with 10 μL of the ligation reaction mixture, and the resulting transformant was grown on an LB medium (containing 50 μg/mL ampicillin) containing agar in a concentration of 1.5% (w/v).

The desired plasmid inserted with a DNA fragment encoding a protein in which two H-296's were connected was confirmed by sequencing, and this recombinant plasmid was referred to as pColdI-H296-2. This pColdI-H296-2 is a plasmid containing a DNA sequence encoding a polypeptide in which two nucleotide sequences encoding the amino acid sequence of the amino acid numbers 278-574 of CH-296 are connected with an amino acid "H" inserted therebetween, the polypeptide having a His tag sequence at an N-terminal thereof. The protein is named H296-H296-HT, and an amino acid sequence thereof is shown in SEQ ID NO: 25 of Sequence Listing, and a nucleotide sequence thereof is shown in SEQ ID NO: 26 of Sequence Listing.

(2) Expression and Purification of H296-H296-HT

*Escherichia coli* BL21 was transformed with the pColdI-H296-2 prepared in Example 39-(1)-(ii), and the expression and purification of H296-H296-HT were carried out in the same manner as in Example 22-(2). Here, the amounts of liquid volume of the culture medium, Binding Buffer, Washing Buffer A, Washing Buffer B, Elution Buffer, and the concentrate were properly changed as occasion demands. The concentrate obtained was analyzed with 2100 Bioanalyzer (manufactured by Agilent Technologies), and as a result, a target protein having a molecular weight of about 67 kDa was detected in a nearly single band, and the concentration of the protein was 1.3 mg/mL (about 19 μM, calculated from the molecular weight).

Example 40

Generation of H296-H296-H296

(1) Expression and Purification of H296-H296-H296-HT

*Escherichia coli* BL21 was transformed with the pColdI-H296-3 prepared in Example 22-(1)-(ii), and the expression and purification of H296-H296-H296-HT were carried out in the same manner as in Example 22-(2). Here, the amounts of liquid volume of the culture medium, Binding Buffer, Washing Buffer A, Washing Buffer B, Elution Buffer, and the concentrate were properly changed as occasion demands. The concentrate obtained was analyzed with the 2100 Bioanalyzer, and as a result, a target protein having a molecular weight of about 99 kDa was detected in nearly a single band, and the concentration of the protein was 3.7 mg/mL (about 37 µM, calculated from the molecular weight).

(2) Purification of H296-H296-H296

Next, a His-tag sequence of a 3 mg portion of the H296-H296-H296-HT purified protein purified in Example 40-(1) was cleaved with Factor Xa Cleavage Capture Kit (manufactured by Merck) overnight at 4° C., and thereafter the target protein without a His tag was purified. The cleavage of the His tag and the purification of the target protein were performed in accordance with the instruction manual attached to the above-mentioned Kit. The solution after the cleavage was analyzed with the 2100 Bioanalyzer, and as a result, a target protein having a molecular weight of about 97 kDa was detected in a nearly single band, and the concentration of the protein was 0.65 mg/mL (about 6.7 µM, calculated from the molecular weight). The amino acid sequence of H296-H296-H296 is shown in SEQ ID NO: 27 of Sequence Listing, and a nucleotide sequence which is deduced to encode the protein is shown in SEQ ID NO: 28 of Sequence Listing.

Example 41

Generation of H105-H105

(1) Expression and Purification of H105-H105-HT

The expression and purification of H105-H105-HT were carried out in the same manner as in Example 24-(2). The concentrate obtained was analyzed with the 2100 Bioanalyzer, and as a result, a target protein having a molecular weight of about 28 kDa was detected in a nearly single band, and the concentration of the protein was 1.25 mg/mL (about 45 µM, calculated from the molecular weight).

(2) Purification of H105-H105

A His-tag sequence of a 3 mg portion of the above-mentioned H105-H105-HT purified protein was cleaved with the Factor Xa Cleavage Capture Kit overnight at 4° C. in the same manner as Example 40-(2), and thereafter the target protein without a His tag was purified. The cleavage of the His tag and the purification of the target protein were performed in accordance with the instruction manual attached to the above-mentioned Kit. The solution after the cleavage was analyzed with the 2100 Bioanalyzer, and as a result, a target protein having a molecular weight of about 26 kDa was detected in a nearly single band, and the concentration of the protein was 0.42 mg/mL (about 16 µM, calculated from the molecular weight). The amino acid sequence of H105-H105 is shown in SEQ ID NO: 29 of Sequence Listing, and a nucleotide sequence which is deduced to encode the protein is shown in SEQ ID NO: 30 of Sequence Listing.

Example 42

Expansion of Lymphocytes (Lymphokine-Activated Cells) Using Anti-CD3 Antibody, Anti-CD28 Antibody and FN Fragment (H296-H296-HT, H296-H296-H296-HT, H105-H105-HT, H296-H296, H296-H296-H296, or H105-H105)

(1) Immobilization of Anti-Human CD3 Antibody, Anti-Human CD28 Antibody and Six Kinds of FN Fragments An anti-human CD3 antibody, an anti-human CD28 antibody and six kinds of the FN fragment, namely, H296-H296-HT, H296-H296-H296-HT, H105-H105-HT, H296-H296, H296-H296-H296, or H105-H105, were immobilized to a culture equipment used in the following experiment. Concretely, an ACD-A solution (pH 5.0) containing an anti-human CD3 antibody (final concentration: 5 µg/mL), an anti-human CD28 antibody (manufactured by Dako Japan, final concentration: 5 µg/mL) and each of FN fragments having a final concentration of 1 to 25 µg/mL was added to a 12-well cell culture plate (manufactured by Corning) in a volume of 0.45 mL/well each. Here, the concentration of the FN fragment used was controlled in order to match the amount of each FN fragment immobilized to the culture equipment to a given level. Upon the immobilization, as the FN fragments, H296-H296-HT prepared in Example 39, H296-H296-H296-HT prepared in Example 22, H105-H105-HT prepared in Example 24, H296-H296 prepared in Example 1, H296-H296-H296 prepared in Example 40, and H105-H105 prepared in Example 41 were used. These culture equipments were incubated at room temperature for 5 hours Immediately before use, an ACD-A solution (pH 5.0) containing the antibodies and the FN fragment was removed by aspiration from these culture equipments, and thereafter each well was washed twice with PBS, and once with the RPMI medium, and the culture equipments were subjected to each experiment.

(2) Expansion of Lymphocytes

PBMCs which were prepared in Example 2-(1) were suspended in 0.5% GT-T503, so as to have a concentration of $0.5 \times 10^6$ cells/mL Thereafter, the 0.5% GT-T503 was previously added to a plate immobilized with the anti-human CD3 antibody and the anti-human CD28 antibody or a plate immobilized with the anti-human CD3 antibody, the anti-human CD28 antibody and the FN fragment, prepared in Example 42-(1), in a volume of 1.0 mL/well, and the cell suspension was added thereto in a volume of 0.5 mL/well each. Subsequently, IL-2 was added thereto so as to have a final concentration of 1000 U/mL, and these plates were subjected to culture at 37° C. in 5% $CO_2$ (zeroth day of culture). On the fourth day from the initiation of culture, the culture medium of each group was diluted 14.3-folds with the 0.5% GT-T503, and 10 mL of the dilution was transferred to the 25 cm² cell culture flask (standing culture) to which nothing was immobilized, and IL-2 was added thereto so as to each have a final concentration of 500 U/mL The culture was continued, and on the eighth day, the culture medium of each group was diluted 2-folds with the 0.5% GT-T503, and 10 mL of the dilution was transferred to a fresh 25 cm² cell culture flask (standing culture) to which nothing was immobilized, and IL-2 was added thereto so as to each have a final concentration of 500 U/mL On the eleventh day from the initiation of the culture, the number of viable cells was counted by trypan blue staining method, and an expansion fold was calculated by comparing the number of the counted cells with the number of cells at the initiation of culture. The results are shown in Table 41.

TABLE 41

| FN Fragment | Expansion Fold (fold) |
|---|---|
| Control (Without Immobilization with FN Fragment) | 367 |
| H296-H296-HT | 402 |
| H296-H296 | 434 |
| H296-H296-H296-HT | 463 |
| H296-H296-H296 | 392 |
| H105-H105-HT | 490 |
| H105-H105 | 496 |

As shown in Table 41, the groups in which the culture equipments immobilized with the FN fragment at an early stage of the expansion of the lymphocytes were used gave high expansion folds as compared to the control group. In other words, it was clarified that the six kinds of the FN fragments are suitably used even during the expansion of the lymphocytes in which the six kinds of the FN fragments are used in combination with stimulation with the anti-CD3 antibody and the anti-CD28 antibody.

Example 43

Analyses of CD45RA-Positive-CCR7-Positive Cells, CD45RA-Positive-CD62L-Positive Cells, and CD45RA-Positive-CCR7-Positive-CD62L-Positive Cells of Lymphocytes (Lymphokine-Activated Cells) Cultured Using Each of FN Fragments (H296-H296-HT and H296-H296)

(1) Immobilization of Anti-Human CD3 Antibody and Two Kinds of FN Fragments

An anti-human CD3 antibody and two kinds of the FN fragments, namely, H296-H296-HT and H296-H296, were immobilized to a culture equipment in the same manner as in Example 42-(1) used in the following experiment. During the immobilization, the anti-human CD28 antibody was not added, and the FN fragment were added to an ACD-A solution (pH 5.0) so as to have a final concentration of from 1 to 3 µg/mL Here, the concentration of the FN fragment used was controlled in order to match the amount of each FN fragment immobilized to the culture equipment to a given level. Here, as the FN fragments, H296-H296-HT prepared in Example 39 and H296-H296 prepared in Example 1 were used.

(2) Expansion of Lymphocytes

The expansion of the lymphocytes was carried out in the same manner as in Example 42-(2), using, on the zeroth day from the initiation of culture, the plate immobilized with anti-human CD3 antibody or the plate immobilized with the anti-human CD3 antibody and the FN fragment, prepared in Example 43-(1), except that on the eleventh day from the initiation of culture, the cell culture medium of each group was diluted 2-folds with the serum-free GT-T503 containing 0.2% human serum albumin, and IL-2 was then added so as to have a final concentration of 500 U/mL On the fourteenth day from the initiation of the culture, the number of viable cells was counted by trypan blue staining method, and an expansion fold was calculated by comparing the number of the counted cells with the number of cells at the initiation of culture. The results are shown in Table 42.

TABLE 42

| FN Fragment | Expansion Fold (fold) |
| --- | --- |
| Control (Without Immobilization with FN Fragment) | 129 |
| H296-H296-HT | 342 |
| H296-H296 | 201 |

As shown in Table 42, the groups in which the culture equipments immobilized with the FN fragments, namely, H296-H296-HT and H296-H296, at an early stage of the expansion of the lymphocytes were used gave high expansion folds as compared to the control group.

(3) Analyses of CD45RA-Positive-CCR7-Positive Cells, CD45RA-Positive-CD62L-Positive Cells, and CD45RA-Positive-CCR7-Positive-CD62L-Positive Cells The cells prepared in Example 43-(2) were analyzed for CD45RA-positive-CCR7-positive cells, CD45RA-positive-CD62L-positive cells, CD45RA-positive-CCR7-positive-CD62L-positive cells in the same manner as in Example 33, except that during the analysis RD1-labeled mouse anti-human CD45RA antibody/FITC-labeled mouse anti-human CCR7 antibody/PC5-labeled mouse anti-human CD62L antibody (all of which being manufactured by BECKMAN COULTER) was added. The cells obtained were subjected to flow cytometry, and a proportion of the CD45RA-positive-CCR7-positive cells, the CD45RA-positive-CD62L-positive cells, and the CD45RA-positive-CCR7-positive-CD62L-positive cells was calculated for each of the cell population. The results are shown in Table 43.

TABLE 43

| FN Fragment | $CD45RA^+$ $CCR7^+$ (%) | $CD45RA^+$ $CD62L^+$ (%) | $CD45RA^+$ $CCR7^+$ $CD62L^+$ (%) |
| --- | --- | --- | --- |
| Control (Without Immobilization with FN Fragment) | 27.8 | 53.9 | 24.2 |
| H296-H296-HT | 58.5 | 80.1 | 56.9 |
| H296-H296 | 57.8 | 80.9 | 57.1 |

As shown in Table 43, the groups in which the culture equipments immobilized with the FN fragments, namely H296-H296-HT and H296-H296, at an early stage of the expansion of the lymphocytes were used gave higher effects in the proportions of the CD45RA-positive-CCR7-positive cell population, the CD45RA-positive-CD62L-positive cell population, and the CD45RA-positive-CCR7-positive-CD62L-positive cell population, as compared to those of the control group. According to the example, it was clarified that the naive T-like cells can be proliferated in a high efficiency by using the two kinds of the FN fragments, namely H296-H296-HT and H296-H296.

Example 44

Expansion of Lymphocytes (Lymphokine-Activated Cells) Using Anti-CD3 Antibody and FN Fragment (H296-H296-HT, H296-H296, H296-H296-H296-HT, or H296-H296-H296)

(1) Immobilization of Anti-Human CD3 Antibody and Four Kinds of FN Fragments

An anti-human CD3 antibody and four kinds of the FN fragment, namely, H296-H296-HT, H296-H296, H296-H296-H296-HT, or H296-H296-H296, were immobilized in the same manner as in Example 43-(1) to a culture equipment used in the following experiment, except that as the buffer used upon the immobilization, the ACD-A solution (pH 5.0) was used, and that the FN fragment was added so as to have a final concentration of 1 to 25 µg/mL Here, the concentration of the FN fragment used was controlled in order to match the amount of each FN fragment immobilized to the culture equipment to a given level. Upon the immobilization, as the FN fragments, H296-H296-HT prepared in Example 39, H296-H296 prepared in Example 1, H296-H296-H296-HT prepared in Example 22, and H296-H296-H296 prepared in Example 40 were used.

(2) Expansion of Lymphocytes

The expansion of the lymphocytes was carried out in the same manner as in Example 43-(2), except that on the zeroth day from the initiation of culture, the plate immobilized with anti-human CD3 antibody or the plate immobilized with the anti-human CD3 antibody and the FN fragment, prepared in Example 44-(1) was used, and that groups with direct addition of the fragment to the wells prepared in the same manner as the control were also set for H296-H296-HT and H296-H296, so as to have a final concentration of 0.67 μg/mL On the fourteenth day from the initiation of the culture, the number of viable cells was counted by trypan blue staining method, and an expansion fold was calculated by comparing the number of the counted cells with the number of cells at the initiation of culture. The results are shown in Table 44.

TABLE 44

| FN Fragment | Immobilization or Direct Addition | Expansion Fold (fold) |
| --- | --- | --- |
| Control (Without Immobilization or Without Addition of FN Fragment) | | 395 |
| H296-H296-HT | Immobilization | 603 |
| H296-H296 | Immobilization | 641 |
| H296-H296-H296-HT | Immobilization | 528 |
| H296-H296-H296 | Immobilization | 420 |
| H296-H296-HT | Direct Addition | 545 |
| H296-H296 | Direct Addition | 441 |

As shown in Table 44, the groups in which the culture equipments immobilized with the FN fragments, namely, H296-H296-HT, H296-H296, H296-H296-H296-HT, and H296-H296-H296, at an early stage of the expansion of the lymphocytes were used gave high expansion folds as compared to the control group. In addition, the groups with direct addition of the FN fragments, namely H296-H296-HT and H296-H296, to the medium gave high expansion folds, as compared to the control group. In other words, it was clarified that the four kinds of the FN fragments, namely H296-H296-HT, H296-H296, H296-H296-H296-HT, and H296-H296-H296, are suitably used during the expansion of the lymphocytes.

(3) Analyses of CD45RA-Positive-CCR7-Positive Cells, CD45RA-Positive-CD62L-Positive Cells, and CD45RA-Positive-CCR7-Positive-CD62L-Positive Cells The cells prepared in Example 44-(2) were analyzed for CD45RA-positive-CCR7-positive cells, CD45RA-positive-CD62L-positive cells, and CD45RA-positive-CCR7-positive-CD62L-positive cells in the same manner as in Example 43-(3). The results are shown in Table 45.

TABLE 45

| FN Fragment | Immobilization or Direct Addition | CD45RA$^+$ CCR7$^+$ (%) | CD45RA$^+$ CD62L$^+$ (%) | CD45RA$^+$ CCR7$^+$ CD62L$^+$ (%) |
| --- | --- | --- | --- | --- |
| Control (Without Immobilization or Without Addition of FN Fragment) | | 29.1 | 63.8 | 27.2 |
| H296-H296-HT | Immobilization | 76.2 | 92.5 | 75.4 |
| H296-H296 | Immobilization | 81.2 | 95.9 | 80.9 |
| H296-H296-H296-HT | Immobilization | 76.8 | 95.4 | 76.5 |
| H296-H296-H296 | Immobilization | 79.1 | 95.5 | 79.0 |
| H296-H296-HT | Direct Addition | 61.9 | 93.6 | 61.1 |
| H296-H296 | Direct Addition | 62.2 | 92.6 | 61.4 |

As shown in Table 45, the groups in which the culture equipments immobilized with the FN fragments, namely H296-H296-HT, H296-H296, H296-H296-H296-HT, and H296-H296-H296, at an early stage of the expansion of the lymphocytes were used gave higher effects in the proportions of the CD45RA-positive-CCR7-positive cell population, the CD45RA-positive-CD62L-positive cell population, and the CD45RA-positive-CCR7-positive-CD62L-positive cell population, as compared to those of the control group. In addition, the groups with direct addition of the FN fragments, namely H296-H296-HT and H296-H296, to the medium similarly gave results in high proportions. According to the example, it was clarified that the naive T-like cells can be proliferated in a high efficiency by using the four kinds of the FN fragments, namely H296-H296-HT, H296-H296, H296-H296-H296-HT, and H296-H296-H296.

Example 45

Generation of H271-H296

(1) Construction of H271-H296 Expression Vector

In order to allow expression of a modified fibronectin fragment (H271-H296) in which H-271 and H-296 were connected, an expression vector was constructed in the manner described below.

(i) Construction of pCold14-H271-H296 Vector

From the nucleotide sequence of CH-296 (SEQ ID NO: 8 of Sequence Listing), a synthetic primer H271-NcoR having the nucleotide sequence shown in SEQ ID NO: 31 of Sequence Listing was synthesized with a DNA synthesizer, and purified according to a conventional method. The above-mentioned synthetic primer H271-NcoR is a synthetic DNA having a recognized sequence with a restriction enzyme NcoI in the base numbers 10-15, and further having a nucleotide sequence corresponding to amino acid numbers 549-544 of the amino acid sequence of CH-296 (SEQ ID NO: 7) in the base numbers 17-34. PCR was carried out using the above-mentioned synthetic primer and a synthetic primer NC2-5'UTR shown in SEQ ID NO: 12 of Sequence Listing. The reaction conditions for PCR are given hereinafter.

Concretely, about 0.1 μg of pCold14-H296 constructed in Example 1-(1)-(i) as a template DNA, 10 μL of the 10× Pyrobest Buffer II, 8 μL of the dNTP mixture, 20 pmol of a synthetic primer NC2-5'UTR, 20 pmol of a synthetic primer H271-NcoR, and 5 U Pyrobest DNA Polymerase were added together, and a sterile water was added thereto to make up a total volume of 100 μL. The above reaction mixture was set in the TaKaRa PCR Thermal Cycler SP, and 30 cycles of reaction, each cycle comprising 96° C. for 1 minute and 68° C. for 4 minutes, were performed.

After the termination of the reaction, 5 μL of the reaction mixture was electrophoresed with 1.0% agarose gel, and a desired DNA fragment having a size of about 0.9 kbp was confirmed. The remainder of the reaction mixture for PCR was collected and purified, and the purified mixture was subjected to ethanol precipitation. The DNA collected after the ethanol precipitation was suspended in a sterile water, to make up a total volume of the reaction mixture of 50 μL, the reaction mixture was digested with the restriction enzyme NcoI, and the digest was electrophoresed with 1.0% agarose gel, thereby extracting and purifying an NcoI, NcoI digest, to give an NcoI-NcoI-digested DNA fragment having a size of about 0.8 kbp.

Next, the pCold14-H296 was digested with NcoI, and the terminals of the digest were subjected to a dephosphorization treatment to prepare a product, and the product was mixed with the above-mentioned DNA fragment having a size of about 0.8 kbp, and ligated with the DNA ligation kit. Thereafter, Escherichia coli JM109 was transformed with 10 μL of the ligation reaction mixture, and the resulting transformant was grown on an LB medium (containing 50 μg/mL ampicillin) containing agar in a concentration of 1.5% (w/v).

The plasmid inserted with the desired DNA fragment encoding a protein in which H-271 and H-296 were connected was confirmed by sequencing, and this recombinant plasmid was referred to as pCold14-H271-H296. This pCold14-H271-H296 is a plasmid containing a nucleotide sequence encoding the amino acid sequence of the amino acid numbers 278-549 of CH-296 and a nucleotide sequence encoding the amino acid sequence of the amino acid numbers 278-574 of CH-296, connected with an amino acid "A" inserted therebetween. The protein was named H271-H296, and an amino acid sequence thereof is shown in SEQ ID NO: 32 of Sequence Listing, and the nucleotide sequence is shown in SEQ ID NO: 33 of Sequence Listing.

(2) Expression and Purification of H271-H296

*Escherichia coli* BL21 was transformed with pCold14-H271-H296 prepared in the above-mentioned (1), and the expression and purification of H271-H296 were carried out in the same manner as in Example 1-(2). Here, the amounts of liquid volume of the culture medium, the cell disruption solution, the resin volume, buffer A, buffer B, buffer D, the fractionated solution, and the concentrate were properly changed as occasion demands. The concentrate obtained was analyzed by 10% SDS-PAGE, and as a result, a target protein having a molecular weight of about 62 kDa was detected in a nearly single band, and this was referred to as H271-H296. Thereafter, the concentration of the protein was determined with the MicroBCA kit, and as a result, the concentration was 1.6 mg/mL (about 25.8 μM, calculated from the molecular weight). Incidentally, it is deduced that the N-terminal is methionine-digested, and becomes Ala.

Example 46

Generation of H296-H271

(1) Construction of H296-H271 Expression Vector

In order to allow expression of a modified fibronectin fragment (H296-H271) in which H-296 and H-271 were connected, an expression vector was constructed in the manner described below.

(i) Construction of pCold14-H271 Vector

From the nucleotide sequence of CH-296 (SEQ ID NO: 8 of Sequence Listing), synthetic primers 12-Nco-F2 and H271-BamR having the nucleotide sequences shown in SEQ ID NOs: 34 and 35 of Sequence Listing were synthesized with a DNA synthesizer, and purified according to a conventional method. The above-mentioned synthetic primer 12-Nco-F2 is a synthetic DNA having a recognized sequence with a restriction enzyme NcoI in the base numbers 7-12, and further having a nucleotide sequence corresponding to amino acid numbers 279-285 of the amino acid sequence of CH-296 in the base numbers 12-32. The synthetic primer H271-BamR is a synthetic DNA having a recognized sequence with a restriction enzyme BamHI in the base numbers 8-13, and further having a nucleotide sequence corresponding to amino acid numbers 549-544 of the amino acid sequence of CH-296 (SEQ ID NO: 7 of Sequence Listing) in the base numbers 19-36.

PCR was carried out using the above-mentioned synthetic primers. The reaction conditions for PCR are given hereinafter. Concretely, about 0.1 μg of the pCold14-H296 as a template DNA, 10 μt of the 10× Pyrobest Buffer II, 8 μL of the dNTP mixture, 20 pmol of a synthetic primer 12-Nco-F2, 20 pmol of a synthetic primer H271-BamR, and 2.5 U Pyrobest DNA Polymerase were added together, and a sterile water was added thereto to make up a total volume of 100 μt. The above reaction mixture was set in the TaKaRa PCR Thermal Cycler SP, and 30 cycles of reaction, each cycle comprising 98° C. for 10 seconds and 68° C. for 1 minute, were performed. After the termination of the reaction, 5 μL of the reaction mixture was electrophoresed with 1.0% agarose gel, and a desired DNA fragment having a size of about 0.8 kbp was confirmed. The remainder of the reaction mixture for PCR was subjected to ethanol precipitation, and the DNA collected was suspended in a sterile water, and subjected to a double digestion with the restriction enzyme NcoI and a restriction enzyme BamHI (manufactured by TAKARA BIO, INC.). The digest was electrophoresed with 1.0% agarose gel, thereby extracting and purifying the NcoI, BamHI digest, to give an NcoI-BamHI-digested DNA fragment.

Next, the pCold14 vector digested with NcoI and BamHI was prepared, and the digest was mixed with the above-mentioned NcoI-BamHI-digested DNA fragment, and ligated with the DNA ligation kit. Thereafter, *Escherichia coli* JM109 was transformed with 10 μL of the ligation reaction mixture, and the resulting transformant was grown on an LB medium (containing 50 μg/mL ampicillin) containing agar in a concentration of 1.5% (w/v). A recombinant plasmid inserted with the desired DNA fragment was referred to as pCold14-H271.

(ii) Construction of H296-H271 Expression Vector

Next, PCR was carried out using a synthetic primer H296-NcoR having the nucleotide sequence as shown in SEQ ID NO: 11 of Sequence Listing and a synthetic primer NC2-5'UTR as shown in SEQ ID NO: 12 of Sequence Listing. The reaction conditions for PCR are given hereinafter.

Concretely, about 0.1 μg of pCold14-H296 constructed in Example 1-(1)-(i) as a template DNA, 10 μL of the 10× Pyrobest Buffer II, 8 μL of the dNTP mixture, 20 pmol of a synthetic primer NC2-5'UTR, 20 pmol of a synthetic primer H296-NcoR, and 5 U Pyrobest DNA Polymerase were added together, and a sterile water was added thereto to make up a total volume of 100 μt. The above reaction mixture was set in the TaKaRa PCR Thermal Cycler SP, and 30 cycles of reaction, each cycle comprising 96° C. for 1 minute and 68° C. for 4 minutes, were performed.

After the termination of the reaction, 5 μL of the reaction mixture was electrophoresed with 1.0% agarose gel, and a desired DNA fragment having a size of about 0.9 kbp was confirmed. The remainder of the reaction mixture for PCR was collected, and the mixture was subjected to ethanol precipitation. The DNA collected after the ethanol precipitation was suspended in a sterile water, to make up a total volume of the reaction mixture of 50 μL, the reaction mixture was digested with the restriction enzyme NcoI, and the digest was electrophoresed with 1.0% agarose gel, thereby extracting and purifying an NcoI, NcoI digest, to give an NcoI-NcoI-digested DNA fragment.

Next, the pCold14-H271 constructed in Example 46-(1)-(i) was digested with NcoI, and the terminals of the digest were subjected to a dephosphorization treatment to prepare a product, and the product was mixed with the above-mentioned DNA fragment having a size of about 0.9 kbp, and ligated with the DNA ligation kit. Thereafter, *Escherichia coli* JM109 was transformed with 10 μL of the ligation reaction mixture, and the resulting transformant was grown on an LB medium (containing 50 μg/mL ampicillin) containing agar in a concentration of 1.5% (w/v).

The plasmid inserted with the DNA fragment encoding a protein in which H-296 and H-271 were connected was confirmed by sequencing, and this recombinant plasmid was referred to as pCold14-H296-H271. This pCold14-H296-

H271 is a plasmid containing a nucleotide sequence encoding the amino acid sequence of the amino acid numbers 278-574 of CH-296 and a nucleotide sequence encoding the amino acid sequence of the amino acid numbers 278-549 of CH-296, connected with an amino acid "A" inserted therebetween. The protein was named H296-H271, and an amino acid sequence thereof is shown in SEQ ID NO: 36 of Sequence Listing, and the nucleotide sequence is shown SEQ ID NO: 37 of Sequence Listing.

(2) Expression and Purification of H296-H271

*Escherichia coli* BL21 was transformed with pCold14-H296-H271 prepared in the above-mentioned (1), and the expression and purification of H296-H271 were carried out in the same manner as in Example 1-(2). Here, the amounts of liquid volume of the culture medium, the cell disruption solution, the resin volume, buffer A, buffer B, buffer D, the fractionated solution, and the concentrate were properly changed as occasion demands. The concentrate obtained was analyzed by 10% SDS-PAGE, and as a result, a target protein having a molecular weight of about 62 kDa was detected in a nearly single band, and this was referred to as H296-H271. Thereafter, the concentration of the protein was determined with the MicroBCA kit, and as a result, the concentration was 1.1 mg/mL (about 17.7 μM, calculated from the molecular weight). Incidentally, it is assumed that the N-terminal is methionine-digested, and becomes Ala.

Example 47

Expansion of Lymphocytes (Lymphokine-Activated Cells) Using Anti-CD3 Antibody and FN Fragments (H271-H296 and H296-H271)

(1) Immobilization of Anti-Human CD3 Antibody and Two Kinds of FN Fragments

An anti-human CD3 antibody and two kinds of the FN fragments, namely, H271-H296 and H296-H271, were immobilized in the same manner as in Example 43-(1) to a culture equipment used in the following experiment, except that as the buffer used upon the immobilization, the ACD-A solution (pH 5.0) or PBS was used, and that the FN fragment was added so as to have a final concentration of 11 to 16 μg/mL Here, the concentration of the FN fragment used was controlled in order to match the amount of each FN fragment immobilized to the culture equipment to a given level. Upon the immobilization, as the FN fragments, H271-H296 prepared in Example 45 and H296-H271 prepared in Example 46 were used.

(2) Expansion of Lymphocytes

The expansion of the lymphocytes was carried out in the same manner as in Example 43-(2), except that on the zeroth day from the initiation of culture, the plate immobilized with anti-human CD3 antibody or the plate immobilized with the anti-human CD3 antibody and the FN fragment prepared in Example 47-(1) was used, and that the culture was carried out for 15 days. On the fifteenth day from the initiation of the culture, the number of viable cells was counted by trypan blue staining method, and an expansion fold was calculated by comparing the number of the counted cells with the number of cells at the initiation of culture. The results are shown in Table 46.

TABLE 46

| FN Fragment | Expansion Fold (fold) |
| --- | --- |
| Control (Without Immobilization with FN Fragment) | 368 |
| H271-H296 | 677 |
| H296-H271 | 690 |

As shown in Table 46, the groups in which the culture equipments immobilized with the FN fragments, namely, H271-H296 and H296-H271, at an early stage of the expansion of the lymphocytes were used gave high expansion folds as compared to the control group. In other words, it was clarified that the two kinds of the FN fragments, namely H271-H296 and H296-H271, are suitably used during the expansion of the lymphocytes.

(3) Analyses of CD45RA-Positive-CCR7-Positive Cells, CD45RA-Positive-CD62L-Positive Cells, and CD45RA-Positive-CCR7-Positive-CD62L-Positive Cells The cells prepared in Example 47-(2) were analyzed for CD45RA-positive-CCR7-positive cells, CD45RA-positive-CD62L-positive cells, CD45RA-positive-CCR7-positive-CD62L-positive cells in the same manner as in Example 43-(3). The results are shown in Table 47.

TABLE 47

| FN Fragment | $CD45RA^+$ $CCR7^+$ (%) | $CD45RA^+$ $CD62L^+$ (%) | $CD45RA^+$ $CCR7^+$ $CD62L^+$ (%) |
| --- | --- | --- | --- |
| Control (Without Immobilization with FN Fragment) | 27.6 | 66.2 | 24.0 |
| H271-H296 | 81.4 | 88.9 | 79.7 |
| H296-H271 | 76.5 | 82.4 | 73.2 |

As shown in Table 47, the groups in which the culture equipments immobilized with the FN fragments, namely H271-H296 and H296-H271, at an early stage of the expansion of the lymphocytes were used gave higher effects in the proportions of the CD45RA-positive-CCR7-positive cell population, the CD45RA-positive-CD62L-positive cell population, and the CD45RA-positive-CCR7-positive-CD62L-positive cell population, as compared to the control group. According to the example, it was clarified that the naive T-like cells could be proliferated in a high efficiency by using the two kinds of the FN fragments, namely H271-H296 and H296-H271.

Example 48

Induction of CTLs Having Specific Cytotoxic Activity Using FN Fragments (1) Immobilization of Each of FN Fragments Each of three kinds of FN Fragments, H296-H296, H271-H296, and H296-H271, was immobilized to a culture equipment used in the following experiment. Concretely, an ACD-A solution (pH 5.0) containing FN fragments having a final concentration of 5 to 10 μg/mL was added in a volume of 0.24 mL/well each to the 24-well cell culture plate, or in a volume of 0.09 mL/well each to the 48-well cell culture plate, and the culture equipments were incubated overnight at 4° C. The culture equipments were washed before use twice with PBS, and then once with the RPMI 1640 medium, and the culture equipments were subjected to each experiment. Here, the concentration of the FN fragment used was controlled in order to match the amount of each FN fragment immobilized to the culture equipment to a given level. Upon the immobilization, as the FN fragments, H296-H296 prepared in Example 1, H271-H296 prepared in Example 45, and H296-H271 prepared in Example 46 were used.

(2) Induction of Anti-Influenza Virus Memory CTLs

Using the PBMCs isolated and stored according to the method described in Example 2-(1), the induction of the anti-influenza virus memory CTLs was carried out in the same manner as in Example 2-(3). During the induction, the 48-well cell culture plate prepared in Example 48-(1) was used (as the control, a plate without immobilization of the FN fragment being used) at the initiation of the culture, and the responder cells were added in a volume of 0.4 mL/well each. On the seventh day of the culture, the 24-well cell culture plate prepared in Example 48-(1) was used (as the control, a plate without the immobilization of the FN fragment being used). The cell proliferation rate after 14 days of the culture is shown in Table 48.

TABLE 48

| FN Fragment | Cell Proliferation Rate (fold) |
|---|---|
| Control (Without Immobilization With FN Fragment) | 0.8 |
| H296-H296 | 3.1 |
| H271-H296 | 3.1 |
| H296-H271 | 2.1 |

As shown in Table 48, the groups in which the FN fragment was used showed high proliferation rates as compared to the control group without use. In other words, it was clarified that the proliferation rates of the cells were enhanced by using the FN fragment during the induction of CTLs.

Example 49

Expansion of CTLs of Example 48 Without Using Feeder Cells Assuming 60 mL of Blood Collection (1) Immobilization of Anti-CD3 Antibody and Each of FN Fragments An anti-CD3 antibody and three kinds of the FN fragments were immobilized to a culture equipment used in the following experiment for the expansion of CTLs without using the feeder cells. Concretely, an ACD-A solution (pH 5.0) containing the anti-CD3 antibody (final concentration: 5 µg/mL) and the FN fragments of the same concentration as in Example 48-(1) was added to the 48-well cell culture plate in a volume of 0.09 mL/well each, and the culture equipment was incubated overnight at 4° C. (the control being immobilized only with the anti-CD3 antibody). In addition, the above-mentioned plate was washed twice with PBS before use, and then washed once with the RPMI 1640.

(2) Expansion of CTLs Without Using Feeder Cells

The CTLs in an amount of $1 \times 10^5$ cells which were prepared in Example 48-(2) were subjected to expansion in the same manner as in Example 29-(2). During the stimulation, the 48-well culture plate prepared in Example 49-(1) was used. The cell proliferation rate after 15 days of the culture is shown in Table 49.

TABLE 49

| | Cell Proliferation Rate (fold) | |
|---|---|---|
| FN Fragment | During the Expansion | from the Induction |
| Control (Without Immobilization with FN Fragment) | 29.1 | 23.3 |
| H296-H296 | 59.8 | 178.2 |
| H271-H296 | 41.7 | 128.7 |
| H296-H271 | 89.3 | 197.5 |

As shown in Table 49, the group in which the FN fragment was used during the induction and the expansion showed high proliferation rates as compared to the control group without use. In other words, it was shown that the expansion of the CTLs could be carried out without using the feeder cells, by using the FN fragment during the induction and the expansion.

Example 50

Assay of Cytotoxic Activity of CTLs of Example 49

The specific cytotoxic activity of CTLs for the CTLs obtained in Example 49-(2) was assayed in the same manner as in Example 27. The results for the cytotoxic activity after the expansion of CTLs are shown in Table 50, and the effects of activity maintenance are shown in Table 51. Here, as to the results for the cytotoxic activity, no test was conducted at an E/T ratio of 30, and as to the effects of maintaining the cytotoxic activity, the calculations were made on two points, E/T ratios of 3 and 1.

TABLE 50

| | Cytotoxic Activity (%) After Expansion of CTLs E/T Ratio | | |
|---|---|---|---|
| FN Fragment | 10 | 3 | 1 |
| Control (Without Immobilization with FN Fragment) | 44.4 | 15.2 | 2.8 |
| H296-H296 | 66.1 | 46.8 | 18.3 |
| H271-H296 | 76.6 | 46.7 | 20.9 |
| H296-H271 | 80.2 | 50.7 | 25.9 |

TABLE 51

| | Effect of Activity Maintenance (%) E/T Ratio | |
|---|---|---|
| FN Fragment | 3 | 1 |
| Control (Without Immobilization with FN Fragment) | 35.2 | 8.8 |
| H296-H296 | 86.2 | 52.3 |
| H271-H296 | 64.8 | 44.1 |
| H296-H271 | 66.7 | 45.2 |

The cytotoxic activity against the Calcein-labeled target cells cultured in the absence of the peptide was almost 0%, confirming that the non-specific activity was not found therefor. Regarding the cytotoxic activity against the Calcein-labeled target cells cultured in the presence of the peptide, the CTLs of the group in which the FN fragment was used during the induction and the expansion maintained specific, high cytotoxic activities even after the expansion for 15 days, as compared to the control group. In other words, it was clarified that the expansion could be carried out according to a method without using the feeder cells in a state that a specific, high cytotoxic activity was maintained for a long period of time, by using the FN fragment during the induction and the expansion of CTLs.

Example 51

Determination of Content Ratio of TCR Vβ17-Positive-CD8-Positive Cells in Cell Population of CTLs of Example 49

The content ratio of TCR Vβ17-positive-CD8-positive cells was determined for the CTLs in an amount of $2 \times 10^5$ cells prepared in Example 49-(2) in the same manner as in Example 28. The determination results are shown in Table 52.

TABLE 52

| FN Fragment | TCR Vβ17⁺ CD8⁺ (%) |
| --- | --- |
| Control (Without Immobilization with FN Fragment) | 15.8 |
| H296-H296 | 70.5 |
| H271-H296 | 45.0 |
| H296-H271 | 45.3 |

As shown in Table 52, the CTLs in which the FN fragment was used during the induction and the expansion of CTLs showed high content ratios of positive cells, as compared to the control group without use. Here, the CTLs after the induction, in other words those cells before the expansion, had content ratios of TCR Vβ17-positive-CD8-positive cells of from 67.5% to 71.8% for the groups in which the FN fragment was used, and 68.0% for the control group without use. In other words, it was found that the expansion could be carried out while maintaining a high content ratio of the anti-influenza virus memory CTLs, by using the FN fragment during the induction and the expansion of CTLs.

Example 52

Generation of H105-H105Nc-HT and H105-H105Nc (1) Construction of H105-H105Nc-HT Expression Vector In order to allow expression of a modified fibronectin fragment (H105-H105Nc-HT) in which two of H-105's were connected, an expression vector was constructed in the manner described below.

(i) Construction of pCold14-H105 Vector

Synthetic primers AID-F-Nco and CS1-R-Xba having the nucleotide sequences shown in SEQ ID NOs: 45 and 46 of Sequence Listing were synthesized with a DNA synthesizer, and purified according to a conventional method. The above-mentioned synthetic primer AID-F-Nco is a synthetic DNA having a recognized sequence with a restriction enzyme NcoI in the base numbers 10-15, and further having a nucleotide sequence corresponding to amino acid numbers 460-466 of the amino acid sequence of CH-296 (SEQ ID NO: 7) in the base numbers 18-38. In addition, the synthetic primer CS1-R-Xba is a synthetic DNA having a recognized sequence with a restriction enzyme XbaI in the base numbers 10-15, and further having a nucleotide sequence corresponding to amino acid numbers 574-569 of the amino acid sequence of CH-296 (SEQ ID NO: 7) in the base numbers 19-36.

PCR was carried out using the above-mentioned synthetic primers. The reaction conditions for PCR are given hereinafter. Concretely, about 0.1 μg of the pCold14-H296 constructed in Example 1-(1)-(i) as a template DNA, 10 μL of the 10× Pyrobest Buffer II, 8 μL of the dNTP mixture, 20 pmol of a synthetic primer AID-F-Nco, 20 pmol of a synthetic primer CS1-R-Xba, and 2.5 U Pyrobest DNA Polymerase were added together, and a sterile water was added thereto to make up a total volume of 100 μt. The above reaction mixture was set in the TaKaRa PCR Thermal Cycler SP, and 30 cycles of reaction, each cycle comprising 98° C. for 10 seconds and 68° C. for 1 minute, were performed. After the termination of the reaction, 5 μL of the reaction mixture was electrophoresed with 1.0% agarose gel, and a desired DNA fragment having a size of about 0.35 kbp was confirmed. The remainder of the reaction mixture for PCR was subjected to ethanol precipitation, and the DNA collected was suspended in a sterile water, and subjected to a double digestion with the restriction enzyme NcoI and a restriction enzyme XbaI. The digest was electrophoresed with 1.0% agarose gel, thereby extracting and purifying the NcoI, XbaI digest, to give an NcoI-XbaI-digested DNA fragment.

Next, the pCold14 vector digested with NcoI and XbaI was prepared, and the digest was mixed with the above-mentioned NcoI-XbaI-digested DNA fragment, and ligated with the DNA ligation kit. Thereafter, *Escherichia coli* JM109 was transformed with 10 μL of the ligation reaction mixture, and the resulting transformant was grown on an LB medium (containing 50 μg/mL ampicillin) containing agar in a concentration of 1.5% (w/v). A recombinant plasmid inserted with the desired DNA fragment was referred to as pCold14-H105.

(ii) Construction of pCold14-H105-2 Vector

PCR was carried out using synthetic primers AID-F-Nco and H296-NcoR having the nucleotide sequences shown in SEQ ID NOs: 45 and 11 of Sequence Listing. The reaction conditions for PCR are given hereinafter. Concretely, about 0.1 μg of the pCold14-H296 as a template DNA, 10 μL of the 10× Pyrobest Buffer II, 8 μL of the dNTP mixture, 20 pmol of a synthetic primer AID-F-Nco, 20 pmol of a synthetic primer H296-NcoR, and 2.5 U Pyrobest DNA Polymerase were added together, and a sterile water was added thereto to make up a total volume of 100 μL. The above reaction mixture was set in the TaKaRa PCR Thermal Cycler SP, and 30 cycles of reaction, each cycle comprising 98° C. for 10 seconds and 68° C. for 1 minute, were performed. After the termination of the reaction, 5 μL of the reaction mixture was electrophoresed with 1.0% agarose gel, and a desired DNA fragment having a size of about 0.35 kbp was confirmed. The remainder of the reaction mixture for PCR was subjected to ethanol precipitation, and the DNA collected was suspended in a sterile water, and digested with the restriction enzyme NcoI. The digest was electrophoresed with 1.0% agarose gel, thereby extracting and purifying the NcoI, NcoI digest, to give an NcoI-NcoI-digested DNA fragment.

Next, pCold14-H105 constructed in Example 52-(1)-(i) was digested with NcoI, and the terminals of the digest were subjected to a dephosphorization treatment to prepare a product, and the product was mixed with the above-mentioned DNA fragment having a size of about 0.35 kbp, and ligated with the DNA ligation kit. Thereafter, *Escherichia coli* JM109 was transformed with 10 μL of the ligation reaction mixture, and the resulting transformant was grown on an LB medium (containing 50 μg/mL ampicillin) containing agar in a concentration of 1.5% (w/v). The recombinant plasmid inserted with the desired DNA fragment was referred to as pCold14-H105-2.

(iii) Construction of pColdI-H105-2Nc Vector

PCR was carried out using a synthetic primer H105-NdeF having the nucleotide sequence shown in SEQ ID NO: 21 of Sequence Listing and a synthetic primer H296-HindR having the nucleotide sequence shown in SEQ ID NO: 10 of Sequence Listing. The reaction conditions for PCR are given hereinafter. Concretely, about 0.1 µg of the pCold14-H105-2 constructed in Example 52-(1)-(ii) as a template DNA, 10 µL of the 10× Pyrobest Buffer II, 8 µL of the dNTP mixture, 20 pmol of a synthetic primer H105-NdeF, 20 pmol of a synthetic primer H296-HindR, and 2.5 U Pyrobest DNA Polymerase were added together, and a sterile water was added thereto to make up a total volume of 100 µL. The above reaction mixture was set in the TaKaRa PCR Thermal Cycler SP, and 30 cycles of reaction, each cycle comprising 98° C. for 10 seconds and 68° C. for 1 minute, were performed. After the termination of the reaction, 5 µL of the reaction mixture was electrophoresed with 1.0% agarose gel, and a desired DNA fragment having a size of about 0.7 kbp was confirmed. The remainder of the reaction mixture for PCR was subjected to ethanol precipitation, and the DNA collected was suspended in a sterile water, and subjected to a double digestion with the restriction enzyme NdeI and the restriction enzyme HindIII. The digest was electrophoresed with 1.0% agarose gel, thereby extracting and purifying the NdeI, HindIII digest, to give an NdeI-HindIII-digested DNA fragment.

Next, the pColdI vector subjected to double digestion with the restriction enzyme NdeI and the restriction enzyme HindIII was prepared, and the digest was mixed with the above-mentioned DNA fragment having a size of about 0.7 kbp, and ligated with the DNA ligation kit. Thereafter, *Escherichia coli* JM109 was transformed with 10 µL of the ligation reaction mixture, and the resulting transformant was grown on an LB medium (containing 50 µg/mL ampicillin) containing agar in a concentration of 1.5% (w/v).

The plasmid inserted with a DNA fragment encoding a protein in which two of H-105's were connected was confirmed by sequencing, and this recombinant plasmid was referred to as pColdI-H105-2Nc. This pColdI-H105-2Nc is a plasmid containing a DNA sequence encoding a polypeptide in which two of nucleotide sequences encoding the amino acid sequence of the amino acid numbers 460-574 of CH-296 were connected with an amino acid "AMA" inserted therebetween, the polypeptide having a His tag sequence and methionine at an N-terminal thereof. The protein is named H105-H105Nc-HT, and an amino acid sequence thereof is shown in SEQ ID NO: 47 of Sequence Listing, and a nucleotide sequence thereof is shown in SEQ ID NO: 48 of Sequence Listing.

(2) Expression and Purification of H105-H105Nc-HT

*Escherichia coli* BL21 was transformed with pColdI-H105-2Nc prepared in the above-mentioned (1), and the expression and purification of H105-H105Nc-HT were carried out in the same manner as in Example 22-(2). Here, the amounts of liquid volume of the culture medium, Binding Buffer, Washing Buffer A, Elution Buffer, and the concentrate were properly changed as occasion demands The concentrate obtained was analyzed by SDS-PAGE, and as a result, a target protein having a molecular weight of about 28 kDa was detected in a nearly single band. Thereafter, the concentration of the protein was determined with the MicroBCA kit, and as a result, the concentration of the protein was 1.25 mg/mL (about 44 µM, calculated from the molecular weight).

(3) Purification of H105-H105Nc

A His-tag sequence of a 3 mg portion of the above-mentioned H105-H105Nc-HT purified protein was cleaved with the Factor Xa Cleavage Capture Kit in the same manner as in Example 40-(2) overnight at 4° C., and thereafter the target protein without a His tag was purified. The cleavage of the His tag and the purification of the target protein were performed in accordance with the instruction manual attached to the above-mentioned Kit. The solution after the cleavage was analyzed with the 2100 Bioanalyzer, and as a result, a target protein having a molecular weight of about 26 kDa was detected in a nearly single band. The amino acid sequence of H105-H105Nc is shown in SEQ ID NO: 49 of Sequence Listing, and a nucleotide sequence which is deduced to encode the protein is shown in SEQ ID NO: 50 of Sequence Listing.

Example 53

Generation of 15aaH105-H105 and 15aaH105-H105-HT (1) Construction of 15aaH105-H105-HT Expression Vector In order to allow expression of a modified fibronectin fragment (15aaH105-H105-HT) in which two of H-105's were connected to the amino acid sequence numbers 445-459 of CH-296, an expression vector was constructed in the manner described below.

(i) Construction of pColdI-15aaH105-H105 Vector

A synthetic primer Nde-15aa-F having the nucleotide sequence shown in SEQ ID NO: 38 of Sequence Listing was synthesized with a DNA synthesizer, and purified according to a conventional method. The above-mentioned synthetic primer Nde-15aa-F is a synthetic DNA having a recognized sequence with a restriction enzyme NdeI in the base numbers 7-12, and further having a nucleotide sequence corresponding to amino acid numbers 445-451 of the amino acid sequence of CH-296 (SEQ ID NO: 7) in the base numbers 13-33. PCR was carried out using the above-mentioned synthetic primer and H296-NcoR shown in SEQ ID NO: 11 of Sequence Listing. The reaction conditions for PCR are given hereinafter.

Concretely, about 0.1 µg of the pColdI-H296 constructed in Example 22-(1)-(i) as a template DNA, 20 µL of 5× Prime-STAR Buffer (manufactured by TAKARA BIO INC.), 8 µL of the dNTP mixture, 20 pmol of a synthetic primer Nde-15aa-F, and 20 pmol of a synthetic primer H296-NcoR, and 2.5 U PrimeSTAR HS DNA Polymerase (manufactured by TAKARA BIO INC.) were added together, and a sterile water was added thereto to make up a total volume of 100 µL. The above reaction mixture was set in TaKaRa PCR Thermal Cycler PERSONAL (manufactured by TAKARA BIO INC.), and 30 cycles of reaction, each cycle comprising 96° C. for 10 seconds, 58° C. for 15 seconds, and 72° C. for 30 seconds, were performed under NORM mode.

After the termination of the reaction, 5 µL of the reaction mixture was electrophoresed with 1.0% agarose gel, and a desired DNA fragment having a size of about 0.4 kbp was confirmed. The remainder of the reaction mixture for PCR was collected and subjected to ethanol precipitation, the DNA collected after the ethanol precipitation was suspended in a sterile water so as to make up a total volume of 120 µL, and the reaction mixture was subjected to a double digestion with the restriction enzyme NdeI and the restriction enzyme NcoI. The digest was electrophoresed with 1.0% agarose gel, thereby extracting and purifying the NdeI, NcoI digest, to give an NdeI-NcoI-digested DNA fragment.

Next, the pColdI-H105-2Nc constructed in Example 52-(1)-(iii) was subjected to double digestion with the restriction enzyme NdeI and the restriction enzyme NcoI, and the digest was mixed with the above-mentioned DNA fragment having a size of about 0.4 kbp, and ligated with the DNA ligation kit. Thereafter, *Escherichia coli* JM109 was transformed with 10 µL of the ligation reaction mixture, and the resulting transformant was grown on an LB medium (containing 50 µg/mL ampicillin) containing agar in a concentration of 1.5% (w/v).

The plasmid inserted with a desired DNA fragment encoding a protein in which two of H-105's were connected in the amino acid sequence numbers 445-459 of CH-296 was confirmed by sequencing, and this recombinant plasmid was referred to as pColdI-15aaH105-H105. This pColdI-15aaH105-H105 is a plasmid containing a DNA sequence encoding a polypeptide in which a nucleotide sequence encoding the amino acid numbers 445-459 of CH-296 and a nucleotide sequence encoding the amino acid sequence of the amino acid numbers 460-574 of CH-296 were connected with an amino acid "AMA" inserted therebetween, the polypeptide having a His tag sequence and methionine at an N-terminal thereof. The protein is named 15aaH105-H105-HT, and an amino acid sequence thereof is shown in SEQ ID NO: 39 of Sequence Listing, and a nucleotide sequence thereof is shown in SEQ ID NO: 40 of Sequence Listing.

(2) Expression and Purification of 15aaH105-H105-HT

*Escherichia coli* BL21 was transformed with pColdI-15aaH105-H105 prepared in the above-mentioned (1), and the expression and purification of 15aaH105-H105-HT were carried out in the same manner as in Example 22-(2). Here, the amounts of liquid volume of the culture medium, Binding Buffer, Washing Buffer A, Washing Buffer B, Elution Buffer, and the concentrate were properly changed as occasion demands The concentrate obtained was analyzed with the 2100 Bioanalyzer, and as a result, a target protein having a molecular weight of about 29 kDa was detected in a nearly single band, and the concentration of the protein was 1.5 mg/mL (about 51.7 µM, calculated from the molecular weight).

(3) Purification of 15aaH105-H105

Next, a His-tag sequence of a 3 mg portion of the above-mentioned 15aaH105-H105-HT purified protein was cleaved with the Factor Xa Cleavage Capture Kit in the same manner as in Example 40-(2) overnight at 4° C., and thereafter the target protein without a His tag was purified. The cleavage of the His tag and the purification of the target protein were performed in accordance with the instruction manual attached to the above-mentioned Kit. The solution after the cleavage was analyzed with the 2100 Bioanalyzer, and as a result, a target protein having a molecular weight of about 27 kDa was detected in a nearly single band, and the concentration of the protein was 1 mg/mL (about 37 µM, calculated from the molecular weight). The amino acid sequence of 15aaH105-H105 is shown in SEQ ID NO: 41 of Sequence Listing, and a nucleotide sequence which is deduced to encode the protein is shown in SEQ ID NO: 42 of Sequence Listing.

Example 54

Analyses of CD45RA-Positive-CCR7-Positive Cells, CD45RA-Positive-CD62L-Positive Cells, and CD45RA-Positive-CCR7-Positive-CD62L-Positive Cells of Lymphocytes (Lymphokine-Activated Cells) Cultured Using Each of FN Fragments (H105-H105Nc-HT, H296-H296-HT, and H296-H296) (Direct Addition of FN Fragments)

(1) Immobilization of Anti-Human CD3 Antibody

The anti-human CD3 antibody was immobilized in the same manner as in Example 42-(1) to a culture equipment used in the following experiment, except that the anti-human CD28 antibody and each kind of FN fragments were not immobilized.

(2) Expansion of Lymphocytes

The expansion of the lymphocytes was carried out in the same manner as in Example 42-(2). Here, on the zeroth day from the initiation of culture, the H105-H105Nc-HT generated in Example 52, H296-H296-HT generated in Example 39, or the H296-H296 generated in Example 1 was directly added so as to have a final concentration of 0.67 µg/mL or 0.34 µg/mL On the eleventh day from the initiation of the culture, the cell culture medium of each group was diluted 2-folds with serum-free GT-T503 containing 0.2% human serum albumin, and IL-2 was then added thereto so as to have a final concentration of 500 U/mL On the fourteenth day from the initiation of culture, the number of viable cells was counted by trypan blue staining method, and an expansion fold was calculated by comparing the number of the counted cells with the number of cells at the initiation of culture. The results are shown in Tables 53 and 54.

TABLE 53

| FN Fragment | Amount (µg/mL) | Expansion Fold (fold) |
|---|---|---|
| Control (Without Addition of FN Fragment) | | 130 |
| H105-H105Nc-HT | 0.67 | 339 |
| H105-H105Nc-HT | 0.34 | 302 |

TABLE 54

| FN Fragment | Amount (µg/mL) | Expansion Fold (fold) |
|---|---|---|
| Control (Without Addition of FN Fragment) | | 395 |
| H296-H296-HT | 0.67 | 545 |
| H296-H296 | 0.67 | 441 |

As shown in Tables 53 and 54, the groups with direct addition of the FN fragment, namely H105-H105Nc-HT, H296-H296-HT, or H296-H296, to the culture medium at an early stage of the expansion of the lymphocytes gave high expansion folds as compared to the control group.

(3) Analyses of CD45RA-Positive-CCR7-Positive Cells, CD45RA-Positive-CD62L-Positive Cells, and CD45RA-Positive-CCR7-Positive-CD62L-Positive Cells The cells prepared in Example 54-(2) were analyzed for CD45RA-positive-CCR7-positive cells, CD45RA-positive-CD62L-positive cells, CD45RA-positive-CCR7-positive-CD62L-positive cells in the same manner as in Example 43-(3). The results are shown in Table 55 and Table 56.

TABLE 55

| FN Fragment | Amount (µg/mL) | CD45RA$^+$ CCR7$^+$ (%) | CD45RA$^+$ CD62L$^+$ (%) | CD45RA$^+$ CCR7$^+$ CD62L$^+$ (%) |
|---|---|---|---|---|
| Control (Without Addition of FN Fragment) | | 27.8 | 53.9 | 24.2 |
| H105-H105Nc-HT | 0.67 | 61.6 | 88.6 | 60.9 |
| H105-H105Nc-HT | 0.34 | 59.6 | 82.4 | 57.8 |

TABLE 56

| FN Fragment | Amount (µg/mL) | CD45RA+ CCR7+ (%) | CD45RA+ CD62L+ (%) | CD45RA+ CCR7+ CD62L+ (%) |
|---|---|---|---|---|
| Control (Without Addition of FN Fragment) | | 29.1 | 63.8 | 27.2 |
| H296-H296-HT | 0.67 | 61.9 | 93.6 | 61.1 |
| H296-H296 | 0.67 | 62.2 | 92.6 | 61.4 |

As shown in Tables 55 and 56, the groups with direct addition of the solutions of FN fragments, namely H105-H105Nc-HT, H296-H296-HT, and H296-H296, to the culture medium at an early stage of the expansion of the lymphocytes gave results in higher proportions of the CD45RA-positive-CCR7-positive cell population, the CD45RA-positive-CD62L-positive cell population, and the CD45RA-positive-CCR7-positive-CD62L-positive cell population, as compared to those of the control group. According to the example, it was clarified that the naive T-like cells could be proliferated in a high efficiency even when using the three kinds of the FN fragments in direct addition.

Example 55

Expansion of Lymphocytes (Lymphokine-Activated Cells) Using Anti-CD3 Antibody, Anti-CD28 Antibody and FN Fragments (H296-H296, H296-H296-H296, and H105-H105Nc)

(1) Immobilization of Anti-Human CD3 Antibody, Anti-Human CD28 Antibody and FN Fragments An anti-human CD3 antibody, an anti-human CD28 antibody and a FN fragment, namely, H296-H296, H296-H296-H296, or H105-H105Nc, were immobilized to a culture equipment used in the following experiment in the same manner as in Example 42-(1), except that the FN fragment was added so as to have a final concentration of from 3 to 25 µg/mL Here, the concentration of the FN fragment used was controlled in order to match the amount of each FN fragment immobilized to the culture equipment to a given level. Upon the immobilization, as the FN fragment, H296-H296 prepared in Example 1, H296-H296-H296 prepared in Example 40, or H105-H105Nc prepared in Example 52 was used.

(2) Expansion of Lymphocytes

The expansion of the lymphocytes was carried out in the same manner as in Example 42-(2). Here, on the zeroth day from the initiation of culture, the plate immobilized with the anti-human CD3 antibody and the anti-human CD28 antibody or the plate immobilized with the anti-human CD3 antibody, the anti-human CD28 antibody, and the FN fragment, prepared in Example 55-(1) was used. On the fourth day from the initiation of culture, the culture medium was diluted with 0.5% GT-T503, so as to have a cell concentration of each group of 0.02×10$^6$ cells/mL, 6 mL of the dilution was then transferred to a 12.5 cm$^2$ cell culture flask, and IL-2 was added thereto so as to have a final concentration of 500 U/mL The culture was continued, and on the seventh day, the culture medium was diluted with 0.5% GT-T503 so as to have a concentration of 0.1×10$^6$ cells/mL, 6 mL of the dilution was then transferred to a 12.5 cm$^2$ cell culture flask, and IL-2 was added thereto so as to have a final concentration of 500 U/mL On the tenth day from the initiation of culture, the number of viable cells was counted by trypan blue staining method, and an expansion fold was calculated by comparing the number of the counted cells with the number of cells at the initiation of culture. The results are shown in Table 57.

TABLE 57

| FN Fragment | Expansion Fold (fold) |
|---|---|
| Control (Without Immobilization with FN Fragment) | 319 |
| H296-H296 | 376 |
| H105-H105Nc | 409 |
| H296-H296-H296 | 505 |

As shown in Table 57, the groups in which the culture equipments immobilized with the anti-CD3 antibody, the anti-CD28 antibody, and the FN fragment, namely, H296-H296, H105-H105Nc, or H296-H296-H296, at an early stage of the expansion of the lymphocytes were used gave high expansion folds as compared to the control group. In other words, it was clarified that the FN fragment, namely H296-H296, H105-H105Nc, or H296-H296-H296, is suitably used during the expansion of the lymphocytes using the anti-CD3 antibody and the anti-CD28 antibody.

(3) Analyses of CD45RA-Positive-CCR7-Positive Cells, CD45RA-Positive-CD62L-Positive Cells, and CD45RA-Positive-CCR7-Positive-CD62L-Positive Cells On the tenth day from the initiation of culture, the cells prepared in Example 55-(2) were analyzed for CD45RA-positive-CCR7-positive cells, CD45RA-positive-CD62L-positive cells, CD45RA-positive-CCR7-positive-CD62L-positive cells in the same manner as in Example 43-(3). The results are shown in Table 58.

TABLE 58

| FN Fragment | CD45RA+ CCR7+ (%) | CD45RA+ CD62L+ (%) | CD45RA+ CCR7+ CD62L+ (%) |
|---|---|---|---|
| Control (Without Immobilization with FN Fragment) | 41.2 | 75.0 | 19.6 |
| H296-H296 | 54.6 | 89.6 | 53.5 |
| H105-H105Nc | 53.1 | 77.4 | 50.3 |
| H296-H296-H296 | 44.3 | 81.0 | 41.1 |

As shown in Table 58, the groups in which the culture equipments immobilized with the anti-CD3 antibody, the anti-CD28 antibody, and the FN fragment, namely H296-H296, H105-H105Nc, or H296-H296-H296, at an early stage of the expansion of the lymphocytes were used gave results in higher proportions of the CD45RA-positive-CCR7-positive cell population, the CD45RA-positive-CD62L-positive cell population, and the CD45RA-positive-CCR7-positive-CD62L-positive cell population, as compared to those of the control group. According to the example, it was clarified that the naive T-like cells could be proliferated in a high efficiency by using the FN fragments, namely H296-H296, H105-H105Nc, and H296-H296-H296.

Example 56

Expansion of Lymphocytes (Lymphokine-Activated Cells) Using Anti-CD3 Antibody and FN Fragment (15aaH105-H105)

(1) Immobilization of Anti-Human CD3 Antibody and FN Fragment

An anti-human CD3 antibody and the FN fragment, namely, 15aaH105-H105, were immobilized in the same manner as in Example 43-(1), to a culture equipment used in the following experiment, except that as a buffer PBS was used during the immobilization, and that the FN fragment was added so as to have a final concentration of 10 μg/mL During the immobilization, as the FN fragment, the 15aaH105-H105 prepared in Example 53 was used.

(2) Expansion of Lymphocytes

The expansion of the lymphocytes was carried out in the same manner as in Example 43-(2). Here, on the zeroth day from the initiation of culture, the plate immobilized with the anti-human CD3 antibody or the plate immobilized with the anti-human CD3 antibody and the FN fragment, prepared in Example 56-(1) was used, and the procedures of the eighth day from the initiation of culture in Example 43-(2) were carried out on the seventh day in the example. On the fourteenth day from the initiation of culture, the number of viable cells was counted by trypan blue staining method, and an expansion fold was calculated by comparing the number of the counted cells with the number of cells at the initiation of culture. The results are shown in Table 59.

TABLE 59

| FN Fragment | Expansion Fold (fold) |
|---|---|
| Control (Without Immobilization with FN Fragment) | 313 |
| 15aaH105-H105 | 643 |

As shown in Table 59, the group in which the culture equipment immobilized with the FN fragment, namely, 15aaH105-H105, at an early stage of the expansion of the lymphocytes was used gave a high expansion fold as compared to the control group. In other words, it was clarified that the FN fragment, namely 15aaH105-H105, is suitably used during the expansion of the lymphocytes.

(3) Analyses of CD45RA-Positive-CCR7-Positive Cells, CD45RA-Positive-CD62L-Positive Cells, and CD45RA-Positive-CCR7-Positive-CD62L-Positive Cells The cells prepared in Example 56-(2) were analyzed for CD45RA-positive-CCR7-positive cells, CD45RA-positive-CD62L-positive cells, CD45RA-positive-CCR7-positive-CD62L-positive cells in the same manner as in Example 43-(3). The results are shown in Table 60.

TABLE 60

| FN Fragment | CD45RA$^+$ CCR7$^+$ (%) | CD45RA$^+$ CD62L$^+$ (%) | CD45RA$^+$ CCR7$^+$ CD62L$^+$ (%) |
|---|---|---|---|
| Control (Without Immobilization with FN Fragment) | 25.8 | 64.2 | 24.0 |
| 15aaH105-H105 | 76.3 | 88.4 | 76.1 |

As shown in Table 60, the group in which the culture equipment immobilized with the FN fragment, namely 15aaH105-H105, at an early stage of the expansion of the lymphocytes was used gave results in higher proportions of the CD45RA-positive-CCR7-positive cell population, the CD45RA-positive-CD62L-positive cell population, and the CD45RA-positive-CCR7-positive-CD62L-positive cell population, as compared to those of the control group. According to the example, it was clarified that the naive T-like cells could be proliferated in a high efficiency by using the FN fragment, namely 15aaH105-H105.

Example 57

Induction of CTLs Having Specific Cytotoxic Activity Using FN Fragments (1) Immobilization of Each of FN Fragments Each of three kinds of FN Fragments, H296-H296, H105-H105Nc, and 15aaH105-H105, was immobilized to a culture equipment used in the following experiment. Concretely, an ACD-A solution (pH 5.0) or PBS, containing FN fragments having a final concentration of 5 to 10 μg/mL was added to the 24-well cell culture plate in a volume of 0.24 mL/well each, and the culture equipments were incubated overnight at 4° C. The culture equipments were washed before use twice with PBS, and once with the RPMI 1640 medium, and the culture equipments were subjected to each experiment. Here, regarding the concentration and the immobilization solution of the FN fragment, the concentration of the FN fragment used was controlled in order to match the amount of each FN fragment immobilized to the culture equipment to a given level. Upon the immobilization, as the FN fragments, H296-H296 prepared in Example 1, H105-H105Nc prepared in Example 52, and 15aaH105-H105 prepared in Example 53 were used.

(2) Induction of Anti-Influenza Virus Memory CTLs

The induction of the anti-influenza virus memory CTLs was carried out by partially modifying the method of Example 2-(3). At the initiation of culture, the 24-well cell culture plate prepared in Example 57-(1) was used, and the H296-H296 to be directly added was added to the wells prepared in the same manner as those of the control, so as to have a final concentration of 1 μg/mL In addition, a test group with addition of CpG (CpG-C DNA: DNA shown in SEQ ID NO: 43 of Sequence Listing: Hycult Biotechnology) was set. CpG is a known oligonucleotide which has been known to have an action of activating immune cells. The CpG was added so as to have a final concentration of 1 μg/mL or 5 μg/mL On the seventh day of culture, no re-stimulation by the peptide-pulsed antigen-presenting cells was carried out, and in the same manner as in the fifth day, a half of the supernatant of the culture was removed, and a medium containing IL-2 was then added thereto in a volume of 1 mL each, and the culture was continued for 9 days. The cell proliferation rate is shown in Table 61.

TABLE 61

| FN Fragment | Immobilization or Direct Addition | Cell Proliferation Rate (fold) |
|---|---|---|
| Control (Without Immobilization with FN Fragment) | | 1.1 |
| H296-H296 | Immobilization | 2.9 |
| H105-H105Nc | Immobilization | 3.0 |
| 15aaH105-H105 | Immobilization | 2.7 |
| H296-H296 | Direct Addition (1 μg/mL) | 3.3 |
| CpG | Direct Addition (1 μg/mL) | 1.5 |
| CpG | Direct Addition (5 μg/mL) | 2.1 |

As shown in Table 61, the groups in which the FN fragment was used showed high proliferation rates as compared to the control group without use. In addition, CpG showed high proliferation rates as compared to the control, but the proliferation rates came shorter than those of the FN fragments. In other words, it was clarified that the proliferation rates of the cells were enhanced by using the FN fragment during the induction of CTLs, and it was shown that the proliferation rate was beyond that of CpG.

Example 58

Expansion of CTLs of Example 57 Without Using Feeder Cells Assuming 60 mL of Blood Collection (1) Immobilization of Anti-CD3 Antibody and Each of FN Fragments An anti-CD3 antibody and three kinds of the FN fragments were immobilized to a culture equipment used in the following experiment for the expansion of CTLs without using the feeder cells. Concretely, an ACD-A solution (pH 5.0) or PBS, containing the anti-CD3 antibody (final concentration: 1 μg/mL) and the FN fragment of the same concentration as in Example 57-(1), was added to the 48-well cell culture plate in a volume of 0.1 mL/well, and the culture equipment was incubated overnight at 4° C. (the control being immobilized only with the anti-CD3 antibody). In addition, the above-mentioned plate was washed twice with PBS before use, and then washed once with the RPMI 1640.

(2) Expansion of CTLs Without Using Feeder Cells

The CTLs in an amount of $2 \times 10^5$ cells which were prepared in Example 57-(2) were expanded in the same manner as in Example 29-(2). During the stimulation, the 48-well culture plate prepared in Example 58-(1) was used, and the group with direct addition was added according to the concentration of Example 57-(2). In addition, the days of subculture were changed to the fourth day, the seventh day, and the tenth day, and the culture was continued for 14 days. The cell proliferation rate after 14 days is shown in Table 62.

TABLE 62

| FN Fragment | Immobilization or Direct Addition | Cell Proliferation Rate (fold) | |
|---|---|---|---|
| | | During the Expansion | from the Induction |
| Control (Without Immobilization with FN Fragment) | | 19.7 | 21.4 |
| H296-H296 | Immobilization | 68.4 | 196.4 |
| H105-H105Nc | Immobilization | 73.2 | 214.4 |
| 15aaH105-H105 | Immobilization | 76.9 | 209.7 |
| H296-H296 | Direct Addition (1 μg/mL) | 29.5 | 98.0 |
| CpG | Direct Addition (1 μg/mL) | 1.2 | 1.8 |
| CpG | Direct Addition (5 μg/mL) | 16.2 | 33.9 |

As shown in Table 62, the groups in which the FN fragment was used during the induction and the expansion showed high proliferation rates, as compared to the control group or the groups in which CpG was used. In other words, the expansion of the CTLs could be carried out without using the feeder cells by using the FN fragment during the induction and the expansion.

Example 59

Assay of Cytotoxic Activity of CTLs of Example 58

The specific cytotoxic activity of CTLs for the CTLs obtained in Example 58-(2) was assayed in the same manner as in Example 27. The results for the cytotoxic activity after the expansion of CTLs are shown in Table 63. Here, no test was conducted at an E/T ratio of 30.

TABLE 63

| FN Fragment | Immobilization or Direct Addition | Cytotoxic Activity (%) After Expansion of CTLs E/T Ratio | | |
|---|---|---|---|---|
| | | 10 | 3 | 1 |
| Control (Without Immobilization with FN Fragment) | | 31.7 | 12.1 | 1.2 |
| H296-H296 | Immobilization | 66.1 | 35.9 | 13.5 |
| H105-H105Nc | Immobilization | 65.4 | 35.0 | 12.3 |
| 15aaH105-H105 | Immobilization | 58.4 | 24.3 | 6.3 |
| H296-H296 | Direct Addition (1 μg/mL) | 77.1 | 63.3 | 27.7 |
| CpG | Direct Addition (1 μg/mL) | n.t. | 25.0 | 8.5 |
| CpG | Direct Addition (5 μg/mL) | 41.5 | 14.5 | 6.5 | n.t.: not tested.

The cytotoxic activity against the Calcein-labeled target cells cultured in the absence of the peptide was almost 0%, confirming that the non-specific activity was not found therefor. Regarding the cytotoxic activity against the Calcein-labeled target cells cultured in the presence of the peptide, the CTLs of the groups in which the FN fragment was used during the induction and the expansion maintained specific, high cytotoxic activities even after the expansion for 14 days, as compared to the control group or the group in which CpG was used. In other words, it was clarified that the expansion could be carried out according to a method without using the feeder cells in a state that a specific, high cytotoxic activity was maintained for a long period of time, by using the FN fragment during the induction and the expansion of CTLs.

Example 60

Determination of Content Ratio of TCR Vβ17-Positive-CD8-Positive Cells in Cell Population of CTLs of Example 58

The content ratio of TCR Vβ17-positive-CD8-positive cells was determined for the CTLs in an amount of $2 \times 10^5$ cells prepared in Example 58-(2) in the same manner as in Example 28. The determination results are shown in Table 64.

TABLE 64

| FN Fragment | Immobilization or Direct Addition | TCR Vβ17+ CD8+ (%) |
|---|---|---|
| Control (Without Immobilization with FN Fragment) | | 6.8 |
| H296-H296 | Immobilization | 30.4 |
| H105-H105Nc | Immobilization | 29.8 |
| 15aaH105-H105 | Immobilization | 25.0 |
| H296-H296 | Direct Addition (1 μg/mL) | 77.7 |
| CpG | Direct Addition (1 μg/mL) | 7.9 |
| CpG | Direct Addition (5 μg/mL) | 10.4 |

The CTLs in which the FN fragment was used during the induction and the expansion of CTLs showed high content ratios of positive cells, as compared to the control group or the group in which CpG was used. Here, the CTLs after the induction, in other words those cells before the expansion, had content ratios of TCR Vβ17-positive-CD8-positive cells of from 54.0% to 64.4% for the groups in which the FN fragment was used, 43.7% for the control group without use, and from 42.0% to 45.8% for the group in which CpG was used. In other words, it was found that the expansion could be carried out while maintaining a high content ratio of the anti-influenza virus memory CTLs, by using the FN fragment during the induction and the expansion of CTLs.

Example 61

Comparison of Immobilization Rate of Each Kind of FN Fragments

An ACD-A solution (pH 5.0) or PBS, containing each kind of FN fragments in an amount of 0 to 25 μg/mL was added to each well of the 96-well cell culture plate in a volume of 40 μL each, to allow the fragment to be immobilized at room temperature for 5 hours. The cell culture plate was washed three times with PBS containing 0.05% Tween 20 (manufactured by SIGMA), and Block Ace diluted 4-folds with PBS was added to each well in a volume of 300 μL each, and the mixture was allowed to stand at room temperature for 1 hour. The cell culture plate was washed three times with PBS containing 0.05% Tween 20, and as a primary antibody HRP-labeled FNH3-8 or mouse anti-human fibronectin CS-1 antibody (manufactured by CHEMICON), each being properly diluted, was added to each well in a volume of 40 μL each, the mixture was allowed to stand at room temperature for 1 hour, and the cell culture plate was then washed three times with PBS containing 0.05% Tween 20. Upon using the mouse anti-human fibronectin CS-1 antibody as a primary antibody, further as a secondary antibody, a properly diluted HRP-labeled rabbit anti-mouse IgM antibody (manufactured by Zymed Laboratories) was added to each well in a volume of 40 μL each, and allowed to stand at room temperature for 1 hour, and the cell culture plate was then washed three times with PBS containing 0.05% Tween 20. After the antibody reaction, ABTS (manufactured by KPL) was added to each well in a volume of 40 μL each, the mixture was allowed to stand at room temperature for about 10 to about 25 minutes, and 150 mM oxalic acid (manufactured by Nakalai Tesque, Inc.) was then added in a volume of 20 μL to stop the reaction. Thereafter, the immobilization rate was evaluated by determining the absorbance at 405 nm. Here, the mouse anti-human fibronectin CS-1 antibody is an antibody that specifically recognizes CS-1, which is a partial region of the fibronectin (see FIG. 1). The results are shown in Table 65, Table 66, and Table 67. Here, the phrase "405 nm (Found Value-Blank)" in the following tables is a value obtained by subtracting the absorbance of each FN fragment having a concentration of 0 μg/mL from the absorbance at each FN fragment concentration.

TABLE 65

| FN Fragment Concentration | 405 nm (Found Value - Blank) Primary Antibody: FNH3-8 Being Used | | |
|---|---|---|---|
| (μg/mL) | CH-296 | H296-H296-HT | H296-H296-H296-HT |
| 25 | 0.859 | 0.965 | 0.991 |
| 10 | | 0.976 | 0.924 |
| 5 | | 0.878 | 0.870 |
| 4 | | 0.843 | 0.810 |
| 3 | | 0.742 | 0.743 |
| 2 | | 0.540 | 0.545 |

TABLE 65-continued

| FN Fragment Concentration | 405 nm (Found Value - Blank) Primary Antibody: FNH3-8 Being Used | | |
|---|---|---|---|
| (μg/mL) | CH-296 | H296-H296-HT | H296-H296-H296-HT |
| 1 | | 0.186 | 0.261 |
| 0.5 | | 0.033 | n.t. | n.t. = not tested

TABLE 66

| FNfr Concentration | 405 nm (Found Value - Blank) Primary Antibody: Mouse Anti-Human Fibronectin C-1 Antibody | | |
|---|---|---|---|
| (μg/mL) | CH-296 | H105-H105Nc | H105-H105Nc-HT |
| 25 | 0.571 | 0.559 | 1.064 |
| 20 | | 0.610 | 1.076 |
| 15 | | 0.628 | 1.211 |
| 10 | | 0.566 | 1.076 |
| 5 | | 0.194 | 1.016 |
| 2.5 | | 0.063 | 0.606 |

TABLE 67

| FNfr Concentration | 405 nm (Found Value - Blank) Primary Antibody: FNH3-8 Being Used | | |
|---|---|---|---|
| (μg/mL) | CH-296 | H271-H296 | H296-H271 |
| 25 | 0.564 | n.t. | n.t. |
| 20 | | 0.603 | n.t. |
| 18 | | 0.610 | n.t. |
| 16 | | 0.594 | n.t. |
| 15 | | n.t. | 0.635 |
| 14 | | 0.605 | n.t. |
| 13 | | n.t. | 0.609 |
| 12 | | 0.639 | n.t. |
| 11 | | n.t. | 0.561 |
| 10 | | 0.600 | n.t. |
| 9 | | n.t. | 0.560 |
| 7 | | n.t. | 0.518 |
| 5 | | n.t. | 0.448 | n.t. = not tested

As a result, it was clarified that H296-H296-HT, H296-H296-H296-HT, H105-H105Nc, H105-H105Nc-HT, H271-H296, and H296-H271 had high immobilization efficiency to the culture plate as compared to that of CH-296.

Example 62

Generation of H105-HT (1) Expression and Purification of H105-HT

*Escherichia coli* BL21 was transformed with the pColdI-H105 prepared in Example 24-(1)-(i), and the expression and purification of H105-HT were carried out in the same manner as in Example 22-(2). Here, the amounts of liquid volume of the culture medium, Binding Buffer, Washing Buffer A, Washing Buffer B, Elution Buffer, and the concentrate were properly changed as occasion demands The concentrate obtained was analyzed with 2100 Bioanalyzer, and as a result, a target protein having a molecular weight of about 14.8 kDa was detected in a nearly single band, and the concentration of the protein was 0.23 mg/mL (about 15.5 μM, calculated from the molecular weight). The protein was named H105-HT, and an amino acid sequence thereof is shown in SEQ ID NO: 51 of Sequence Listing, and the nucleotide sequence is shown SEQ ID NO: 52 of Sequence Listing.

Example 63

Expansion of Lymphocytes (Lymphokine-Activated Cells) Using Anti-CD3 Antibody and FN Fragment (H105-H105Nc-HT or H105-HT)

(1) Immobilization of Anti-Human CD3 Antibody and FN Fragment

The anti-human CD3 antibody was immobilized in the same manner as in Example 54-(1) to a culture equipment used in the following experiment.

(2) Expansion of Lymphocytes

The expansion of the lymphocytes was carried out in the same manner as in Example 54-(2), except that on the zeroth day from the initiation of culture, the plate prepared in Example 63-(1) was used, and that H105-H105Nc-HT generated in Example 52 or H105-HT generated in Example 62 was directly added to the medium so as to have a final concentration of 0.67 or 0.78 μg/mL Here, the concentration of the FN fragment used was controlled in order to match the molar ratio of each FN fragment in the culture medium to a given level. On the fourteenth day from the initiation of culture, the number of viable cells was counted by trypan blue staining method, and an expansion fold was calculated by comparing the number of the counted cells with the number of cells at the initiation of culture. The results are shown in Table 68.

TABLE 68

| FN Fragment | Expansion Fold (fold) |
| --- | --- |
| Control (Without Addition of FN Fragment) | 138 |
| H105-H105Nc-HT | 629 |
| H105-HT | 196 |

As shown in Table 68, the group with direct addition of the FN fragment, namely H105-H105Nc-HT or H105-HT, to the medium at an early stage of the expansion of the lymphocytes gave a high expansion fold as compared to the control group. Further, in a case where a modified FN fragment H105-H105Nc-HT was used, an even higher effect was obtained than that of H105-HT. It was clarified from this matter that the modified FN fragment H105-H105Nc-HT was more suitably used than H105-HT, during the expansion using the anti-CD3 antibody.

(3) Analyses of CD45RA-Positive-CCR7-Positive Cells, CD45RA-Positive-CD62L-Positive Cells, and CD45RA-Positive-CCR7-Positive-CD62L-Positive Cells The cells prepared in Example 63-(2) were analyzed for CD45RA-positive-CCR7-positive cells, CD45RA-positive-CD62L-positive cells, CD45RA-positive-CCR7-positive-CD62L-positive cells in the same manner as in Example 43-(3). The results are shown in Table 69.

TABLE 69

| FN Fragment | CD45RA+ CCR7+ (%) | CD45RA+ CD62L+ (%) | CD45RA+ CCR7+ CD62L+ (%) |
| --- | --- | --- | --- |
| Control (Without Addition of FN Fragment) | 10.4 | 68.7 | 9.5 |
| H105-H105Nc-HT | 52.7 | 81.0 | 48.2 |
| H105-HT | 22.5 | 61.9 | 16.6 |

As shown in Table 69, the group with direct addition of the FN fragment, namely H105-H105Nc-HT or H105-HT, to the medium at an early stage of the expansion of the lymphocytes gave results in high proportions of the CD45RA-positive-CCR7-positive cell population, the CD45RA-positive-CD62L-positive cell population, and the CD45RA-positive-CCR7-positive-CD62L-positive cell population, as compared to those of the control group. Further, in a case where a modified FN fragment H105-H105Nc-HT is used, a higher effect than H105-HT was obtained. According to the example, it was clarified that the naive T-like cells can be proliferated in a higher efficiency than H105-HT by using the modified FN fragment H105-H105Nc-HT.

Example 64

Induction of CTLs Having Specific Cytotoxic Activity Using H296-H296 Fragment (1) Immobilization of H296-H296 Fragment H296-H296 was immobilized to a culture equipment used in the following experiment. Concretely, an ACD-A solution (pH 5.0) containing the H296-H296 having a final concentration of 5 μg/mL was added to the 24-well cell culture plate in a volume of 0.24 mL/well each. These culture equipments were incubated overnight at 4° C. In addition, the above-mentioned plate was washed before use twice with PBS, and then once with the RPMI 1640 medium, and the culture equipments were subjected to an experiment.

(2) Induction of Anti-Cytomegalovirus Memory CTLs

The induction of anti-cytomegalovirus memory CTLs was carried out in accordance with the method of Example 57-(2), except that as the antigen peptide, only an 40 μg/mL epitope peptide derived from cytomegalovirus protein (matrix protein pp65-derived-HLA-A2.1 binding peptide shown in SEQ ID NO: 44 of Sequence Listing) was used. The cell proliferation rate after 9 days of culture is shown in Table 70.

TABLE 70

| FN Fragment | Cell Proliferation Rate (fold) |
| --- | --- |
| Control (Without Immobilization with FN Fragment) | 0.9 |
| H296-H296 | 2.8 |

As shown in Table 70, the group in which the FN fragment was used showed a high proliferation rate as compared to the control group without use. In other words, it was clarified that the proliferation rate of the cells was enhanced by using the FN fragment during the induction of CTLs.

Example 65

Expansion of CTLs of Example 64 Without Using Feeder Cells Assuming 60 mL of Blood Collection (1) Immobilization of Anti-CD3 Antibody and Each of FN Fragments An anti-CD3 antibody and H296-H296 were immobilized to a culture equipment used in the following experiment for the expansion of CTLs without using the feeder cells. Concretely, an ACD-A solution (pH 5.0) containing the anti-CD3 antibody (final concentration: 1 μg/mL) and H296-H296 (final concentration: 5 μg/mL) was added to the 48-well cell culture plate in a volume of 0.1 mL/well each, and the mixture was incubated overnight at 4° C. (the control being immobilized only with the anti-CD3 antibody). In addition, the above-mentioned plate was washed before use twice with PBS, and then once with the RPMI 1640.

(2) Expansion of CTLs Without Using Feeder Cells

The CTLs in an amount of $2\times10^5$ cells which were prepared in Example 64-(2) were expanded in the same manner as in Example 58-(2). The cell proliferation rate after 14 days is shown in Table 71.

TABLE 71

| FN Fragment | Cell Proliferation Rate (fold) | |
|---|---|---|
| | During the Expansion | from the Induction |
| Control (Without Immobilization with FN Fragment) | 10.8 | 10.0 |
| H296-H296 | 68.8 | 193.2 |

As shown in Table 71, the group in which the H296-H296 was used during the induction and the expansion showed a high proliferation rate as compared to the control group without use. In other words, the expansion of CTLs could be carried out without using the feeder cells by using the H296-H296 during the induction and the expansion.

Example 66

Assay of Cytotoxic Activity of CTLs of Example 65

The specific cytotoxic activity of CTLs for the CTLs obtained in Example 65-(2) was assayed in the same manner as in Example 27. The results for the cytotoxic activity after the expansion of CTLs are shown in Table 72, and the effects of activity maintenance are shown in Table 73. Here, as to the effects of maintaining the cytotoxic activity, the calculations were made on two points, E/T ratios of 3 and 1.

TABLE 72

| FN Fragment | Cytotoxic Activity (%) After Expansion of CTLs E/T Ratio | | | |
|---|---|---|---|---|
| | 30 | 10 | 3 | 1 |
| Control (Without Immobilization with FN Fragment) | 18.5 | 9.2 | 0.8 | −1.9 |
| H296-H296 | 52.6 | 29.7 | 12.1 | 6.0 |

TABLE 73

| FN Fragment | Effect of Activity Maintenance (%) E/T Ratio | |
|---|---|---|
| | 3 | 1 |
| Control (Without Immobilization with FN Fragment) | 2.3 | −9.8 |
| H296-H296 | 30.0 | 34.1 |

The cytotoxic activity against the Calcein-labeled target cells cultured in the absence of the peptide was almost 0%, confirming that the non-specific activity was not found therefor. Regarding the cytotoxic activity against the Calcein-labeled target cells cultured in the presence of the peptide, the CTLs of the groups in which the H296-H296 was used during the induction and the expansion maintained specific, high cytotoxic activities even after the expansion for 14 days, as compared to the control group. In other words, it was clarified that the expansion could be carried out according to a method without using the feeder cells in a state that a specific, high cytotoxic activity was maintained for a long period of time, by using H296-H296 during the induction and the expansion of CTLs.

According to the present invention, the method for preparing lymphocytes is provided. The method gives a high cell proliferation rate, and the lymphocytes obtained by the present invention can be suitably used, for example, in adoptive immunotherapy, so that a significant contribution to the field of medicine is expected.

SEQUENCE LISTING FREE TEXT

SEQ ID NO: 1; Partial region of fibronectin named 111-12.
SEQ ID NO: 2; Partial region of fibronectin named 111-13.
SEQ ID NO: 3; Partial region of fibronectin named 111-14.
SEQ ID NO: 4; Partial region of fibronectin named CS-1.
SEQ ID NO: 5; Fibronectin fragment named H296-H296.
SEQ ID NO: 6; Polynucleotide coding Fibronectin fragment named H296-H296.
SEQ ID NO: 7; Fibronectin fragment named CH-296.
SEQ ID NO: 8; Polynucleotide coding Fibronectin fragment named CH-296.
SEQ ID NO: 9; Primer H296-NcoF.
SEQ ID NO: 10; Primer H296-HindR.
SEQ ID NO: 11; Primer H296-NcoR.
SEQ ID NO: 12; Primer NC2-5' UTR.
SEQ ID NO: 13; Designed peptide based on matrix-protein derived from influenza virus.
SEQ ID NO: 14; Primer H296-NdeF.
SEQ ID NO: 15; Primer H296-NdeR.
SEQ ID NO: 16; Fibronectin fragment named H296-H296-H296-HT.
SEQ ID NO: 17; Polynucleotide coding Fibronectin fragment named H296-H296-H296-HT.
SEQ ID NO: 18; Primer CH296-NdeF.
SEQ ID NO: 19; Fibronectin fragment named CH296-CH296-HT.
SEQ ID NO: 20; Polynucleotide coding Fibronectin fragment named CH296-CH296-HT.
SEQ ID NO: 21; Primer H105-NdeF.
SEQ ID NO: :22; Fibronectin fragment named H105-H105-HT.
SEQ ID NO: 23; Polynucleotide coding Fibronectin fragment named H105-H105-HT.
SEQ ID NO: 24; Primer CS1-NdeR.
SEQ ID NO: 25; Fibronectin fragment named H296-H296-HT.
SEQ ID NO: 26; Polynucleotide coding Fibronectin fragment named H296-H296-HT.
SEQ ID NO: 27; Fibronectin fragment named H296-H296-H296.
SEQ ID NO: 28; Polynucleotide coding Fibronectin fragment named H296-H296-H296.
SEQ ID NO: 29; Fibronectin fragment named H105-H105.
SEQ ID NO: 30; Polynucleotide coding Fibronectin fragment named H105-H105.
SEQ ID NO: 31; Primer H271-NcoR.
SEQ ID NO: 32; Fibronectin fragment named H271-H296.
SEQ ID NO: 33; Polynucleotide coding Fibronectin fragment named H271-H296.
SEQ ID NO: 34; Primer 12-Nco-F2.
SEQ ID NO: 35; Primer H271-BamR.
SEQ ID NO: 36; Fibronectin fragment named H296-H271.

SEQ ID NO: 37; Polynucleotide coding Fibronectin fragment named H296-H271.
SEQ ID NO: 38; Primer Nde-15aa-F.
SEQ ID NO: 39; Fibronectin fragment named 15aaH105-H105-HT.
SEQ ID NO: 40; Polynucleotide coding Fibronectin fragment named 15aaH105-H105-HT.
SEQ ID NO: 41; Fibronectin fragment named 15aaH105-H105.
SEQ ID NO: 42; Polynucleotide coding Fibronectin fragment named 15aaH105-H105.
SEQ ID NO: 43; Oligonucleotide CpG-C DNA.
SEQ ID NO: 44; Designed peptide based on matrix-protein derived from pp65.
SEQ ID NO: 45; Primer AID-F-Nco
SEQ ID NO: 46; Primer CS1-R-Xba
SEQ ID NO: 47; Fibronectin fragment named H105-H105Nc-HT
SEQ ID NO: 48; Polynucleotide coding Fibronectin fragment named H105-H105Nc-HT
SEQ ID NO: 49; Fibronectin fragment named H105-H105Nc
SEQ ID NO: 50; Polynucleotide coding Fibronectin fragment named H105-H105Nc
SEQ ID NO: 51; Fibronectin fragment named H105-HT
SEQ ID NO: 52; Polynucleotide coding Fibronectin fragment named H105-HT

The invention claimed is:

1. A method for preparing lymphocytes, comprising the step of culturing the lymphocytes in the presence of an anti-CD3 antibody, interleukin-2 and SEQ ID NO: 5, wherein the lymphocytes are antigen-specific cytotoxic T lymphocytes or lymphokine-activated cells.

2. The method according to claim 1, further comprising the step of transducing a foreign gene into the lymphocytes.

3. The method according to claim 2, wherein the foreign gene is transduced with a retroviral vector, an adenoviral vector, an adeno-associated viral vector, a lentiviral vector, or simian viral vector.

4. The method according to claim 1, wherein the lymphocytes are antigen-specific cytotoxic T lymphocytes and the cytotoxicity activity of the antigen-specific cytotoxic T lymphocytes is greater than the cytotoxicity of antigen-specific cytotoxic T lymphocytes cultured in the absence of polypeptide (X).

5. The method according to claim 4, wherein the greater cytotoxic activity of the antigen-specific cytotoxic T lymphocytes is maintained at day 14 of culture.

* * * * *

SEQUENCE LISTING

```
<160> NUMBER OF SEQ ID NOS: 53

<210> SEQ ID NO 1
<211> LENGTH: 92
<212> TYPE: PRT
<213> ORGANISM: Artificial Sequence
<220> FEATURE:
<223> OTHER INFORMATION: partial region of fibronectin named III-12

<400> SEQUENCE: 1

Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
            20                  25                  30

Arg Val Arg Val Thr Pro Lys Glu Lys Thr Gly Pro Met Lys Glu Ile
        35                  40                  45

Asn Leu Ala Pro Asp Ser Ser Ser Val Val Ser Gly Leu Met Val
    50                  55                  60

Ala Thr Lys Tyr Glu Val Ser Val Tyr Ala Leu Lys Asp Thr Leu Thr
65                  70                  75                  80

Ser Arg Pro Ala Gln Gly Val Val Thr Thr Leu Glu
                85                  90

<210> SEQ ID NO 2
<211> LENGTH: 89
<212> TYPE: PRT
<213> ORGANISM: Artificial Sequence
<220> FEATURE:
<223> OTHER INFORMATION: partial region of fibronectin named III-13

<400> SEQUENCE: 2

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 3
```

```
<211> LENGTH: 90
<212> TYPE: PRT
<213> ORGANISM: Artificial Sequence
<220> FEATURE:
<223> OTHER INFORMATION: partial region of fibronectin named III-14

<400> SEQUENCE: 3

Ala Ile Asp Ala Pro Ser Asn Leu Arg Phe Leu Ala Thr Thr Pro Asn
1               5                   10                  15

Ser Leu Leu Val Ser Trp Gln Pro Pro Arg Ala Arg Ile Thr Gly Tyr
            20                  25                  30

Ile Ile Lys Tyr Glu Lys Pro Gly Ser Pro Arg Glu Val Val Pro
        35                  40                  45

Arg Pro Arg Pro Gly Val Thr Glu Ala Thr Ile Thr Gly Leu Glu Pro
    50                  55                  60

Gly Thr Glu Tyr Thr Ile Tyr Val Ile Ala Leu Lys Asn Asn Gln Lys
65                  70                  75                  80

Ser Glu Pro Leu Ile Gly Arg Lys Lys Thr
                85                  90

<210> SEQ ID NO 4
<211> LENGTH: 25
<212> TYPE: PRT
<213> ORGANISM: Artificial Sequence
<220> FEATURE:
<223> OTHER INFORMATION: partial region of fibronectin named CS-1

<400> SEQUENCE: 4

Asp Glu Leu Pro Gln Leu Val Thr Leu Pro His Pro Asn Leu His Gly
1               5                   10                  15

Pro Glu Ile Leu Asp Val Pro Ser Thr
            20                  25

<210> SEQ ID NO 5
<211> LENGTH: 594
<212> TYPE: PRT
<213> ORGANISM: Artificial Sequence
<220> FEATURE:
<223> OTHER INFORMATION: fibronectin fragment names H296-H296

<400> SEQUENCE: 5

Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
            20                  25                  30

Arg Val Arg Val Thr Pro Lys Glu Lys Thr Gly Pro Met Lys Glu Ile
        35                  40                  45

Asn Leu Ala Pro Asp Ser Ser Ser Val Val Val Ser Gly Leu Met Val
    50                  55                  60

Ala Thr Lys Tyr Glu Val Ser Val Tyr Ala Leu Lys Asp Thr Leu Thr
65                  70                  75                  80

Ser Arg Pro Ala Gln Gly Val Val Thr Thr Leu Glu Asn Val Ser Pro
                85                  90                  95

Pro Arg Arg Ala Arg Val Thr Asp Ala Thr Glu Thr Thr Ile Thr Ile
            100                 105                 110

Ser Trp Arg Thr Lys Thr Glu Thr Ile Thr Gly Phe Gln Val Asp Ala
        115                 120                 125

Val Pro Ala Asn Gly Gln Thr Pro Ile Gln Arg Thr Ile Lys Pro Asp
    130                 135                 140

Val Arg Ser Tyr Thr Ile Thr Gly Leu Gln Pro Gly Thr Asp Tyr Lys
```

```
            145                 150                 155                 160
Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
                180                 185                 190

Ala Thr Thr Pro Asn Ser Leu Leu Val Ser Trp Gln Pro Arg Ala
        195                 200                 205

Arg Ile Thr Gly Tyr Ile Ile Lys Tyr Glu Lys Pro Gly Ser Pro Pro
210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
            245                 250                 255

Lys Asn Asn Gln Lys Ser Glu Pro Leu Ile Gly Arg Lys Lys Thr Asp
                260                 265                 270

Glu Leu Pro Gln Leu Val Thr Leu Pro His Pro Asn Leu His Gly Pro
            275                 280                 285

Glu Ile Leu Asp Val Pro Ser Thr Ala Met Ala Ile Pro Ala Pro Thr
290                 295                 300

Asp Leu Lys Phe Thr Gln Val Thr Pro Thr Ser Leu Ser Ala Gln Trp
305                 310                 315                 320

Thr Pro Pro Asn Val Gln Leu Thr Gly Tyr Arg Val Arg Val Thr Pro
                325                 330                 335

Lys Glu Lys Thr Gly Pro Met Lys Glu Ile Asn Leu Ala Pro Asp Ser
            340                 345                 350

Ser Ser Val Val Val Ser Gly Leu Met Val Ala Thr Lys Tyr Glu Val
            355                 360                 365

Ser Val Tyr Ala Leu Lys Asp Thr Leu Thr Ser Arg Pro Ala Gln Gly
        370                 375                 380

Val Val Thr Thr Leu Glu Asn Val Ser Pro Pro Arg Arg Ala Arg Val
385                 390                 395                 400

Thr Asp Ala Thr Glu Thr Thr Ile Thr Ile Ser Trp Arg Thr Lys Thr
                405                 410                 415

Glu Thr Ile Thr Gly Phe Gln Val Asp Ala Val Pro Ala Asn Gly Gln
                420                 425                 430

Thr Pro Ile Gln Arg Thr Ile Lys Pro Asp Val Arg Ser Tyr Thr Ile
            435                 440                 445

Thr Gly Leu Gln Pro Gly Thr Asp Tyr Lys Ile Tyr Leu Tyr Thr Leu
        450                 455                 460

Asn Asp Asn Ala Arg Ser Ser Pro Val Val Ile Asp Ala Ser Thr Ala
465                 470                 475                 480

Ile Asp Ala Pro Ser Asn Leu Arg Phe Leu Ala Thr Thr Pro Asn Ser
                485                 490                 495

Leu Leu Val Ser Trp Gln Pro Pro Arg Ala Arg Ile Thr Gly Tyr Ile
            500                 505                 510

Ile Lys Tyr Glu Lys Pro Gly Ser Pro Pro Arg Glu Val Val Pro Arg
        515                 520                 525

Pro Arg Pro Gly Val Thr Glu Ala Thr Ile Thr Gly Leu Glu Pro Gly
    530                 535                 540

Thr Glu Tyr Thr Ile Tyr Val Ile Ala Leu Lys Asn Asn Gln Lys Ser
545                 550                 555                 560

Glu Pro Leu Ile Gly Arg Lys Lys Thr Asp Glu Leu Pro Gln Leu Val
                565                 570                 575
```

Thr Leu Pro His Pro Asn Leu His Gly Pro Glu Ile Leu Asp Val Pro
                580                 585                 590

Ser Thr

<210> SEQ ID NO 6
<211> LENGTH: 1786
<212> TYPE: DNA
<213> ORGANISM: Artificial Sequence
<220> FEATURE:
<223> OTHER INFORMATION: polynucleotide coding fibronectin fragment
      named H296-H296

<400> SEQUENCE: 6

| | | | | | |
|---|---|---|---|---|---|
| atggctattc | ctgcaccaac | tgacctgaag | ttcactcagg | tcacacccac | aagcctgagc | 60 |
| gcccagtgga | caccacccaa | tgttcagctc | actggatatc | gagtgcgggt | gacccccaag | 120 |
| gagaagaccg | gaccaatgaa | agaaatcaac | cttgctcctg | acagctcatc | cgtggttgta | 180 |
| tcaggactta | tggtggccac | caaatatgaa | gtgagtgtct | atgctcttaa | ggacactttg | 240 |
| acaagcagac | cagctcaggg | agttgtcacc | actctggaga | atgtcagccc | accaagaagg | 300 |
| gctcgtgtga | cagatgctac | tgagaccacc | atcaccatta | gctggagaac | caagactgag | 360 |
| acgatcactg | gcttccaagt | tgatgccgtt | ccagccaatg | ccagactcc | aatccagaga | 420 |
| accatcaagc | cagatgtcag | aagctacacc | atcacaggtt | acaaccagg | cactgactac | 480 |
| aagatctacc | tgtacacctt | gaatgacaat | gctcggagct | cccctgtggt | catcgacgcc | 540 |
| tccactgcca | ttgatgcacc | atccaacctg | cgtttcctgg | ccaccacacc | caattccttg | 600 |
| ctggtatcat | ggcagccgcc | acgtgccagg | attaccggct | acatcatcaa | gtatgagaag | 660 |
| cctgggtctc | ctcccagaga | agtggtccct | cggccccgcc | tggtgtcac | agaggctact | 720 |
| attactggcc | tggaaccggg | aaccgaatat | acaatttatg | tcattgccct | gaagaataat | 780 |
| cagaagagcg | agcccctgat | tggaaggaaa | aagacagacg | agcttcccca | actggtaacc | 840 |
| cttccacacc | ccaatcttca | tggaccagag | atcttggatg | ttccttccac | agccatggct | 900 |
| attcctgcac | caactgacct | gaagttcact | caggtcacac | ccacaagcct | gagcgcccag | 960 |
| tggacaccac | ccaatgttca | gctcactgga | tatcgagtgc | gggtgacccc | caaggagaag | 1020 |
| accggaccaa | tgaaagaaat | caaccttgct | cctgacagct | catccgtggt | tgtatcagga | 1080 |
| cttatggtgg | ccaccaaata | tgaagtgagt | gtctatgctc | ttaaggacac | tttgacaagc | 1140 |
| agaccagctc | agggagttgt | caccactctg | gagaatgtca | gcccaccaag | aagggctcgt | 1200 |
| gtgacagatg | ctactgagac | caccatcacc | attagctgga | gaaccaagac | tgagacgatc | 1260 |
| actggcttcc | aagttgatgc | cgttccagcc | aatggccaga | ctccaatcca | gagaaccatc | 1320 |
| aagccagatg | tcagaagcta | caccatcaca | ggtttacaac | caggcactga | ctacaagatc | 1380 |
| tacctgtaca | ccttgaatga | caatgctcgg | agctcccctg | tggtcatcga | cgcctccact | 1440 |
| gccattgatg | caccatccaa | cctgcgtttc | ctggccacca | cccaattc | cttgctggta | 1500 |
| tcatggcagc | cgccacgtgc | caggattacc | ggctacatca | tcaagtatga | agcctgggt | 1560 |
| tctcctccca | gagaagtggt | ccctcggccc | cgccctggtg | tcacagaggc | tactattact | 1620 |
| ggcctggaac | cgggaaccga | atatacaatt | tatgtcattg | ccctgaagaa | taatcagaag | 1680 |
| agcgagcccc | tgattggaag | gaaaaagaga | cgagcttccc | caactggtaa | cccttccaca | 1740 |
| ccccaatctt | catggaccag | agatcttgga | tgttccttcc | acataa | | 1786 |

<210> SEQ ID NO 7
<211> LENGTH: 574
<212> TYPE: PRT

<213> ORGANISM: Artificial Sequence
<220> FEATURE:
<223> OTHER INFORMATION: fibronectin fragment named CH-296

<400> SEQUENCE: 7

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
            130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
            210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
            275                 280                 285

Thr Gln Val Thr Pro Thr Ser Leu Ser Ala Gln Trp Thr Pro Pro Asn
            290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Val Val
                325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
            355                 360                 365

Leu Glu Asn Val Ser Pro Pro Arg Arg Ala Arg Val Thr Asp Ala Thr
            370                 375                 380

Glu Thr Thr Ile Thr Ile Ser Trp Arg Thr Lys Thr Glu Thr Ile Thr
385                 390                 395                 400

```
Gly Phe Gln Val Asp Ala Val Pro Ala Asn Gly Gln Thr Pro Ile Gln
                405                 410                 415
Arg Thr Ile Lys Pro Asp Val Arg Ser Tyr Thr Ile Thr Gly Leu Gln
            420                 425                 430
Pro Gly Thr Asp Tyr Lys Ile Tyr Leu Tyr Thr Leu Asn Asp Asn Ala
        435                 440                 445
Arg Ser Ser Pro Val Val Ile Asp Ala Ser Thr Ala Ile Asp Ala Pro
    450                 455                 460
Ser Asn Leu Arg Phe Leu Ala Thr Thr Pro Asn Ser Leu Leu Val Ser
465                 470                 475                 480
Trp Gln Pro Pro Arg Ala Arg Ile Thr Gly Tyr Ile Ile Lys Tyr Glu
                485                 490                 495
Lys Pro Gly Ser Pro Arg Glu Val Val Pro Arg Pro Arg Pro Gly
            500                 505                 510
Val Thr Glu Ala Thr Ile Thr Gly Leu Glu Pro Gly Thr Glu Tyr Thr
        515                 520                 525
Ile Tyr Val Ile Ala Leu Lys Asn Asn Gln Lys Ser Glu Pro Leu Ile
    530                 535                 540
Gly Arg Lys Lys Thr Asp Glu Leu Pro Gln Leu Val Thr Leu Pro His
545                 550                 555                 560
Pro Asn Leu His Gly Pro Glu Ile Leu Asp Val Pro Ser Thr
                565                 570
```

<210> SEQ ID NO 8
<211> LENGTH: 1731
<212> TYPE: DNA
<213> ORGANISM: Artificial Sequence
<220> FEATURE:
<223> OTHER INFORMATION: polynucleotide coding fibronectin fragment named CH-296

<400> SEQUENCE: 8

| | | | | | |
|---|---|---|---|---|---|
| atgcccactg | acctgcgatt | caccaacatt | ggtccagaca | ccatgcgtgt | cacctgggct | 60 |
| ccaccccat | ccattgattt | aaccaacttc | ctggtgcgtt | actcacctgt | gaaaatgag | 120 |
| gaagatgttg | cagagttgtc | aatttctcct | tcagacaatg | cagtggtctt | aacaaatctc | 180 |
| ctgcctggta | cagaatatgt | agtgagtgtc | tccagtgtct | acgaacaaca | tgagagcaca | 240 |
| cctcttagag | aagacagaa | aacaggtctt | gattccccaa | ctggcattga | cttttctgat | 300 |
| attactgcca | actcttttac | tgtgcactgg | attgctcctc | gagccaccat | cactggctac | 360 |
| aggatccgcc | atcatcccga | gcacttcagt | gggagacctc | gagaagatcg | gtgccccac | 420 |
| tctcggaatt | ccatcaccct | caccaacctc | actccaggca | cagagtatgt | ggtcagcatc | 480 |
| gttgctctta | atgcagaga | ggaaagtccc | ttattgattg | ccaacaatc | aacagtttct | 540 |
| gatgttccga | gggacctgga | agttgttgct | gcgaccccca | ccagcctact | gatcagctgg | 600 |
| gatgctcctg | ctgtcacagt | gagatattac | aggatcactt | acggagaaac | aggaggaaat | 660 |
| agccctgtcc | aggagttcac | tgtgcctggg | agcaagtcta | cagctaccat | cagcggcctt | 720 |
| aaacctggag | ttgattatac | catcactgtg | tatgctgtca | ctggccgtgg | agacagcccc | 780 |
| gcaagcagca | agccaatttc | cattaattac | cgaacagaaa | ttgacaaacc | atccatggct | 840 |
| attcctgcac | aactgacct | gaagttcact | caggtcacac | cacaagcct | gagcgcccag | 900 |
| tggacaccac | ccaatgttca | gctcactgga | tatcgagtgc | gggtgacccc | caaggagaag | 960 |
| accggaccaa | tgaaagaaat | caaccttgct | cctgacagct | catccgtggt | tgtatcagga | 1020 |
| cttatggtgg | ccaccaaata | tgaagtgagt | gtctatgctc | ttaaggacac | tttgacaagc | 1080 |

```
agaccagctc agggagttgt caccactctg gagaatgtca gcccaccaag aagggctcgt    1140
gtgacagatg ctactgagac caccatcacc attagctgga gaaccaagac tgagacgatc    1200
actggcttcc aagttgatgc cgttccagcc aatggccaga ctccaatcca gagaaccatc    1260
aagccagatg tcagaagcta caccatcaca ggtttacaac caggcactga ctacaagatc    1320
tacctgtaca ccttgaatga caatgctcgg agctcccctg tggtcatcga cgcctccact    1380
gccattgatg caccatccaa cctgcgtttc ctggccacca cacccaattc cttgctggta    1440
tcatggcagc cgccacgtgc caggattacc ggctacatca tcaagtatga aagcctggg    1500 tctcctccca gagaagtggt ccctcggccc cgccctggtg tcacagaggc tactattact    1560
ggcctggaac cgggaaccga atatacaatt tatgtcattg ccctgaagaa taatcagaag    1620
agcgagcccc tgattggaag gaaaaagaca gacgagcttc cccaactggt aacccttcca    1680
caccccaatc ttcatggacc agagatcttg gatgttcctt ccacataata g             1731
```

```
<210> SEQ ID NO 9
<211> LENGTH: 32
<212> TYPE: DNA
<213> ORGANISM: Artificial Sequence
<220> FEATURE:
<223> OTHER INFORMATION: Synthetic primer H296-NcoF

<400> SEQUENCE: 9
gagcggataa ccatggctat tcctgcacca ac                                    32

<210> SEQ ID NO 10
<211> LENGTH: 36
<212> TYPE: DNA
<213> ORGANISM: Artificial Sequence
<220> FEATURE:
<223> OTHER INFORMATION: Synthetic primer H296-HindR

<400> SEQUENCE: 10
gagcggataa aagctttat gtggaaggaa catcca                                 36

<210> SEQ ID NO 11
<211> LENGTH: 34
<212> TYPE: DNA
<213> ORGANISM: Artificial Sequence
<220> FEATURE:
<223> OTHER INFORMATION: Synthetic primer H296-NcoR

<400> SEQUENCE: 11
gattacctac catggctgtg gaaggaacat ccaa                                  34

<210> SEQ ID NO 12
<211> LENGTH: 20
<212> TYPE: DNA
<213> ORGANISM: Artificial Sequence
<220> FEATURE:
<223> OTHER INFORMATION: Synthetic primer NC2-5'UTR

<400> SEQUENCE: 12
gcatatccag tgtagtaagg                                                  20

<210> SEQ ID NO 13
<211> LENGTH: 9
<212> TYPE: PRT
<213> ORGANISM: Artificial Sequence
<220> FEATURE:
<223> OTHER INFORMATION: designed peptide based on matrix-protein
      derived from influenza virus
```

-continued

<400> SEQUENCE: 13

Gly Ile Leu Gly Phe Val Phe Thr Leu
1               5

<210> SEQ ID NO 14
<211> LENGTH: 35
<212> TYPE: DNA
<213> ORGANISM: Artificial Sequence
<220> FEATURE:
<223> OTHER INFORMATION: Synthetic primer H296-NdeF

<400> SEQUENCE: 14
aacagaccca tatggctatt cctgcaccaa ctgac                                35

<210> SEQ ID NO 15
<211> LENGTH: 27
<212> TYPE: DNA
<213> ORGANISM: Artificial Sequence
<220> FEATURE:
<223> OTHER INFORMATION: Synthetic primer H296-NdeR

<400> SEQUENCE: 15
aagcatatgt gtggaaggaa catccaa                                        27

<210> SEQ ID NO 16
<211> LENGTH: 909
<212> TYPE: PRT
<213> ORGANISM: Artificial Sequence
<220> FEATURE:
<223> OTHER INFORMATION: fibronectin fragment named H296-H296-H296-HT

<400> SEQUENCE: 16

Met Asn His Lys Val His His His His His His Ile Glu Gly Arg His
1               5                   10                  15

Met Ala Ile Pro Ala Pro Thr Asp Leu Lys Phe Thr Gln Val Thr Pro
                20                  25                  30

Thr Ser Leu Ser Ala Gln Trp Thr Pro Pro Asn Val Gln Leu Thr Gly
            35                  40                  45

Tyr Arg Val Arg Val Thr Pro Lys Glu Lys Thr Gly Pro Met Lys Glu
        50                  55                  60

Ile Asn Leu Ala Pro Asp Ser Ser Val Val Val Ser Gly Leu Met
65                  70                  75                  80

Val Ala Thr Lys Tyr Glu Val Ser Val Tyr Ala Leu Lys Asp Thr Leu
                85                  90                  95

Thr Ser Arg Pro Ala Gln Gly Val Val Thr Thr Leu Glu Asn Val Ser
            100                 105                 110

Pro Pro Arg Arg Ala Arg Val Thr Asp Ala Thr Glu Thr Thr Ile Thr
        115                 120                 125

Ile Ser Trp Arg Thr Lys Thr Glu Thr Ile Thr Gly Phe Gln Val Asp
    130                 135                 140

Ala Val Pro Ala Asn Gly Gln Thr Pro Ile Gln Arg Thr Ile Lys Pro
145                 150                 155                 160

Asp Val Arg Ser Tyr Thr Ile Thr Gly Leu Gln Pro Gly Thr Asp Tyr
                165                 170                 175

Lys Ile Tyr Leu Tyr Thr Leu Asn Asp Asn Ala Arg Ser Ser Pro Val
            180                 185                 190

Val Ile Asp Ala Ser Thr Ala Ile Asp Ala Pro Ser Asn Leu Arg Phe
        195                 200                 205

Leu Ala Thr Thr Pro Asn Ser Leu Leu Val Ser Trp Gln Pro Pro Arg
    210                 215                 220

```
Ala Arg Ile Thr Gly Tyr Ile Lys Tyr Glu Lys Pro Gly Ser Pro
225                 230                 235                 240

Pro Arg Glu Val Val Pro Arg Pro Gly Val Thr Glu Ala Thr
            245                 250                 255

Ile Thr Gly Leu Glu Pro Gly Thr Glu Tyr Thr Ile Tyr Val Ile Ala
                260                 265                 270

Leu Lys Asn Asn Gln Lys Ser Glu Pro Leu Ile Gly Arg Lys Lys Thr
                275                 280                 285

Asp Glu Leu Pro Gln Leu Val Thr Leu Pro His Pro Asn Leu His Gly
                290                 295                 300

Pro Glu Ile Leu Asp Val Pro Ser Thr His Met Ala Ile Pro Ala Pro
305                 310                 315                 320

Thr Asp Leu Lys Phe Thr Gln Val Thr Pro Thr Ser Leu Ser Ala Gln
                325                 330                 335

Trp Thr Pro Pro Asn Val Gln Leu Thr Gly Tyr Arg Val Arg Val Thr
                340                 345                 350

Pro Lys Glu Lys Thr Gly Pro Met Lys Glu Ile Asn Leu Ala Pro Asp
                355                 360                 365

Ser Ser Ser Val Val Val Ser Gly Leu Met Val Ala Thr Lys Tyr Glu
                370                 375                 380

Val Ser Val Tyr Ala Leu Lys Asp Thr Leu Thr Ser Arg Pro Ala Gln
385                 390                 395                 400

Gly Val Val Thr Thr Leu Glu Asn Val Ser Pro Pro Arg Arg Ala Arg
                405                 410                 415

Val Thr Asp Ala Thr Glu Thr Thr Ile Thr Ile Ser Trp Arg Thr Lys
                420                 425                 430

Thr Glu Thr Ile Thr Gly Phe Gln Val Asp Ala Val Pro Ala Asn Gly
                435                 440                 445

Gln Thr Pro Ile Gln Arg Thr Ile Lys Pro Asp Val Arg Ser Tyr Thr
                450                 455                 460

Ile Thr Gly Leu Gln Pro Gly Thr Asp Tyr Lys Ile Tyr Leu Tyr Thr
465                 470                 475                 480

Leu Asn Asp Asn Ala Arg Ser Ser Pro Val Val Ile Asp Ala Ser Thr
                485                 490                 495

Ala Ile Asp Ala Pro Ser Asn Leu Arg Phe Leu Ala Thr Thr Pro Asn
                500                 505                 510

Ser Leu Leu Val Ser Trp Gln Pro Pro Arg Ala Arg Ile Thr Gly Tyr
                515                 520                 525

Ile Ile Lys Tyr Glu Lys Pro Gly Ser Pro Pro Arg Glu Val Val Pro
530                 535                 540

Arg Pro Arg Pro Gly Val Thr Glu Ala Thr Ile Thr Gly Leu Glu Pro
545                 550                 555                 560

Gly Thr Glu Tyr Thr Ile Tyr Val Ile Ala Leu Lys Asn Asn Gln Lys
                565                 570                 575

Ser Glu Pro Leu Ile Gly Arg Lys Lys Thr Asp Glu Leu Pro Gln Leu
                580                 585                 590

Val Thr Leu Pro His Pro Asn Leu His Gly Pro Glu Ile Leu Asp Val
                595                 600                 605

Pro Ser Thr His Met Ala Ile Pro Ala Pro Thr Asp Leu Lys Phe Thr
                610                 615                 620

Gln Val Thr Pro Thr Ser Leu Ser Ala Gln Trp Thr Pro Pro Asn Val
625                 630                 635                 640

Gln Leu Thr Gly Tyr Arg Val Arg Val Thr Pro Lys Glu Lys Thr Gly
```

645                 650                 655
Pro Met Lys Glu Ile Asn Leu Ala Pro Asp Ser Ser Val Val
        660                 665                 670

Ser Gly Leu Met Val Ala Thr Lys Tyr Glu Val Ser Val Tyr Ala Leu
        675                 680                 685

Lys Asp Thr Leu Thr Ser Arg Pro Ala Gln Gly Val Val Thr Thr Leu
        690                 695                 700

Glu Asn Val Ser Pro Pro Arg Arg Ala Arg Val Thr Asp Ala Thr Glu
705                 710                 715                 720

Thr Thr Ile Thr Ile Ser Trp Arg Thr Lys Thr Glu Thr Ile Thr Gly
                725                 730                 735

Phe Gln Val Asp Ala Val Pro Ala Asn Gly Gln Thr Pro Ile Gln Arg
            740                 745                 750

Thr Ile Lys Pro Asp Val Arg Ser Tyr Thr Ile Thr Gly Leu Gln Pro
        755                 760                 765

Gly Thr Asp Tyr Lys Ile Tyr Leu Tyr Thr Leu Asn Asp Asn Ala Arg
    770                 775                 780

Ser Ser Pro Val Val Ile Asp Ala Ser Thr Ala Ile Asp Ala Pro Ser
785                 790                 795                 800

Asn Leu Arg Phe Leu Ala Thr Thr Pro Asn Ser Leu Leu Val Ser Trp
                805                 810                 815

Gln Pro Pro Arg Ala Arg Ile Thr Gly Tyr Ile Ile Lys Tyr Glu Lys
            820                 825                 830

Pro Gly Ser Pro Pro Arg Glu Val Val Pro Arg Pro Arg Pro Gly Val
        835                 840                 845

Thr Glu Ala Thr Ile Thr Gly Leu Glu Pro Gly Thr Glu Tyr Thr Ile
    850                 855                 860

Tyr Val Ile Ala Leu Lys Asn Asn Gln Lys Ser Glu Pro Leu Ile Gly
865                 870                 875                 880

Arg Lys Lys Thr Asp Glu Leu Pro Gln Leu Val Thr Leu Pro His Pro
                885                 890                 895

Asn Leu His Gly Pro Glu Ile Leu Asp Val Pro Ser Thr
            900                 905

<210> SEQ ID NO 17
<211> LENGTH: 2730
<212> TYPE: DNA
<213> ORGANISM: Artificial Sequence
<220> FEATURE:
<223> OTHER INFORMATION: polynucleotide coding fibronectin fragment
      named H296-H296-H296-HT

<400> SEQUENCE: 17
atgaatcaca aagtgcatca tcatcatcat catatcgaag gtaggcatat ggctattcct      60
gcaccaactg acctgaagtt cactcaggtc acacccacaa gcctgagcgc ccagtggaca     120
ccacccaatg ttcagctcac tggatatcga gtgcgggtga cccccaagga agagaccgga     180
ccaatgaaag aaatcaacct tgctcctgac agctcatccg tggttgtatc aggacttatg     240
gtggccacca atatgaagt gagtgtctat gctcttaagg acactttgac aagcagacca     300
gctcagggag ttgtcaccac tctggagaat gtcagcccac caagaagggc tcgtgtgaca     360
gatgctactg agaccaccat caccattagc tggagaacca agactgagac gatcactggc     420
ttccaagttg atgccgttcc agccaatggc agactccaa tccagagaac catcaagcca     480
gatgtcagaa gctacaccat cacaggttta caaccaggc tgactacaa gatctacctg     540 tacaccttga tgacaatgc tcggagctcc cctgtggtca tcgacgcctc cactgccatt     600

```
gatgcaccat ccaacctgcg tttcctggcc accacaccca attccttgct ggtatcatgg    660
cagccgccac gtgccaggat taccggctac atcatcaagt atgagaagcc tgggtctcct    720
cccagagaag tggtccctcg ccccgccct ggtgtcacag aggctactat tactggcctg     780
gaaccgggaa ccgaatatac aatttatgtc attgccctga gaataatca gaagagcgag     840 cccctgattg aaggaaaaaa gacagacgag cttccccaac tggtaaccct tccacacccc    900
aatcttcatg gaccagagat cttggatgtt ccttccacac atatggctat tcctgcacca    960
actgacctga gttcactca ggtcacaccc acaagcctga cgcccagtg gacaccaccc      1020 aatgttcagc tcactggata tcgagtgcgg gtgacccca aggagaagac cggaccaatg     1080
aaagaaatca accttgctcc tgacagctca tccgtggttg tatcaggact tatggtggcc    1140
accaaatatg aagtgagtgt ctatgctctt aaggacactt tgacaagcag accagctcag    1200
ggagttgtca ccactctgga gaatgtcagc ccaccaagaa gggctcgtgt gacagatgct    1260
actgagacca ccatcaccat tagctggaga accaagactg agacgatcac tggcttccaa    1320
gttgatgccg ttccagccaa tggccagact ccaatccaga gaaccatcaa gccagatgtc    1380
agaagctaca ccatcacagg tttacaacca ggcactgact acaagatcta cctgtacacc    1440
ttgaatgaca atgctcggag ctcccctgtg gtcatcgacg cctccactgc cattgatgca    1500
ccatccaacc tgcgtttcct ggccaccaca cccaattcct tgctggtatc atggcagccg    1560
ccacgtgcca ggattaccgg ctacatcatc aagtatgaga agcctgggtc tcctcccaga    1620
gaagtggtcc ctcggcccg ccctggtgtc acagaggcta ctattactgg cctggaaccg     1680
ggaaccgaat atacaattta tgtcattgcc ctgaagaata tcagaagag cgagcccctg     1740 attggaagga aaaagacaga cgagcttccc caactggtaa cccttccaca ccccaatctt    1800
catggaccag agatcttgga tgttccttcc acacatatgg ctattcctgc accaactgac    1860
ctgaagttca ctcaggtcac acccacaagc tgagcgccc agtggacacc cccaatgtt     1920 cagctcactg gatatcgagt gcgggtgacc cccaaggaga gaccggacc aatgaaagaa    1980 atcaaccttg ctcctgacag ctcatccgtg gttgtatcag gacttatggt ggccaccaaa    2040
tatgaagtga gtgtctatgc tcttaaggac actttgacaa gcagaccagc tcagggagtt    2100
gtcaccactc tggagaatgt cagcccacca agaagggctc gtgtgacaga tgctactgag    2160
accaccatca ccattagctg gagaaccaag actgagacga tcactggctt ccaagttgat    2220
gccgttccag ccaatggcca gactccaatc cagagaacca tcaagccaga tgtcagaagc    2280
tacaccatca caggtttaca accaggcact gactacaaga tctacctgta cacccttgaat   2340 gacaatgctc ggagctcccc tgtggtcatc gacgcctcca ctgccattga tgcaccatcc    2400
aacctgcgtt tcctggccac cacacccaat tccttgctgg tatcatggca gccgccacgt    2460
gccaggatta ccggctacat catcaagtat gagaagcctg gtctcctcc cagagaagtg    2520 gtccctcggc cccgcctgg tgtcacagag gctactatta ctggcctgga accgggaacc    2580
gaatatacaa tttatgtcat tgccctgaag aataatcaga gagcgagcc cctgattgga    2640 aggaaaaaga cagacgagct tccccaactg gtaacccttc cacacccaa tcttcatgga    2700 ccagagatct tggatgttcc ttccacataa                                     2730
```

<210> SEQ ID NO 18
<211> LENGTH: 34
<212> TYPE: DNA
<213> ORGANISM: Artificial Sequence
<220> FEATURE:
<223> OTHER INFORMATION: Synthetic primer CH296-NdeF

<400> SEQUENCE: 18
aacagaccca tatgcccact gacctgcgat tcac                                   34

<210> SEQ ID NO 19
<211> LENGTH: 1167
<212> TYPE: PRT
<213> ORGANISM: Artificial Sequence
<220> FEATURE:
<223> OTHER INFORMATION: fibronectin fragment named CH296-CH296-HT

<400> SEQUENCE: 19

```
Met Asn His Lys Val His His His His His His Ile Glu Gly Arg His
1               5                   10                  15

Met Pro Thr Asp Leu Arg Phe Thr Asn Ile Gly Pro Asp Thr Met Arg
            20                  25                  30

Val Thr Trp Ala Pro Pro Ser Ile Asp Leu Thr Asn Phe Leu Val
        35                  40                  45

Arg Tyr Ser Pro Val Lys Asn Glu Glu Asp Val Ala Glu Leu Ser Ile
    50                  55                  60

Ser Pro Ser Asp Asn Ala Val Val Leu Thr Asn Leu Leu Pro Gly Thr
65                  70                  75                  80

Glu Tyr Val Val Ser Val Ser Ser Val Tyr Glu Gln His Glu Ser Thr
                85                  90                  95

Pro Leu Arg Gly Arg Gln Lys Thr Gly Leu Asp Ser Pro Thr Gly Ile
            100                 105                 110

Asp Phe Ser Asp Ile Thr Ala Asn Ser Phe Thr Val His Trp Ile Ala
        115                 120                 125

Pro Arg Ala Thr Ile Thr Gly Tyr Arg Ile Arg His His Pro Glu His
    130                 135                 140

Phe Ser Gly Arg Pro Arg Glu Asp Arg Val Pro His Ser Arg Asn Ser
145                 150                 155                 160

Ile Thr Leu Thr Asn Leu Thr Pro Gly Thr Glu Tyr Val Val Ser Ile
                165                 170                 175

Val Ala Leu Asn Gly Arg Glu Glu Ser Pro Leu Leu Ile Gly Gln Gln
            180                 185                 190

Ser Thr Val Ser Asp Val Pro Arg Asp Leu Glu Val Val Ala Ala Thr
        195                 200                 205

Pro Thr Ser Leu Leu Ile Ser Trp Asp Ala Pro Ala Val Thr Val Arg
    210                 215                 220

Tyr Tyr Arg Ile Thr Tyr Gly Glu Thr Gly Gly Asn Ser Pro Val Gln
225                 230                 235                 240

Glu Phe Thr Val Pro Gly Ser Lys Ser Thr Ala Thr Ile Ser Gly Leu
                245                 250                 255

Lys Pro Gly Val Asp Tyr Thr Ile Thr Val Tyr Ala Val Thr Gly Arg
            260                 265                 270

Gly Asp Ser Pro Ala Ser Ser Lys Pro Ile Ser Ile Asn Tyr Arg Thr
        275                 280                 285

Glu Ile Asp Lys Pro Ser Met Ala Ile Pro Ala Pro Thr Asp Leu Lys
    290                 295                 300

Phe Thr Gln Val Thr Pro Thr Ser Leu Ser Ala Gln Trp Thr Pro Pro
305                 310                 315                 320

Asn Val Gln Leu Thr Gly Tyr Arg Val Arg Val Thr Pro Lys Glu Lys
                325                 330                 335

Thr Gly Pro Met Lys Glu Ile Asn Leu Ala Pro Asp Ser Ser Ser Val
            340                 345                 350
```

```
Val Val Ser Gly Leu Met Val Ala Thr Lys Tyr Glu Val Ser Val Tyr
            355                 360                 365

Ala Leu Lys Asp Thr Leu Thr Ser Arg Pro Ala Gln Gly Val Val Thr
            370                 375                 380

Thr Leu Glu Asn Val Ser Pro Pro Arg Arg Ala Arg Val Thr Asp Ala
385                 390                 395                 400

Thr Glu Thr Thr Ile Thr Ile Ser Trp Arg Thr Lys Thr Glu Thr Ile
                    405                 410                 415

Thr Gly Phe Gln Val Asp Ala Val Pro Ala Asn Gly Gln Thr Pro Ile
                420                 425                 430

Gln Arg Thr Ile Lys Pro Asp Val Arg Ser Tyr Thr Ile Thr Gly Leu
            435                 440                 445

Gln Pro Gly Thr Asp Tyr Lys Ile Tyr Leu Tyr Thr Leu Asn Asp Asn
            450                 455                 460

Ala Arg Ser Ser Pro Val Val Ile Asp Ala Ser Thr Ala Ile Asp Ala
465                 470                 475                 480

Pro Ser Asn Leu Arg Phe Leu Ala Thr Thr Pro Asn Ser Leu Leu Val
                    485                 490                 495

Ser Trp Gln Pro Pro Arg Ala Arg Ile Thr Gly Tyr Ile Ile Lys Tyr
                500                 505                 510

Glu Lys Pro Gly Ser Pro Pro Arg Glu Val Val Pro Arg Pro Arg Pro
            515                 520                 525

Gly Val Thr Glu Ala Thr Ile Thr Gly Leu Glu Pro Gly Thr Glu Tyr
            530                 535                 540

Thr Ile Tyr Val Ile Ala Leu Lys Asn Asn Gln Lys Ser Glu Pro Leu
545                 550                 555                 560

Ile Gly Arg Lys Lys Thr Asp Glu Leu Pro Gln Leu Val Thr Leu Pro
                    565                 570                 575

His Pro Asn Leu His Gly Pro Glu Ile Leu Asp Val Pro Ser Thr His
                580                 585                 590

Met Pro Thr Asp Leu Arg Phe Thr Asn Ile Gly Pro Asp Thr Met Arg
            595                 600                 605

Val Thr Trp Ala Pro Pro Ser Ile Asp Leu Thr Asn Phe Leu Val
            610                 615                 620

Arg Tyr Ser Pro Val Lys Asn Glu Glu Asp Val Ala Glu Leu Ser Ile
625                 630                 635                 640

Ser Pro Ser Asp Asn Ala Val Val Leu Thr Asn Leu Leu Pro Gly Thr
                    645                 650                 655

Glu Tyr Val Val Ser Val Ser Ser Val Tyr Glu Gln His Glu Ser Thr
                660                 665                 670

Pro Leu Arg Gly Arg Gln Lys Thr Gly Leu Asp Ser Pro Thr Gly Ile
            675                 680                 685

Asp Phe Ser Asp Ile Thr Ala Asn Ser Phe Thr Val His Trp Ile Ala
            690                 695                 700

Pro Arg Ala Thr Ile Thr Gly Tyr Arg Ile Arg His His Pro Glu His
705                 710                 715                 720

Phe Ser Gly Arg Pro Arg Glu Asp Arg Val Pro His Ser Arg Asn Ser
                    725                 730                 735

Ile Thr Leu Thr Asn Leu Thr Pro Gly Thr Glu Tyr Val Val Ser Ile
                740                 745                 750

Val Ala Leu Asn Gly Arg Glu Glu Ser Pro Leu Leu Ile Gly Gln Gln
            755                 760                 765

Ser Thr Val Ser Asp Val Pro Arg Asp Leu Glu Val Val Ala Ala Thr
```

```
                770             775             780
Pro Thr Ser Leu Leu Ile Ser Trp Asp Ala Pro Ala Val Thr Val Arg
785                 790                 795                 800

Tyr Tyr Arg Ile Thr Tyr Gly Glu Thr Gly Asn Ser Pro Val Gln
                805                 810                 815

Glu Phe Thr Val Pro Gly Ser Lys Ser Thr Ala Thr Ile Ser Gly Leu
                820                 825                 830

Lys Pro Gly Val Asp Tyr Thr Ile Thr Val Tyr Ala Val Thr Gly Arg
                835                 840                 845

Gly Asp Ser Pro Ala Ser Ser Lys Pro Ile Ser Ile Asn Tyr Arg Thr
850                 855                 860

Glu Ile Asp Lys Pro Ser Met Ala Ile Pro Ala Pro Thr Asp Leu Lys
865                 870                 875                 880

Phe Thr Gln Val Thr Pro Thr Ser Leu Ser Ala Gln Trp Thr Pro Pro
                885                 890                 895

Asn Val Gln Leu Thr Gly Tyr Arg Val Arg Val Thr Pro Lys Glu Lys
                900                 905                 910

Thr Gly Pro Met Lys Glu Ile Asn Leu Ala Pro Asp Ser Ser Ser Val
                915                 920                 925

Val Val Ser Gly Leu Met Val Ala Thr Lys Tyr Glu Val Ser Val Tyr
930                 935                 940

Ala Leu Lys Asp Thr Leu Thr Ser Arg Pro Ala Gln Gly Val Val Thr
945                 950                 955                 960

Thr Leu Glu Asn Val Ser Pro Pro Arg Arg Ala Arg Val Thr Asp Ala
                965                 970                 975

Thr Glu Thr Thr Ile Thr Ile Ser Trp Arg Thr Lys Thr Glu Thr Ile
                980                 985                 990

Thr Gly Phe Gln Val Asp Ala Val  Pro Ala Asn Gly Gln  Thr Pro Ile
                995                 1000                1005

Gln Arg  Thr Ile Lys Pro Asp  Val Arg Ser Tyr Thr  Ile Thr Gly
    1010                1015                1020

Leu Gln  Pro Gly Thr Asp Tyr  Lys Ile Tyr Leu Tyr  Thr Leu Asn
    1025                1030                1035

Asp Asn  Ala Arg Ser Ser Pro  Val Val Ile Asp Ala  Ser Thr Ala
    1040                1045                1050

Ile Asp  Ala Pro Ser Asn Leu  Arg Phe Leu Ala Thr  Thr Pro Asn
    1055                1060                1065

Ser Leu  Leu Val Ser Trp Gln  Pro Pro Arg Ala Arg  Ile Thr Gly
    1070                1075                1080

Tyr Ile  Ile Lys Tyr Glu Lys  Pro Gly Ser Pro Arg  Glu Val
    1085                1090                1095

Val Pro  Arg Pro Arg Pro Gly  Val Thr Glu Ala Thr  Ile Thr Gly
    1100                1105                1110

Leu Glu  Pro Gly Thr Glu Tyr  Thr Ile Tyr Val Ile  Ala Leu Lys
    1115                1120                1125

Asn Asn  Gln Lys Ser Glu Pro  Leu Ile Gly Arg Lys  Lys Thr Asp
    1130                1135                1140

Glu Leu  Pro Gln Leu Val Thr  Leu Pro His Pro Asn  Leu His Gly
    1145                1150                1155

Pro Glu  Ile Leu Asp Val Pro  Ser Thr
    1160                1165

<210> SEQ ID NO 20
<211> LENGTH: 3504
```

```
<212> TYPE: DNA
<213> ORGANISM: Artificial Sequence
<220> FEATURE:
<223> OTHER INFORMATION: polynucleotide coding fibronectin fragment
      named CH296-CH296-HT

<400> SEQUENCE: 20
atgaatcaca aagtgcatca tcatcatcat catatcgaag gtaggcatat gcccactgac     60
ctgcgattca ccaacattgg tccagacacc atgcgtgtca cctgggctcc accccatcc    120
attgatttaa ccaacttcct ggtgcgttac tcacctgtga aaatgaggaa agatgttgca    180
gagttgtcaa tttctccttc agacaatgca gtggtcttaa caaatctcct gcctggtaca    240
gaatatgtag tgagtgtctc cagtgtctac gaacaacatg agagcacacc tcttagagga    300
agacagaaaa caggtcttga ttccccaact ggcattgact tttctgatat tactgccaac    360
tcttttactg tgcactggat tgctcctcga gccaccatca ctggctacag gatccgccat    420
catcccgagc acttcagtgg agacctcgaa gatcgggtgc cccactctcg gaattcc      480
atcaccctca ccaacctcac tccaggcaca gagtatgtgg tcagcatcgt tgctcttaat    540
ggcagagagg aaagtccctt attgattggc aacaatcaaa cagtttctga tgttccgagg    600
gacctggaag ttgttgctgc gaccccacc agcctactga tcagctggga tgctcctgct    660
gtcacagtga gatattacag gatcacttac ggagaaacag gaggaaatag ccctgtccag    720
gagttcactg tgcctgggag caagtctaca gctaccatca gcggccttaa acctggagtt    780
gattatacca tcactgtgta tgctgtcact ggccgtggag acagcccgc aagcagcaag    840
ccaatttcca ttaattaccg aacagaaatt gacaaaccat ccatggctat tcctgcacca    900
actgacctga gttcactca ggtcacaccc acaagcctga cgcccagtg acaccaccc      960
aatgttcagc tcactggata tcgagtgcgg gtgacccca aggagaagac cggaccaatg    1020
aaagaaatca accttgctcc tgacagctca tccgtggttg tatcaggact tatggtggcc    1080
accaaatatg aagtgagtgt ctatgctctt aaggacactt tgacaagcag accagctcag    1140
ggagttgtca ccactctgga aatgtcagc ccaccaagaa gggctcgtgt gacagatgct    1200
actgagacca ccatcaccat tagctggaga accaagactg agacgatcac tggcttccaa    1260
gttgatgccg ttccagccaa tggccagact ccaatccaga gaccatcaa gccagatgtc    1320
agaagctaca ccatcacagg tttacaacca ggcactgact acaagatcta cctgtacacc    1380
ttgaatgaca atgctcggag ctccctgtg gtcatcgacg cctccactgc cattgatgca    1440
ccatccaacc tgcgtttcct ggccaccaca cccaattcct tgctggtatc atggcagccg    1500
ccacgtgcca ggattaccgg ctacatcatc aagtatgaga agcctgggtc tcctcccaga    1560
gaagtggtcc ctcggccccg ccctggtgtc acagaggcta ctattactgg cctgaaccg    1620
ggaaccgaat atacaattta tgtcattgcc ctgaagaata tcagaagag cgagcccctg    1680
attggaagga aaagacaga cgagcttccc caactggtaa cccttccaca ccccaatctt    1740
catggaccag agatcttgga tgttccttcc acacatatgc ccactgacct gcgattcacc    1800
aacattggtc cagacaccat gcgtgtcacc tgggctccac cccatccat tgatttaacc    1860
aacttcctgg tgcgttactc acctgtgaaa aatgaggaag atgttgcaga gttgtcaatt    1920
tctccttcag acaatgcagt ggtcttaaca aatctcctgc ctggtacaga atatgtagtg    1980
agtgtctcca gtgtctacga acaacatgag agcacacctc ttagaggaag acagaaaaca    2040
ggtcttgatt ccccaactgg cattgacttt tctgatatta ctgccaactc ttttactgtg    2100
cactggattg ctcctcgagc caccatcact ggctacagga tccgccatca tcccgagcac    2160
```

-continued

```
ttcagtggga gacctcgaga agatcgggtg ccccactctc ggaattccat caccctcacc    2220
aacctcactc caggcacaga gtatgtggtc agcatcgttg ctcttaatgg cagagaggaa    2280
agtcccttat tgattggcca acaatcaaca gtttctgatg ttccgaggga cctggaagtt    2340
gttgctgcga cccccaccag cctactgatc agctgggatg ctcctgctgt cacagtgaga    2400
tattacagga tcacttacgg agaaacagga ggaaatagcc ctgtccagga gttcactgtg    2460
cctgggagca gtctacagc taccatcagc ggccttaaac ctggagttga ttataccatc    2520
actgtgtatg ctgtcactgg ccgtggagac agccccgcaa gcagcaagcc aatttccatt    2580
aattaccgaa cagaaattga caaaccatcc atggctattc ctgcaccaac tgacctgaag    2640
ttcactcagg tcacacccac aagcctgagc gcccagtgga caccaccaa tgttcagctc    2700 actggatatc gagtgcgggt gaccccaag gagaagaccg gaccaatgaa agaaatcaac    2760
cttgctcctg acagctcatc cgtggttgta tcaggactta tggtggccac caaatatgaa    2820
gtgagtgtct atgctcttaa ggacactttg acaagcagac cagctcaggg agttgtcacc    2880
actctggaga atgtcagccc accaagaagg gctcgtgtga cagatgctac tgagaccacc    2940
atcaccatta gctggagaac caagactgag acgatcactg gcttccaagt tgatgccgtt    3000
ccagccaatg ccagactcc aatccagaga accatcaagc cagatgtcag aagctacacc    3060
atcacaggtt tacaaccagg cactgactac aagatctacc tgtacacctt gaatgacaat    3120
gctcggagct cccctgtggt catcgacgcc tccactgcca ttgatgcacc atccaacctg    3180
cgtttcctgg ccaccacacc caattccttg ctggtatcat ggcagccgcc acgtgccagg    3240
attaccggct acatcatcaa gtatgagaag cctgggtctc tcccagaga gtggtccct    3300 cggccccgcc ctggtgtcac agaggctact attactggcc tggaaccggg aaccgaatat    3360
acaatttatg tcattgccct gaagaataat cagaagagcg agcccctgat tggaaggaaa    3420
aagacagacg agcttcccca actggtaacc cttccacacc ccaatcttca tggaccagag    3480
atcttggatg ttccttccac ataa                                           3504
```

<210> SEQ ID NO 21
<211> LENGTH: 35
<212> TYPE: DNA
<213> ORGANISM: Artificial Sequence
<220> FEATURE:
<223> OTHER INFORMATION: Synthetic primer H105-NdeF

<400> SEQUENCE: 21
aacagaccca tatggccatt gatgcaccat ccaac                              35

<210> SEQ ID NO 22
<211> LENGTH: 249
<212> TYPE: PRT
<213> ORGANISM: Artificial Sequence
<220> FEATURE:
<223> OTHER INFORMATION: fibronectin fragment named H105-H105-HT

<400> SEQUENCE: 22

Met Asn His Lys Val His His His His His His Ile Glu Gly Arg His
1               5                   10                  15

Met Ala Ile Asp Ala Pro Ser Asn Leu Arg Phe Leu Ala Thr Thr Pro
            20                  25                  30

Asn Ser Leu Leu Val Ser Trp Gln Pro Pro Arg Ala Arg Ile Thr Gly
        35                  40                  45

Tyr Ile Ile Lys Tyr Glu Lys Pro Gly Ser Pro Arg Glu Val Val
    50                  55                  60

```
Pro Arg Pro Arg Pro Gly Val Thr Glu Ala Thr Ile Thr Gly Leu Glu
 65                  70                  75                  80
Pro Gly Thr Glu Tyr Thr Ile Tyr Val Ile Ala Leu Lys Asn Asn Gln
                 85                  90                  95
Lys Ser Glu Pro Leu Ile Gly Arg Lys Thr Asp Glu Leu Pro Gln
            100                 105                 110
Leu Val Thr Leu Pro His Pro Asn Leu His Gly Pro Glu Ile Leu Asp
            115                 120                 125
Val Pro Ser Thr His Met Ala Ile Asp Ala Pro Ser Asn Leu Arg Phe
        130                 135                 140
Leu Ala Thr Thr Pro Asn Ser Leu Leu Val Ser Trp Gln Pro Pro Arg
145                 150                 155                 160
Ala Arg Ile Thr Gly Tyr Ile Ile Lys Tyr Glu Lys Pro Gly Ser Pro
                165                 170                 175
Pro Arg Glu Val Val Pro Arg Pro Arg Pro Gly Val Thr Glu Ala Thr
            180                 185                 190
Ile Thr Gly Leu Glu Pro Gly Thr Glu Tyr Thr Ile Tyr Val Ile Ala
            195                 200                 205
Leu Lys Asn Asn Gln Lys Ser Glu Pro Leu Ile Gly Arg Lys Lys Thr
        210                 215                 220
Asp Glu Leu Pro Gln Leu Val Thr Leu Pro His Pro Asn Leu His Gly
225                 230                 235                 240
Pro Glu Ile Leu Asp Val Pro Ser Thr
                245

<210> SEQ ID NO 23
<211> LENGTH: 753
<212> TYPE: DNA
<213> ORGANISM: Artificial Sequence
<220> FEATURE:
<223> OTHER INFORMATION: polynucleotide coding fibronectin fragment
      named H105-H105-HT

<400> SEQUENCE: 23
atgaatcaca aagtgcatca tcatcatcat catatcgaag gtaggcatat ggccattgat      60
gcaccatcca acctgcgttt cctggccacc acacccaatt ccttgctggt atcatggcag     120
ccgccacgtg ccaggattac cggctacatc atcaagtatg agaagcctgg gtctcctccc     180
agagaagtgg tccctcggcc ccgccctggt gtcacagagg ctactattac tggcctggaa     240
ccgggaaccg aatatacaat ttatgtcatt gccctgaaga ataatcagaa gagcgagccc     300
ctgattggaa ggaaaaagac agacgagctt ccccaactgg taaccttcc acaccccaat      360 cttcatggac cagagatctt ggatgttcct tccacacata tggccattga tgcaccatcc     420
aacctgcgtt tcctggccac cacacccaat tccttgctgg tatcatggca gccgccacgt     480
gccaggatta ccggctacat catcaagtat gagaagcctg gtctcctcc cagagaagtg     540 gtccctcggc cccgccctgg tgtcacagag gctactatta ctggcctgga accgggaacc     600
gaatatacaa tttatgtcat tgccctgaag aataatcaga gagcgagcc cctgattgga     660 aggaaaaaga cagacgagct tccccaactg gtaaccttc cacaccccaa tcttcatgga     720
ccagagatct tggatgttcc ttccacataa tag                                  753

<210> SEQ ID NO 24
<211> LENGTH: 27
<212> TYPE: DNA
<213> ORGANISM: Artificial Sequence
<220> FEATURE:
<223> OTHER INFORMATION: Synthetic primer CS1-NdeR
```

<400> SEQUENCE: 24
aagcatatgt gtggaaggaa catccaa                                                                27

<210> SEQ ID NO 25
<211> LENGTH: 611
<212> TYPE: PRT
<213> ORGANISM: Artificial Sequence
<220> FEATURE:
<223> OTHER INFORMATION: fibronectin fragment named H296-H296-HT

<400> SEQUENCE: 25

```
Met Asn His Lys Val His His His His His Ile Glu Gly Arg His
1               5                   10                  15

Met Ala Ile Pro Ala Pro Thr Asp Leu Lys Phe Thr Gln Val Thr Pro
            20                  25                  30

Thr Ser Leu Ser Ala Gln Trp Thr Pro Pro Asn Val Gln Leu Thr Gly
        35                  40                  45

Tyr Arg Val Arg Val Thr Pro Lys Glu Lys Thr Gly Pro Met Lys Glu
    50                  55                  60

Ile Asn Leu Ala Pro Asp Ser Ser Val Val Val Ser Gly Leu Met
65                  70                  75                  80

Val Ala Thr Lys Tyr Glu Val Ser Val Tyr Ala Leu Lys Asp Thr Leu
                85                  90                  95

Thr Ser Arg Pro Ala Gln Gly Val Val Thr Thr Leu Glu Asn Val Ser
            100                 105                 110

Pro Pro Arg Arg Ala Arg Val Thr Asp Ala Thr Glu Thr Thr Ile Thr
        115                 120                 125

Ile Ser Trp Arg Thr Lys Thr Glu Thr Ile Thr Gly Phe Gln Val Asp
    130                 135                 140

Ala Val Pro Ala Asn Gly Gln Thr Pro Ile Gln Arg Thr Ile Lys Pro
145                 150                 155                 160

Asp Val Arg Ser Tyr Thr Ile Thr Gly Leu Gln Pro Gly Thr Asp Tyr
                165                 170                 175

Lys Ile Tyr Leu Tyr Thr Leu Asn Asp Asn Ala Arg Ser Ser Pro Val
            180                 185                 190

Val Ile Asp Ala Ser Thr Ala Ile Asp Ala Pro Ser Asn Leu Arg Phe
        195                 200                 205

Leu Ala Thr Thr Pro Asn Ser Leu Leu Val Ser Trp Gln Pro Pro Arg
    210                 215                 220

Ala Arg Ile Thr Gly Tyr Ile Ile Lys Tyr Glu Lys Pro Gly Ser Pro
225                 230                 235                 240

Pro Arg Glu Val Val Pro Arg Pro Arg Pro Gly Val Thr Glu Ala Thr
                245                 250                 255

Ile Thr Gly Leu Glu Pro Gly Thr Glu Tyr Thr Ile Tyr Val Ile Ala
            260                 265                 270

Leu Lys Asn Asn Gln Lys Ser Glu Pro Leu Ile Gly Arg Lys Lys Thr
        275                 280                 285

Asp Glu Leu Pro Gln Leu Val Thr Leu Pro His Pro Asn Leu His Gly
    290                 295                 300

Pro Glu Ile Leu Asp Val Pro Ser Thr His Met Ala Ile Pro Ala Pro
305                 310                 315                 320

Thr Asp Leu Lys Phe Thr Gln Val Thr Pro Thr Ser Leu Ser Ala Gln
                325                 330                 335

Trp Thr Pro Pro Asn Val Gln Leu Thr Gly Tyr Arg Val Arg Val Thr
            340                 345                 350
```

```
Pro Lys Glu Lys Thr Gly Pro Met Lys Glu Ile Asn Leu Ala Pro Asp
        355                 360                 365

Ser Ser Ser Val Val Val Ser Gly Leu Met Val Ala Thr Lys Tyr Glu
    370                 375                 380

Val Ser Val Tyr Ala Leu Lys Asp Thr Leu Thr Ser Arg Pro Ala Gln
385                 390                 395                 400

Gly Val Val Thr Thr Leu Glu Asn Val Ser Pro Pro Arg Arg Ala Arg
                405                 410                 415

Val Thr Asp Ala Thr Glu Thr Thr Ile Thr Ile Ser Trp Arg Thr Lys
            420                 425                 430

Thr Glu Thr Ile Thr Gly Phe Gln Val Asp Ala Val Pro Ala Asn Gly
        435                 440                 445

Gln Thr Pro Ile Gln Arg Thr Ile Lys Pro Asp Val Arg Ser Tyr Thr
    450                 455                 460

Ile Thr Gly Leu Gln Pro Gly Thr Asp Tyr Lys Ile Tyr Leu Tyr Thr
465                 470                 475                 480

Leu Asn Asp Asn Ala Arg Ser Ser Pro Val Val Ile Asp Ala Ser Thr
                485                 490                 495

Ala Ile Asp Ala Pro Ser Asn Leu Arg Phe Leu Ala Thr Thr Pro Asn
            500                 505                 510

Ser Leu Leu Val Ser Trp Gln Pro Pro Arg Ala Arg Ile Thr Gly Tyr
        515                 520                 525

Ile Ile Lys Tyr Glu Lys Pro Gly Ser Pro Pro Arg Glu Val Val Pro
    530                 535                 540

Arg Pro Arg Pro Gly Val Thr Glu Ala Thr Ile Thr Gly Leu Glu Pro
545                 550                 555                 560

Gly Thr Glu Tyr Thr Ile Tyr Val Ile Ala Leu Lys Asn Asn Gln Lys
                565                 570                 575

Ser Glu Pro Leu Ile Gly Arg Lys Lys Thr Asp Glu Leu Pro Gln Leu
            580                 585                 590

Val Thr Leu Pro His Pro Asn Leu His Gly Pro Glu Ile Leu Asp Val
        595                 600                 605

Pro Ser Thr
    610

<210> SEQ ID NO 26
<211> LENGTH: 1836
<212> TYPE: DNA
<213> ORGANISM: Artificial Sequence
<220> FEATURE:
<223> OTHER INFORMATION: polynucleotide coding fibronectin fragment
      named H296-H296-HT

<400> SEQUENCE: 26
atgaatcaca aagtgcatca tcatcatcat catatcgaag gtaggcatat ggctattcct     60
gcaccaactg acctgaagtt cactcaggtc acacccacaa gcctgagcgc ccagtggaca    120
ccacccaatg ttcagctcac tggatatcga gtgcgggtga cccccaagga agagaccgga    180
ccaatgaaag aaatcaacct tgctcctgac agctcatccg tggttgtatc aggacttatg    240
gtggccacca aatatgaagt gagtgtctat gctcttaagg acactttgac aagcagacca    300
gctcagggag ttgtcaccac tctggagaat gtcagcccac caagaagggc tcgtgtgaca    360
gatgctactg agaccaccat caccattagc tggagaacca agactgagac gatcactggc    420
ttccaagttg atgccgttcc agccaatggc cagactccaa tccagagaac catcaagcca    480
gatgtcagaa gctacaccat cacaggttta caaccaggca ctgactacaa gatctacctg    540
```

```
tacaccttga atgacaatgc tcggagctcc cctgtggtca tcgacgcctc cactgccatt    600
gatgcaccat ccaacctgcg tttcctggcc accacaccca attccttgct ggtatcatgg    660
cagccgccac gtgccaggat taccggctac atcatcaagt atgagaagcc tgggtctcct    720
cccagagaag tggtccctcg gccccgccct ggtgtcacag aggctactat tactggcctg    780
gaaccgggaa ccgaatatac aatttatgtc attgccctga gaataatca gaagagcgag     840 cccctgattg aaggaaaaa gacagacgag cttccccaac tggtaaccct tccacacccc    900
aatcttcatg gaccagagat cttggatgtt ccttccacac atatggctat tcctgcacca    960
actgacctga gttcactca ggtcacaccc acaagcctga gcgcccagtg gacaccaccc    1020
aatgttcagc tcactggata tcgagtgcgg gtgaccccca aggagaagac cggaccaatg    1080
aaagaaatca accttgctcc tgacagctca tccgtggttg tatcaggact tatggtggcc    1140
accaaatatg aagtgagtgt ctatgctctt aaggacactt tgacaagcag accagctcag    1200
ggagttgtca ccactctgga aatgtcagc ccaccaagaa gggctcgtgt gacagatgct    1260
actgagacca ccatcaccat tagctggaga accaagactg agacgatcac tggcttccaa    1320
gttgatgccg ttccagccaa tggccagact ccaatccaga gaaccatcaa gccagatgtc    1380
agaagctaca ccatcacagg tttacaacca ggcactgact acaagatcta cctgtacacc    1440
ttgaatgaca atgctcggag ctcccctgtg gtcatcgacg cctccactgc cattgatgca    1500
ccatccaacc tgcgtttcct ggccaccaca cccaattcct tgctggtatc atggcagccg    1560
ccacgtgcca ggattaccgg ctacatcatc aagtatgaga agcctgggtc tcctcccaga    1620
gaagtggtcc ctcggccccg ccctggtgtc acagaggcta ctattactgg cctggaaccg    1680
ggaaccgaat atacaattta tgtcattgcc ctgaagaata atcagaagag cgagcccctg    1740
attggaagga aaagacaga cgagcttccc caactggtaa cccttccaca ccccaatctt    1800
catggaccag atcttgga tgttccttcc acataa                              1836
```

<210> SEQ ID NO 27
<211> LENGTH: 894
<212> TYPE: PRT
<213> ORGANISM: Artificial Sequence
<220> FEATURE:
<223> OTHER INFORMATION: fibronectin fragment named H296-H296-H296

<400> SEQUENCE: 27

```
His Met Ala Ile Pro Ala Pro Thr Asp Leu Lys Phe Thr Gln Val Thr
1               5                   10                  15

Pro Thr Ser Leu Ser Ala Gln Trp Thr Pro Pro Asn Val Gln Leu Thr
            20                  25                  30

Gly Tyr Arg Val Arg Val Thr Pro Lys Glu Lys Thr Gly Pro Met Lys
        35                  40                  45

Glu Ile Asn Leu Ala Pro Asp Ser Ser Ser Val Val Val Ser Gly Leu
    50                  55                  60

Met Val Ala Thr Lys Tyr Glu Val Ser Val Tyr Ala Leu Lys Asp Thr
65                  70                  75                  80

Leu Thr Ser Arg Pro Ala Gln Gly Val Val Thr Thr Leu Glu Asn Val
                85                  90                  95

Ser Pro Pro Arg Arg Ala Arg Val Thr Asp Ala Thr Glu Thr Thr Ile
            100                 105                 110

Thr Ile Ser Trp Arg Thr Lys Thr Glu Thr Ile Thr Gly Phe Gln Val
        115                 120                 125

Asp Ala Val Pro Ala Asn Gly Gln Thr Pro Ile Gln Arg Thr Ile Lys
```

```
                130                 135                 140
Pro Asp Val Arg Ser Tyr Thr Ile Thr Gly Leu Gln Pro Gly Thr Asp
145                 150                 155                 160

Tyr Lys Ile Tyr Leu Tyr Thr Leu Asn Asp Asn Ala Arg Ser Ser Pro
                165                 170                 175

Val Val Ile Asp Ala Ser Thr Ala Ile Asp Ala Pro Ser Asn Leu Arg
            180                 185                 190

Phe Leu Ala Thr Thr Pro Asn Ser Leu Leu Val Ser Trp Gln Pro Pro
        195                 200                 205

Arg Ala Arg Ile Thr Gly Tyr Ile Ile Lys Tyr Glu Lys Pro Gly Ser
210                 215                 220

Pro Pro Arg Glu Val Val Pro Arg Pro Arg Pro Gly Val Thr Glu Ala
225                 230                 235                 240

Thr Ile Thr Gly Leu Glu Pro Gly Thr Glu Tyr Thr Ile Tyr Val Ile
                245                 250                 255

Ala Leu Lys Asn Asn Gln Lys Ser Glu Pro Leu Ile Gly Arg Lys Lys
            260                 265                 270

Thr Asp Glu Leu Pro Gln Leu Val Thr Leu Pro His Pro Asn Leu His
        275                 280                 285

Gly Pro Glu Ile Leu Asp Val Pro Ser Thr His Met Ala Ile Pro Ala
290                 295                 300

Pro Thr Asp Leu Lys Phe Thr Gln Val Thr Pro Thr Ser Leu Ser Ala
305                 310                 315                 320

Gln Trp Thr Pro Pro Asn Val Gln Leu Thr Gly Tyr Arg Val Arg Val
                325                 330                 335

Thr Pro Lys Glu Lys Thr Gly Pro Met Lys Glu Ile Asn Leu Ala Pro
            340                 345                 350

Asp Ser Ser Ser Val Val Val Ser Gly Leu Met Val Ala Thr Lys Tyr
        355                 360                 365

Glu Val Ser Val Tyr Ala Leu Lys Asp Thr Leu Thr Ser Arg Pro Ala
370                 375                 380

Gln Gly Val Val Thr Thr Leu Glu Asn Val Ser Pro Pro Arg Arg Ala
385                 390                 395                 400

Arg Val Thr Asp Ala Thr Glu Thr Thr Ile Thr Ile Ser Trp Arg Thr
                405                 410                 415

Lys Thr Glu Thr Ile Thr Gly Phe Gln Val Asp Ala Val Pro Ala Asn
            420                 425                 430

Gly Gln Thr Pro Ile Gln Arg Thr Ile Lys Pro Asp Val Arg Ser Tyr
        435                 440                 445

Thr Ile Thr Gly Leu Gln Pro Gly Thr Asp Tyr Lys Ile Tyr Leu Tyr
450                 455                 460

Thr Leu Asn Asp Asn Ala Arg Ser Ser Pro Val Val Ile Asp Ala Ser
465                 470                 475                 480

Thr Ala Ile Asp Ala Pro Ser Asn Leu Arg Phe Leu Ala Thr Thr Pro
                485                 490                 495

Asn Ser Leu Leu Val Ser Trp Gln Pro Pro Arg Ala Arg Ile Thr Gly
            500                 505                 510

Tyr Ile Ile Lys Tyr Glu Lys Pro Gly Ser Pro Pro Arg Glu Val Val
        515                 520                 525

Pro Arg Pro Arg Pro Gly Val Thr Glu Ala Thr Ile Thr Gly Leu Glu
530                 535                 540

Pro Gly Thr Glu Tyr Thr Ile Tyr Val Ile Ala Leu Lys Asn Asn Gln
545                 550                 555                 560
```

-continued

| | | | | | | | | | | | |
|---|---|---|---|---|---|---|---|---|---|---|---|
|Lys|Ser|Glu|Pro|Leu|Ile|Gly|Arg|Lys|Lys|Thr|Asp|Glu|Leu|Pro|Gln|
| | |565| | | |570| | | |575| |

Lys Ser Glu Pro Leu Ile Gly Arg Lys Lys Thr Asp Glu Leu Pro Gln
                565                 570                 575

Leu Val Thr Leu Pro His Pro Asn Leu His Gly Pro Glu Ile Leu Asp
            580                 585                 590

Val Pro Ser Thr His Met Ala Ile Pro Ala Pro Thr Asp Leu Lys Phe
        595                 600                 605

Thr Gln Val Thr Pro Thr Ser Leu Ser Ala Gln Trp Thr Pro Pro Asn
    610                 615                 620

Val Gln Leu Thr Gly Tyr Arg Val Arg Val Thr Pro Lys Glu Lys Thr
625                 630                 635                 640

Gly Pro Met Lys Glu Ile Asn Leu Ala Pro Asp Ser Ser Ser Val Val
            645                 650                 655

Val Ser Gly Leu Met Val Ala Thr Lys Tyr Glu Val Ser Val Tyr Ala
        660                 665                 670

Leu Lys Asp Thr Leu Thr Ser Arg Pro Ala Gln Gly Val Val Thr Thr
    675                 680                 685

Leu Glu Asn Val Ser Pro Pro Arg Arg Ala Arg Val Thr Asp Ala Thr
690                 695                 700

Glu Thr Thr Ile Thr Ile Ser Trp Arg Thr Lys Thr Glu Thr Ile Thr
705                 710                 715                 720

Gly Phe Gln Val Asp Ala Val Pro Ala Asn Gly Gln Thr Pro Ile Gln
            725                 730                 735

Arg Thr Ile Lys Pro Asp Val Arg Ser Tyr Thr Ile Thr Gly Leu Gln
        740                 745                 750

Pro Gly Thr Asp Tyr Lys Ile Tyr Leu Tyr Thr Leu Asn Asp Asn Ala
    755                 760                 765

Arg Ser Ser Pro Val Val Ile Asp Ala Ser Thr Ala Ile Asp Ala Pro
770                 775                 780

Ser Asn Leu Arg Phe Leu Ala Thr Thr Pro Asn Ser Leu Leu Val Ser
785                 790                 795                 800

Trp Gln Pro Pro Arg Ala Arg Ile Thr Gly Tyr Ile Ile Lys Tyr Glu
            805                 810                 815

Lys Pro Gly Ser Pro Arg Glu Val Val Pro Arg Pro Arg Pro Gly
        820                 825                 830

Val Thr Glu Ala Thr Ile Thr Gly Leu Glu Pro Gly Thr Glu Tyr Thr
    835                 840                 845

Ile Tyr Val Ile Ala Leu Lys Asn Asn Gln Lys Ser Glu Pro Leu Ile
    850                 855                 860

Gly Arg Lys Lys Thr Asp Glu Leu Pro Gln Leu Val Thr Leu Pro His
865                 870                 875                 880

Pro Asn Leu His Gly Pro Glu Ile Leu Asp Val Pro Ser Thr
            885                 890

<210> SEQ ID NO 28
<211> LENGTH: 2685
<212> TYPE: DNA
<213> ORGANISM: Artificial Sequence
<220> FEATURE:
<223> OTHER INFORMATION: polynucleotide coding fibronectin fragment
      named H296-H296-H296

<400> SEQUENCE: 28
catatggcta ttcctgcacc aactgacctg aagttcactc aggtcacacc cacaagcctg    60
agcgcccagt ggacaccacc caatgttcag ctcactggat atcgagtgcg ggtgaccccc   120
aaggagaaga ccggaccaat gaaagaaatc aaccttgctc tgacagctc atccgtggtt    180

```
gtatcaggac ttatggtggc caccaaatat gaagtgagtg tctatgctct taaggacact    240
ttgacaagca gaccagctca gggagttgtc accactctgg agaatgtcag cccaccaaga    300
agggctcgtg tgacagatgc tactgagacc accatcacca ttagctggag aaccaagact    360
gagacgatca ctggcttcca agttgatgcc gttccagcca atggcagact ccaatccag     420 agaaccatca agccagatgt cagaagctac accatcacag gtttacaacc aggcactgac    480
tacaagatct acctgtacac cttgaatgac aatgctcgga ctcccctgt ggtcatcgac     540 gcctccactg ccattgatgc accatccaac ctgcgtttcc tggccaccac acccaattcc    600
ttgctggtat catggcagcc gccacgtgcc aggattaccg gctacatcat caagtatgag    660
aagcctgggt ctcctcccag agaagtggtc cctcggcccc gccctggtgt cacagaggct    720
actattactg gcctggaacc gggaaccgaa tatacaattt atgtcattgc cctgaagaat    780
aatcagaaga gcgagcccct gattggaagg aaaaagacag acgagcttcc ccaactggta    840
acccttccac accccaatct tcatggacca gagatcttgg atgttccttc cacacatatg    900
gctattcctg caccaactga cctgaagttc actcaggtca cacccacaag cctgagcgcc    960
cagtggacac cacccaatgt tcagctcact ggatatcgag tgcgggtgac ccccaaggag   1020
aagaccggac caatgaaaga aatcaacctt gctcctgaca gctcatccgt ggttgtatca   1080
ggacttatgg tggccaccaa atatgaagtg agtgtctatg ctcttaagga cactttgaca   1140
agcagaccag ctcagggagt tgtcaccact ctggagaatg tcagcccacc aagaagggct   1200
cgtgtgacag atgctactga gaccaccatc accattagct ggagaaccaa gactgagacg   1260
atcactggct tccaagttga tgccgttcca gccaatggcc agactccaat ccagagaacc   1320
atcaagccag atgtcagaag ctacaccatc acaggtttac aaccaggcac tgactacaag   1380
atctacctgt acaccttgaa tgacaatgct cggagctccc ctgtggtcat cgacgcctcc   1440
actgccattg atgcaccatc caacctgcgt ttcctggcca ccacacccaa ttccttgctg   1500
gtatcatggc agccgccacg tgccaggatt accggctaca tcatcaagta tgagaagcct   1560
gggtctcctc cagagaagt ggtccctcgg ccccgccctg gtgtcacaga ggctactatt    1620
actggcctgg aaccgggaac cgaatataca atttatgtca ttgccctgaa gaataatcag   1680
aagagcgagc ccctgattgg aaggaaaaag acagacgagc ttccccaact ggtaaccctt   1740 ccacaccca atcttcatgg accagagatc ttggatgttc cttccacaca tatggctatt    1800
cctgcaccaa ctgacctgaa gttcactcag gtcacaccca agcctgag cgcccagtgg     1860 acaccaccca atgttcagct cactggatat cgagtgcggg tgaccccaa ggagaagacc    1920 ggaccaatga agaaatcaa ccttgctcct gacagctcat ccgtggttgt atcaggactt    1980
atggtggcca caaatatga agtgagtgtc tatgctctta aggacacttt gacaagcaga   2040
ccagctcagg gagttgtcac cactctggag aatgtcagcc caccaagaag ggctcgtgtg   2100
acagatgcta ctgagaccac catcaccatt agctggagaa ccaagactga gacgatcact   2160
ggcttccaag ttgatgccgt tccagccaat ggccagactc caatccagag aaccatcaag   2220
ccagatgtca gaagctacac catcacaggt ttacaaccag gcactgacta caagatctac   2280
ctgtacacct tgaatgacaa tgctcggagc tcccctgtgg tcatcgacgc ctccactgcc   2340
attgatgcac catccaacct gcgtttcctg gccaccacac ccaattcctt gctggtatca   2400
tggcagccgc cacgtgccag gattaccggc tacatcatca gtatgagaa gcctgggtct    2460 cctcccagag aagtggtccc tcggccccgc cctggtgtca cagaggctac tattactggc   2520
ctggaaccgg gaaccgaata tacaatttat gtcattgccc tgaagaataa tcagaagagc   2580
```

```
gagcccctga ttggaaggaa aaagacagac gagcttcccc aactggtaac ccttccacac    2640
cccaatcttc atggaccaga gatcttggat gttccttcca cataa                   2685
```

<210> SEQ ID NO 29
<211> LENGTH: 234
<212> TYPE: PRT
<213> ORGANISM: Artificial Sequence
<220> FEATURE:
<223> OTHER INFORMATION: fibronectin fragment named H105-H105

<400> SEQUENCE: 29

```
His Met Ala Ile Asp Ala Pro Ser Asn Leu Arg Phe Leu Ala Thr Thr
1               5                   10                  15

Pro Asn Ser Leu Leu Val Ser Trp Gln Pro Pro Arg Ala Arg Ile Thr
            20                  25                  30

Gly Tyr Ile Ile Lys Tyr Glu Lys Pro Gly Ser Pro Pro Arg Glu Val
        35                  40                  45

Val Pro Arg Pro Arg Pro Gly Val Thr Glu Ala Thr Ile Thr Gly Leu
    50                  55                  60

Glu Pro Gly Thr Glu Tyr Thr Ile Tyr Val Ile Ala Leu Lys Asn Asn
65                  70                  75                  80

Gln Lys Ser Glu Pro Leu Ile Gly Arg Lys Lys Thr Asp Glu Leu Pro
                85                  90                  95

Gln Leu Val Thr Leu Pro His Pro Asn Leu His Gly Pro Glu Ile Leu
            100                 105                 110

Asp Val Pro Ser Thr His Met Ala Ile Asp Ala Pro Ser Asn Leu Arg
        115                 120                 125

Phe Leu Ala Thr Thr Pro Asn Ser Leu Leu Val Ser Trp Gln Pro Pro
    130                 135                 140

Arg Ala Arg Ile Thr Gly Tyr Ile Ile Lys Tyr Glu Lys Pro Gly Ser
145                 150                 155                 160

Pro Pro Arg Glu Val Val Pro Arg Pro Arg Pro Gly Val Thr Glu Ala
                165                 170                 175

Thr Ile Thr Gly Leu Glu Pro Gly Thr Glu Tyr Thr Ile Tyr Val Ile
            180                 185                 190

Ala Leu Lys Asn Asn Gln Lys Ser Glu Pro Leu Ile Gly Arg Lys Lys
        195                 200                 205

Thr Asp Glu Leu Pro Gln Leu Val Thr Leu Pro His Pro Asn Leu His
    210                 215                 220

Gly Pro Glu Ile Leu Asp Val Pro Ser Thr
225                 230
```

<210> SEQ ID NO 30
<211> LENGTH: 705
<212> TYPE: DNA
<213> ORGANISM: Artificial Sequence
<220> FEATURE:
<223> OTHER INFORMATION: polynucleotide coding fibronectin fragment
      named H105-H105

<400> SEQUENCE: 30

```
catatggcca ttgatgcacc atccaacctg cgtttcctgg ccaccacacc caattccttg     60
ctggtatcat ggcagccgcc acgtgccagg attaccggct acatcatcaa gtatgagaag    120
cctgggtctc ctcccagaga agtggtccct cggccccgcc tggtgtcac agaggctact     180 attactggcc tggaaccggg aaccgaatat acaatttatg tcattgccct gaagaataat    240
cagaagagcg agcccctgat tggaggaaa aagacagacg agcttcccca actggtaacc    300
```

```
cttccacacc ccaatcttca tggaccagag atcttggatg ttccttccac acatatggcc    360
attgatgcac catccaacct gcgtttcctg gccaccacac ccaattcctt gctggtatca    420
tggcagccgc cacgtgccag gattaccggc tacatcatca agtatgagaa gcctgggtct    480
cctcccagag aagtggtccc tcggccccgc cctggtgtca cagaggctac tattactggc    540
ctggaaccgg gaaccgaata tacaatttat gtcattgccc tgaagaataa tcagaagagc    600
gagcccctga ttggaaggaa aaagacagac gagcttcccc aactggtaac ccttccacac    660
cccaatcttc atggaccaga gatcttggat gttccttcca cataa                    705
```

<210> SEQ ID NO 31
<211> LENGTH: 34
<212> TYPE: DNA
<213> ORGANISM: Artificial Sequence
<220> FEATURE:
<223> OTHER INFORMATION: Synthetic primer H271-NcoR

<400> SEQUENCE: 31

```
gattacctac catggctgtc tttttccttc caat                                 34
```

<210> SEQ ID NO 32
<211> LENGTH: 569
<212> TYPE: PRT
<213> ORGANISM: Artificial Sequence
<220> FEATURE:
<223> OTHER INFORMATION: fibronectin fragment named H271-H296

<400> SEQUENCE: 32

```
Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
            20                  25                  30

Arg Val Arg Val Thr Pro Lys Glu Lys Thr Gly Pro Met Lys Glu Ile
        35                  40                  45

Asn Leu Ala Pro Asp Ser Ser Ser Val Val Val Ser Gly Leu Met Val
    50                  55                  60

Ala Thr Lys Tyr Glu Val Ser Val Tyr Ala Leu Lys Asp Thr Leu Thr
65                  70                  75                  80

Ser Arg Pro Ala Gln Gly Val Val Thr Thr Leu Glu Asn Val Ser Pro
                85                  90                  95

Pro Arg Arg Ala Arg Val Thr Asp Ala Thr Glu Thr Thr Ile Thr Ile
            100                 105                 110

Ser Trp Arg Thr Lys Thr Glu Thr Ile Thr Gly Phe Gln Val Asp Ala
        115                 120                 125

Val Pro Ala Asn Gly Gln Thr Pro Ile Gln Arg Thr Ile Lys Pro Asp
    130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
            180                 185                 190

Ala Thr Thr Pro Asn Ser Leu Leu Val Ser Trp Gln Pro Pro Arg Ala
        195                 200                 205

Arg Ile Thr Gly Tyr Ile Ile Lys Tyr Glu Lys Pro Gly Ser Pro Pro
    210                 215                 220

Arg Glu Val Val Pro Arg Pro Arg Pro Gly Val Thr Glu Ala Thr Ile
225                 230                 235                 240
```

```
Thr Gly Leu Glu Pro Gly Thr Glu Tyr Thr Ile Tyr Val Ile Ala Leu
            245                 250                 255
Lys Asn Asn Gln Lys Ser Glu Pro Leu Ile Gly Arg Lys Lys Thr Ala
            260                 265                 270
Met Ala Ile Pro Ala Pro Thr Asp Leu Lys Phe Thr Gln Val Thr Pro
            275                 280                 285
Thr Ser Leu Ser Ala Gln Trp Thr Pro Pro Asn Val Gln Leu Thr Gly
290                 295                 300
Tyr Arg Val Arg Val Thr Pro Lys Glu Lys Thr Gly Pro Met Lys Glu
305                 310                 315                 320
Ile Asn Leu Ala Pro Asp Ser Ser Ser Val Val Ser Gly Leu Met
                325                 330                 335
Val Ala Thr Lys Tyr Glu Val Ser Val Tyr Ala Leu Lys Asp Thr Leu
            340                 345                 350
Thr Ser Arg Pro Ala Gln Gly Val Val Thr Thr Leu Glu Asn Val Ser
            355                 360                 365
Pro Pro Arg Arg Ala Arg Val Thr Asp Ala Thr Glu Thr Thr Ile Thr
370                 375                 380
Ile Ser Trp Arg Thr Lys Thr Glu Thr Ile Thr Gly Phe Gln Val Asp
385                 390                 395                 400
Ala Val Pro Ala Asn Gly Gln Thr Pro Ile Gln Arg Thr Ile Lys Pro
            405                 410                 415
Asp Val Arg Ser Tyr Thr Ile Thr Gly Leu Gln Pro Gly Thr Asp Tyr
            420                 425                 430
Lys Ile Tyr Leu Tyr Thr Leu Asn Asp Asn Ala Arg Ser Ser Pro Val
            435                 440                 445
Val Ile Asp Ala Ser Thr Ala Ile Asp Ala Pro Ser Asn Leu Arg Phe
450                 455                 460
Leu Ala Thr Thr Pro Asn Ser Leu Leu Val Ser Trp Gln Pro Pro Arg
465                 470                 475                 480
Ala Arg Ile Thr Gly Tyr Ile Ile Lys Tyr Glu Lys Pro Gly Ser Pro
            485                 490                 495
Pro Arg Glu Val Val Pro Arg Pro Arg Pro Gly Val Thr Glu Ala Thr
            500                 505                 510
Ile Thr Gly Leu Glu Pro Gly Thr Glu Tyr Thr Ile Tyr Val Ile Ala
            515                 520                 525
Leu Lys Asn Asn Gln Lys Ser Glu Pro Leu Ile Gly Arg Lys Lys Thr
            530                 535                 540
Asp Glu Leu Pro Gln Leu Val Thr Leu Pro His Pro Asn Leu His Gly
545                 550                 555                 560
Pro Glu Ile Leu Asp Val Pro Ser Thr
            565
```

<210> SEQ ID NO 33
<211> LENGTH: 1713
<212> TYPE: DNA
<213> ORGANISM: Artificial Sequence
<220> FEATURE:
<223> OTHER INFORMATION: polynucleotide coding fibronectin fragment
      named H271-H296

<400> SEQUENCE: 33

```
atggctattc ctgcaccaac tgacctgaag ttcactcagg tcacacccac aagcctgagc      60
gcccagtgga caccccaa tgttcagctc actggatatc gagtgcgggt gaccccaag       120 gagaagaccg gaccaatgaa agaaatcaac cttgctcctg acagctcatc cgtggttgta    180
```

```
tcaggactta tggtggccac caaatatgaa gtgagtgtct atgctcttaa ggacactttg      240
acaagcagac cagctcaggg agttgtcacc actctggaga atgtcagccc accaagaagg      300
gctcgtgtga cagatgctac tgagaccacc atcaccatta gctggagaac caagactgag      360
acgatcactg gcttccaagt tgatgccgtt ccagccaatg gccagactcc aatccagaga      420
accatcaagc cagatgtcag aagctacacc atcacaggtt tacaaccagg cactgactac      480
aagatctacc tgtacacctt gaatgacaat gctcggagct cccctgtggt catcgacgcc      540
tccactgcca ttgatgcacc atccaacctg cgtttcctgg ccaccacacc caattccttg      600
ctggtatcat ggcagccgcc acgtgccagg attaccggct acatcatcaa gtatgagaag      660
cctgggtctc ctcccagaga agtggtccct cggccccgcc ctggtgtcac agaggctact      720
attactggcc tggaaccggg aaccgaatat acaattatg tcattgccct gaagaataat      780
cagaagagcg agcccctgat tggaaggaaa aagacagcca tggctattcc tgcaccaact      840
gacctgaagt tcactcaggt cacacccaca agcctgagcg cccagtggac accacccaat      900
gttcagctca ctggatatcg agtgcgggtg accccccaagg agaagaccgg accaatgaaa      960
gaaatcaacc ttgctcctga cagctcatcc gtggttgtat caggacttat ggtggccacc     1020
aaatatgaag tgagtgtcta tgctcttaag gacactttga caagcagacc agctcaggga     1080
gttgtcacca ctctggagaa tgtcagccca ccaagaaggg ctcgtgtgac agatgctact     1140
gagaccacca tcaccattag ctggagaacc aagactgaga cgatcactgg cttccaagtt     1200
gatgccgttc cagccaatgg ccagactcca atccagagaa ccatcaagcc agatgtcaga     1260
agctacacca tcacaggttt acaaccaggc actgactaca agatctacct gtacaccttg     1320
aatgacaatg ctcggagctc ccctgtggtc atcgacgcct ccactgccat tgatgcacca     1380
tccaacctgc gtttcctggc caccacaccc aattccttgc tggtatcatg gcagccgcca     1440
cgtgccagga ttaccggcta catcatcaag tatgagaagc tgggtctcc tcccagagaa     1500 gtggtccctc ggccccgccc tggtgtcaca gaggctacta ttactggcct ggaaccggga     1560
accgaatata caatttatgt cattgccctg aagaataatc agaagagcga gcccctgatt     1620
ggaaggaaaa agacagacga gcttccccaa ctggtaaccc ttccacaccc caatcttcat     1680
ggaccagaga tcttggatgt tccttccaca taa                                   1713
```

<210> SEQ ID NO 34
<211> LENGTH: 32
<212> TYPE: DNA
<213> ORGANISM: Artificial Sequence
<220> FEATURE:
<223> OTHER INFORMATION: Synthetic primer 12-Nco-F2

<400> SEQUENCE: 34
caaacaccat ggctattcct gcaccaactg ac                                    32

<210> SEQ ID NO 35
<211> LENGTH: 36
<212> TYPE: DNA
<213> ORGANISM: Artificial Sequence
<220> FEATURE:
<223> OTHER INFORMATION: Synthetic primer H271-BamR

<400> SEQUENCE: 35
ggtcgacgga tcctattatg tcttttctcct tccaat                               36

<210> SEQ ID NO 36
<211> LENGTH: 569

<212> TYPE: PRT
<213> ORGANISM: Artificial Sequence
<220> FEATURE:
<223> OTHER INFORMATION: fibronectin fragment named H296-H271

<400> SEQUENCE: 36

```
Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
            20                  25                  30

Arg Val Arg Val Thr Pro Lys Glu Lys Thr Gly Pro Met Lys Glu Ile
        35                  40                  45

Asn Leu Ala Pro Asp Ser Ser Ser Val Val Val Ser Gly Leu Met Val
    50                  55                  60

Ala Thr Lys Tyr Glu Val Ser Val Tyr Ala Leu Lys Asp Thr Leu Thr
65                  70                  75                  80

Ser Arg Pro Ala Gln Gly Val Val Thr Thr Leu Glu Asn Val Ser Pro
            85                  90                  95

Pro Arg Arg Ala Arg Val Thr Asp Ala Thr Glu Thr Thr Ile Thr Ile
        100                 105                 110

Ser Trp Arg Thr Lys Thr Glu Thr Ile Thr Gly Phe Gln Val Asp Ala
            115                 120                 125

Val Pro Ala Asn Gly Gln Thr Pro Ile Gln Arg Thr Ile Lys Pro Asp
130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
            180                 185                 190

Ala Thr Thr Pro Asn Ser Leu Leu Val Ser Trp Gln Pro Pro Arg Ala
        195                 200                 205

Arg Ile Thr Gly Tyr Ile Ile Lys Tyr Glu Lys Pro Gly Ser Pro Pro
    210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
            245                 250                 255

Lys Asn Asn Gln Lys Ser Glu Pro Leu Ile Gly Arg Lys Lys Thr Asp
        260                 265                 270

Glu Leu Pro Gln Leu Val Thr Leu Pro His Pro Asn Leu His Gly Pro
    275                 280                 285

Glu Ile Leu Asp Val Pro Ser Thr Ala Met Ala Ile Pro Ala Pro Thr
290                 295                 300

Asp Leu Lys Phe Thr Gln Val Thr Pro Thr Ser Leu Ser Ala Gln Trp
305                 310                 315                 320

Thr Pro Pro Asn Val Gln Leu Thr Gly Tyr Arg Val Arg Val Thr Pro
                325                 330                 335

Lys Glu Lys Thr Gly Pro Met Lys Glu Ile Asn Leu Ala Pro Asp Ser
            340                 345                 350

Ser Ser Val Val Val Ser Gly Leu Met Val Ala Thr Lys Tyr Glu Val
        355                 360                 365

Ser Val Tyr Ala Leu Lys Asp Thr Leu Thr Ser Arg Pro Ala Gln Gly
    370                 375                 380

Val Val Thr Thr Leu Glu Asn Val Ser Pro Pro Arg Arg Ala Arg Val
```

```
                385                 390                 395                 400
Thr Asp Ala Thr Glu Thr Thr Ile Thr Ile Ser Trp Arg Thr Lys Thr
                    405                 410                 415
Glu Thr Ile Thr Gly Phe Gln Val Asp Ala Val Pro Ala Asn Gly Gln
                420                 425                 430
Thr Pro Ile Gln Arg Thr Ile Lys Pro Asp Val Arg Ser Tyr Thr Ile
            435                 440                 445
Thr Gly Leu Gln Pro Gly Thr Asp Tyr Lys Ile Tyr Leu Tyr Thr Leu
        450                 455                 460
Asn Asp Asn Ala Arg Ser Ser Pro Val Val Ile Asp Ala Ser Thr Ala
465                 470                 475                 480
Ile Asp Ala Pro Ser Asn Leu Arg Phe Leu Ala Thr Thr Pro Asn Ser
                485                 490                 495
Leu Leu Val Ser Trp Gln Pro Pro Arg Ala Arg Ile Thr Gly Tyr Ile
            500                 505                 510
Ile Lys Tyr Glu Lys Pro Gly Ser Pro Pro Arg Glu Val Val Pro Arg
        515                 520                 525
Pro Arg Pro Gly Val Thr Glu Ala Thr Ile Thr Gly Leu Glu Pro Gly
    530                 535                 540
Thr Glu Tyr Thr Ile Tyr Val Ile Ala Leu Lys Asn Asn Gln Lys Ser
545                 550                 555                 560
Glu Pro Leu Ile Gly Arg Lys Lys Thr
                565

<210> SEQ ID NO 37
<211> LENGTH: 1713
<212> TYPE: DNA
<213> ORGANISM: Artificial Sequence
<220> FEATURE:
<223> OTHER INFORMATION: polynucleotide coding fibronectin fragment
      named H296-H271

<400> SEQUENCE: 37
atggctattc ctgcaccaac tgacctgaag ttcactcagg tcacacccac aagcctgagc     60
gcccagtgga caccacccaa tgttcagctc actggatatc gagtgcgggt gacccccaag    120
gagaagaccg gaccaatgaa agaaatcaac cttgctcctg acagctcatc cgtggttgta    180
tcaggactta tggtgccac caaatatgaa gtgagtgtct atgctcttaa ggacactttg    240
acaagcagac cagctcaggg agttgtcacc actctggaga atgtcagccc accaagaagg    300
gctcgtgtga cagatgctac tgagaccacc atcaccatta ctggagaac caagactgag    360
acgatcactg gcttccaagt tgatgccgtt ccagccaatg ccagactcc aatccagaga    420
accatcaagc cagatgtcag aagctacacc atcacaggtt acaaccagg cactgactac    480
aagatctacc tgtacaccct gaatgacaat gctcggagct cccctgtggt catcgacgcc    540
tccactgcca ttgatgcacc atccaacctg cgtttcctgg ccaccacacc caattccttg    600
ctggtatcat ggcagccgcc acgtgccagg attaccggct acatcatcaa gtatgagaag    660
cctgggtctc ctcccagaga agtggtccct cggccccgcc tggtgtcac agaggctact    720
attactggcc tggaaccggg aaccgaatat acaatttatg tcattgccct gaagaataat    780
cagaagagcg agcccctgat tggaaggaaa aagacagacg agcttcccca actggtaacc    840
cttccacacc ccaatcttca tggaccagag atcttggatg ttccttccac agccatggct    900
attcctgcac caactgacct gaagttcact caggtcacac ccacaagcct gagcgcccag    960
tggacaccac ccaatgttca gctcactgga tatcgagtgc gggtgacccc caaggagaag   1020
```

-continued

```
accggaccaa tgaaagaaat caaccttgct cctgacagct catccgtggt tgtatcagga    1080
cttatggtgg ccaccaaata tgaagtgagt gtctatgctc ttaaggacac tttgacaagc    1140
agaccagctc agggagttgt caccactctg gagaatgtca gcccaccaag aagggctcgt    1200
gtgacagatg ctactgagac caccatcacc attagctgga gaaccaagac tgagacgatc    1260
actggcttcc aagttgatgc cgttccagcc aatggccaga ctccaatcca gagaaccatc    1320
aagccagatg tcagaagcta caccatcaca ggtttacaac aggcactga ctacaagatc     1380 tacctgtaca ccttgaatga caatgctcgg agctcccctg tggtcatcga cgcctccact    1440
gccattgatg caccatccaa cctgcgtttc ctggccacca cacccaattc cttgctggta    1500
tcatggcagc cgccacgtgc caggattacc ggctacatca tcaagtatga aagcctgggg    1560
tctcctccca gaagtggt ccctcggccc cgccctggtg tcacagaggc tactattact      1620
ggcctggaac cgggaaccga atatacaatt tatgtcattg ccctgaagaa taatcagaag    1680
agcgagcccc tgattggaag gaaaaagaca taa                                 1713
```

<210> SEQ ID NO 38
<211> LENGTH: 33
<212> TYPE: DNA
<213> ORGANISM: Artificial Sequence
<220> FEATURE:
<223> OTHER INFORMATION: Synthetic primer Nde-15aa-F

<400> SEQUENCE: 38

```
ggtaggcata tgaatgacaa tgctcggagc tcc                                 33
```

<210> SEQ ID NO 39
<211> LENGTH: 265
<212> TYPE: PRT
<213> ORGANISM: Artificial Sequence
<220> FEATURE:
<223> OTHER INFORMATION: fibronectin fragment named 15aaH105-H105-HT

<400> SEQUENCE: 39

```
Met Asn His Lys Val His His His His His Ile Glu Gly Arg His
1               5                   10                  15

Met Asn Asp Asn Ala Arg Ser Ser Pro Val Val Ile Asp Ala Ser Thr
                20                  25                  30

Ala Ile Asp Ala Pro Ser Asn Leu Arg Phe Leu Ala Thr Thr Pro Asn
            35                  40                  45

Ser Leu Leu Val Ser Trp Gln Pro Pro Arg Ala Arg Ile Thr Gly Tyr
        50                  55                  60

Ile Ile Lys Tyr Glu Lys Pro Gly Ser Pro Pro Arg Glu Val Val Pro
65                  70                  75                  80

Arg Pro Arg Pro Gly Val Thr Glu Ala Thr Ile Thr Gly Leu Glu Pro
                85                  90                  95

Gly Thr Glu Tyr Thr Ile Tyr Val Ile Ala Leu Lys Asn Asn Gln Lys
            100                 105                 110

Ser Glu Pro Leu Ile Gly Arg Lys Lys Thr Asp Glu Leu Pro Gln Leu
        115                 120                 125

Val Thr Leu Pro His Pro Asn Leu His Gly Pro Glu Ile Leu Asp Val
    130                 135                 140

Pro Ser Thr Ala Met Ala Ala Ile Asp Ala Pro Ser Asn Leu Arg Phe
145                 150                 155                 160

Leu Ala Thr Thr Pro Asn Ser Leu Leu Val Ser Trp Gln Pro Pro Arg
                165                 170                 175

Ala Arg Ile Thr Gly Tyr Ile Ile Lys Tyr Glu Lys Pro Gly Ser Pro
```

```
                    180                 185                 190
Pro Arg Glu Val Val Pro Arg Pro Arg Gly Val Thr Glu Ala Thr
            195                 200                 205

Ile Thr Gly Leu Glu Pro Gly Thr Glu Tyr Thr Ile Tyr Val Ile Ala
        210                 215                 220

Leu Lys Asn Asn Gln Lys Ser Glu Pro Leu Ile Gly Arg Lys Lys Thr
225                 230                 235                 240

Asp Glu Leu Pro Gln Leu Val Thr Leu Pro His Pro Asn Leu His Gly
                245                 250                 255

Pro Glu Ile Leu Asp Val Pro Ser Thr
                260                 265

<210> SEQ ID NO 40
<211> LENGTH: 798
<212> TYPE: DNA
<213> ORGANISM: Artificial Sequence
<220> FEATURE:
<223> OTHER INFORMATION: polynucleotide coding fibronectin fragment
      named 15aaH105-H105-HT

<400> SEQUENCE: 40
atgaatcaca aagtgcatca tcatcatcat catatcgaag gtaggcatat gaatgacaat      60
gctcggagct cccctgtggt catcgacgcc tccactgcca ttgatgcacc atccaacctg     120
cgtttcctgg ccaccacacc caattccttg ctggtatcat ggcagccgcc acgtgccagg     180
attaccggct acatcatcaa gtatgagaag cctgggtctc ctcccagaga agtggtccct     240
cggccccgcc ctggtgtcac agaggctact attactggct ggaaccggg aaccgaatat     300 acaatttatg tcattgccct gaagaataat cagaagagcg agcccctgat tggaaggaaa     360
aagacagacg agcttcccca actggtaacc cttccacacc ccaatcttca tggaccagag     420
atcttggatg ttccttccac agccatggct gccattgatg caccatccaa cctgcgtttc     480
ctggccacca cacccaattc cttgctggta tcatggcagc cgccacgtgc caggattacc     540
ggctacatca tcaagtatga gaagcctggg tctcctccca gagaagtggt ccctcggccc     600
cgccctggtg tcacagaggc tactattact ggctggaac cggaaccga atatacaatt     660 tatgtcattg ccctgaagaa taatcagaag agcgagcccc tgattggaag gaaaaagaca     720
gacgagcttc ccaactggt aaccttcca caccccaatc ttcatggacc agagatcttg     780
gatgttcctt ccacataa                                                   798

<210> SEQ ID NO 41
<211> LENGTH: 250
<212> TYPE: PRT
<213> ORGANISM: Artificial Sequence
<220> FEATURE:
<223> OTHER INFORMATION: fibronectin fragment named 15aaH105-H105

<400> SEQUENCE: 41

His Met Asn Asp Asn Ala Arg Ser Ser Pro Val Val Ile Asp Ala Ser
1               5                   10                  15

Thr Ala Ile Asp Ala Pro Ser Asn Leu Arg Phe Leu Ala Thr Thr Pro
            20                  25                  30

Asn Ser Leu Leu Val Ser Trp Gln Pro Pro Arg Ala Arg Ile Thr Gly
        35                  40                  45

Tyr Ile Ile Lys Tyr Glu Lys Pro Gly Ser Pro Pro Arg Glu Val Val
    50                  55                  60

Pro Arg Pro Arg Pro Gly Val Thr Glu Ala Thr Ile Thr Gly Leu Glu
65                  70                  75                  80
```

```
Pro Gly Thr Glu Tyr Thr Ile Tyr Val Ile Ala Leu Lys Asn Asn Gln
                85                  90                  95

Lys Ser Glu Pro Leu Ile Gly Arg Lys Lys Thr Asp Glu Leu Pro Gln
            100                 105                 110

Leu Val Thr Leu Pro His Pro Asn Leu His Gly Pro Glu Ile Leu Asp
        115                 120                 125

Val Pro Ser Thr Ala Met Ala Ala Ile Asp Ala Pro Ser Asn Leu Arg
130                 135                 140

Phe Leu Ala Thr Thr Pro Asn Ser Leu Leu Val Ser Trp Gln Pro Pro
145                 150                 155                 160

Arg Ala Arg Ile Thr Gly Tyr Ile Ile Lys Tyr Glu Lys Pro Gly Ser
                165                 170                 175

Pro Pro Arg Glu Val Val Pro Arg Pro Arg Pro Gly Val Thr Glu Ala
            180                 185                 190

Thr Ile Thr Gly Leu Glu Pro Gly Thr Glu Tyr Thr Ile Tyr Val Ile
        195                 200                 205

Ala Leu Lys Asn Asn Gln Lys Ser Glu Pro Leu Ile Gly Arg Lys Lys
210                 215                 220

Thr Asp Glu Leu Pro Gln Leu Val Thr Leu Pro His Pro Asn Leu His
225                 230                 235                 240

Gly Pro Glu Ile Leu Asp Val Pro Ser Thr
                245                 250
```

<210> SEQ ID NO 42
<211> LENGTH: 753
<212> TYPE: DNA
<213> ORGANISM: Artificial Sequence
<220> FEATURE:
<223> OTHER INFORMATION: polynucleotide coding fibronectin fragment named 15aaH105-H105

<400> SEQUENCE: 42

```
catatgaatg acaatgctcg gagctcccct gtggtcatcg acgcctccac tgccattgat      60
gcaccatcca acctgcgttt cctggccacc acacccaatt ccttgctggt atcatggcag     120
ccgccacgtg ccaggattac cggctacatc atcaagtatg agaagcctgg gtctcctccc     180
agagaagtgg tccctcggcc ccgcctggt gtcacagagg ctactattac tggcctggaa      240
ccgggaaccg aatatacaat ttatgtcatt gccctgaaga ataatcagaa gagcgagccc     300
ctgattggaa ggaaaaagac agacgagctt ccccaactgg taacccttcc acacccaat     360
cttcatggac cagagatctt ggatgttcct tccacagcca tggctgccat tgatgcacca    420
tccaacctgc gtttcctggc caccacaccc aattccttgc tggtatcatg gcagccgcca    480
cgtgccagga ttaccggcta catcatcaag tatgagaagc ctgggtctcc tcccagagaa    540
gtggtccctc ggccccgcc tggtgtcaca gaggctacta ttactggcct ggaaccggga    600
accgaatata caatttatgt cattgccctg aagaataatc agaagagcga gcccctgatt    660
ggaaggaaaa agacagacga gcttccccaa ctggtaaccc ttccacaccc caatcttcat    720
ggaccagaga tcttggatgt tccttccaca taa                                 753
```

<210> SEQ ID NO 43
<211> LENGTH: 22
<212> TYPE: DNA
<213> ORGANISM: Artificial Sequence
<220> FEATURE:
<223> OTHER INFORMATION: oligonucleotide CpG-C

<400> SEQUENCE: 43

```
tcgtcgtttt cggcgcgcgc cg                                          22
```

<210> SEQ ID NO 44
<211> LENGTH: 9
<212> TYPE: PRT
<213> ORGANISM: Artificial Sequence
<220> FEATURE:
<223> OTHER INFORMATION: designed peptide based on matrix-protein
      derived from pp65

<400> SEQUENCE: 44

Asn Leu Val Pro Met Val Ala Thr Val
1               5

<210> SEQ ID NO 45
<211> LENGTH: 38
<212> TYPE: DNA
<213> ORGANISM: Artificial Sequence
<220> FEATURE:
<223> OTHER INFORMATION: Synthetic primer AID-F-Nco

<400> SEQUENCE: 45

```
ccactctggc catggctgcc attgatgcac catccaac                         38
```

<210> SEQ ID NO 46
<211> LENGTH: 36
<212> TYPE: DNA
<213> ORGANISM: Artificial Sequence
<220> FEATURE:
<223> OTHER INFORMATION: Synthetic primer CS1-R-Xba

<400> SEQUENCE: 46

```
gattacctat ctagattatg tggaaggaac atccaa                           36
```

<210> SEQ ID NO 47
<211> LENGTH: 250
<212> TYPE: PRT
<213> ORGANISM: Artificial Sequence
<220> FEATURE:
<223> OTHER INFORMATION: fibronectin fragment named H105-H105Nc-HT

<400> SEQUENCE: 47

Met Asn His Lys Val His His His His His His Ile Glu Gly Arg His
1               5                   10                  15

Met Ala Ile Asp Ala Pro Ser Asn Leu Arg Phe Leu Ala Thr Thr Pro
            20                  25                  30

Asn Ser Leu Leu Val Ser Trp Gln Pro Pro Arg Ala Arg Ile Thr Gly
        35                  40                  45

Tyr Ile Ile Lys Tyr Glu Lys Pro Gly Ser Pro Pro Arg Glu Val Val
    50                  55                  60

Pro Arg Pro Arg Pro Gly Val Thr Glu Ala Thr Ile Thr Gly Leu Glu
65                  70                  75                  80

Pro Gly Thr Glu Tyr Thr Ile Tyr Val Ile Ala Leu Lys Asn Asn Gln
                85                  90                  95

Lys Ser Glu Pro Leu Ile Gly Arg Lys Lys Thr Asp Glu Leu Pro Gln
            100                 105                 110

Leu Val Thr Leu Pro His Pro Asn Leu His Gly Pro Glu Ile Leu Asp
        115                 120                 125

Val Pro Ser Thr Ala Met Ala Ala Ile Asp Ala Pro Ser Asn Leu Arg
    130                 135                 140

Phe Leu Ala Thr Thr Pro Asn Ser Leu Leu Val Ser Trp Gln Pro Pro
145                 150                 155                 160

Arg Ala Arg Ile Thr Gly Tyr Ile Ile Lys Tyr Glu Lys Pro Gly Ser
                165                 170                 175

Pro Pro Arg Glu Val Val Pro Arg Pro Arg Pro Gly Val Thr Glu Ala
            180                 185                 190

Thr Ile Thr Gly Leu Glu Pro Gly Thr Glu Tyr Thr Ile Tyr Val Ile
        195                 200                 205

Ala Leu Lys Asn Asn Gln Lys Ser Glu Pro Leu Ile Gly Arg Lys Lys
    210                 215                 220

Thr Asp Glu Leu Pro Gln Leu Val Thr Leu Pro His Pro Asn Leu His
225                 230                 235                 240

Gly Pro Glu Ile Leu Asp Val Pro Ser Thr
                245                 250

<210> SEQ ID NO 48
<211> LENGTH: 753
<212> TYPE: DNA
<213> ORGANISM: Artificial Sequence
<220> FEATURE:
<223> OTHER INFORMATION: polynucleotide coding fibronectin fragment
      named H105-H105Nc-HT

<400> SEQUENCE: 48
atgaatcaca aagtgcatca tcatcatcat catatcgaag gtaggcatat ggccattgat    60
gcaccatcca acctgcgttt cctggccacc acacccaatt ccttgctggt atcatggcag   120
ccgccacgtg ccaggattac cggctacatc atcaagtatg agaagcctgg gtctcctccc   180
agagaagtgg tccctcggcc ccgccctggt gtcacagagg ctactattac tggcctggaa   240
ccgggaaccg aatatacaat ttatgtcatt gccctgaaga ataatcagaa gagcgagccc   300
ctgattggaa ggaaaaagac agacgagctt ccccaactgg taacccttcc acaccccaat   360
cttcatggac cagagatctt ggatgttcct tccacagcca tggctgccat tgatgcacca   420
tccaacctgc gtttcctggc caccacaccc aattccttgc tggtatcatg gcagccgcca   480
cgtgccagga ttaccggcta catcatcaag tatgagaagc tgggtctccc tccagagaa    540 gtggtccctc ggccccgccc tggtgtcaca gaggctacta ttactggcct ggaaccggga   600
accgaatata caatttatgt cattgccctg aagaataatc agaagagcga gcccctgatt   660
ggaaggaaaa agacagacga gcttccccaa ctggtaaccc ttccacaccc caatcttcat   720
ggaccagaga tcttggatgt tccttccaca taa                                753

<210> SEQ ID NO 49
<211> LENGTH: 235
<212> TYPE: PRT
<213> ORGANISM: Artificial Sequence
<220> FEATURE:
<223> OTHER INFORMATION: fibronectin fragment named H105-H105Nc

<400> SEQUENCE: 49

His Met Ala Ile Asp Ala Pro Ser Asn Leu Arg Phe Leu Ala Thr Thr
1               5                   10                  15

Pro Asn Ser Leu Leu Val Ser Trp Gln Pro Pro Arg Ala Arg Ile Thr
            20                  25                  30

Gly Tyr Ile Ile Lys Tyr Glu Lys Pro Gly Ser Pro Pro Arg Glu Val
        35                  40                  45

Val Pro Arg Pro Arg Pro Gly Val Thr Glu Ala Thr Ile Thr Gly Leu
    50                  55                  60

Glu Pro Gly Thr Glu Tyr Thr Ile Tyr Val Ile Ala Leu Lys Asn Asn
65                  70                  75                  80

```
Gln Lys Ser Glu Pro Leu Ile Gly Arg Lys Lys Thr Asp Glu Leu Pro
                85                  90                  95

Gln Leu Val Thr Leu Pro His Pro Asn Leu His Gly Pro Glu Ile Leu
            100                 105                 110

Asp Val Pro Ser Thr Ala Met Ala Ala Ile Asp Ala Pro Ser Asn Leu
        115                 120                 125

Arg Phe Leu Ala Thr Thr Pro Asn Ser Leu Leu Val Ser Trp Gln Pro
    130                 135                 140

Pro Arg Ala Arg Ile Thr Gly Tyr Ile Ile Lys Tyr Glu Lys Pro Gly
145                 150                 155                 160

Ser Pro Pro Arg Glu Val Val Pro Arg Pro Arg Pro Gly Val Thr Glu
                165                 170                 175

Ala Thr Ile Thr Gly Leu Glu Pro Gly Thr Glu Tyr Thr Ile Tyr Val
            180                 185                 190

Ile Ala Leu Lys Asn Asn Gln Lys Ser Glu Pro Leu Ile Gly Arg Lys
        195                 200                 205

Lys Thr Asp Glu Leu Pro Gln Leu Val Thr Leu Pro His Pro Asn Leu
    210                 215                 220

His Gly Pro Glu Ile Leu Asp Val Pro Ser Thr
225                 230                 235
```

<210> SEQ ID NO 50
<211> LENGTH: 708
<212> TYPE: DNA
<213> ORGANISM: Artificial Sequence
<220> FEATURE:
<223> OTHER INFORMATION: polynucleotide coding fibronectin fragment named H105-H105Nc

<400> SEQUENCE: 50

| | |
|---|---:|
| catatggcca ttgatgcacc atccaacctg cgtttcctgg ccaccacacc caattccttg | 60 |
| ctggtatcat ggcagccgcc acgtgccagg attaccggct acatcatcaa gtatgagaag | 120 |
| cctgggtctc ctcccagaga agtggtccct cggccccgcc ctggtgtcac agaggctact | 180 |
| attactggcc tggaaccggg aaccgaatat acaatttatg tcattgccct gaagaataat | 240 |
| cagaagagcg agcccctgat tggaaggaaa aagacagacg agcttcccca actggtaacc | 300 |
| cttccacacc ccaatcttca tggaccagag atcttggatg ttccttccac agccatggct | 360 |
| gccattgatg caccatccaa cctgcgtttc ctggccacca cacccaattc cttgctggta | 420 |
| tcatggcagc cgccacgtgc caggattacc ggctacatca tcaagtatga aagcctggg | 480 |
| tctcctccca gagaagtggt ccctcggccc cgccctggtg tcacagaggc tactattact | 540 |
| ggcctggaac cgggaaccga atatacaatt tatgtcattg ccctgaagaa taatcagaag | 600 |
| agcgagcccc tgattggaag gaaaaagaca gacgagcttc ccaactggt aacccttcca | 660 |
| cacccaatc ttcatggacc agagatcttg gatgttcctt ccacataa | 708 |

<210> SEQ ID NO 51
<211> LENGTH: 132
<212> TYPE: PRT
<213> ORGANISM: Artificial Sequence
<220> FEATURE:
<223> OTHER INFORMATION: fibronectin fragment named H105-HT

<400> SEQUENCE: 51

```
Met Asn His Lys Val His His His His His His Ile Glu Gly Arg His
1               5                   10                  15

Met Ala Ile Asp Ala Pro Ser Asn Leu Arg Phe Leu Ala Thr Thr Pro
```

```
                  20                  25                  30

Asn Ser Leu Leu Val Ser Trp Gln Pro Pro Arg Ala Arg Ile Thr Gly
        35                  40                  45

Tyr Ile Ile Lys Tyr Glu Lys Pro Gly Ser Pro Pro Arg Glu Val Val
        50                  55                  60

Pro Arg Pro Arg Pro Gly Val Thr Glu Ala Thr Ile Thr Gly Leu Glu
65                  70                  75                  80

Pro Gly Thr Glu Tyr Thr Ile Tyr Val Ile Ala Leu Lys Asn Asn Gln
                85                  90                  95

Lys Ser Glu Pro Leu Ile Gly Arg Lys Lys Thr Asp Glu Leu Pro Gln
                100                 105                 110

Leu Val Thr Leu Pro His Pro Asn Leu His Gly Pro Glu Ile Leu Asp
        115                 120                 125

Val Pro Ser Thr
        130

<210> SEQ ID NO 52
<211> LENGTH: 399
<212> TYPE: DNA
<213> ORGANISM: Artificial Sequence
<220> FEATURE:
<223> OTHER INFORMATION: polynucleotide coding fibronectin fragment
      named H105-HT

<400> SEQUENCE: 52
atgaatcaca aagtgcatca tcatcatcat catatcgaag gtaggcatat ggccattgat      60
gcaccatcca acctgcgttt cctggccacc acacccaatt ccttgctggt atcatggcag    120
ccgccacgtg ccaggattac cggctacatc atcaagtatg agaagcctgg gtctcctccc    180
agagaagtgg tccctcggcc ccgccctggt gtcacagagg ctactattac tggcctggaa    240
ccgggaaccg aatatacaat ttatgtcatt gccctgaaga ataatcagaa gagcgagccc    300
ctgattggaa ggaaaaagac agacgagctt ccccaactgg taaccctttcc acacccaat    360 cttcatggac cagagatctt ggatgttcct tccacataa                           399

<210> SEQ ID NO 53
<211> LENGTH: 16
<212> TYPE: PRT
<213> ORGANISM: Artificial Sequence
<220> FEATURE:
<223> OTHER INFORMATION: Synthetic peptide: His-tag sequence

<400> SEQUENCE: 53

Met Asn His Lys Val His His His His His His Ile Glu Gly Arg His
1               5                   10                  15
```